United States Patent
Ohtani et al.

(10) Patent No.: US 6,407,104 B1
(45) Date of Patent: Jun. 18, 2002

(54) PYRROLO[1,2-A]PYRAZINE SPLA$_2$ INHIBITOR

(75) Inventors: Mitsuaki Ohtani; Masahiro Fuji; Tetsuo Okada, all of Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/623,591

(22) PCT Filed: Mar. 31, 1999

(86) PCT No.: PCT/JP99/01670

§ 371 (c)(1),
(2), (4) Date: Sep. 5, 2000

(87) PCT Pub. No.: WO99/51605

PCT Pub. Date: Oct. 14, 1999

(30) Foreign Application Priority Data

Mar. 31, 1998 (JP) .......................................... 10-085997
Aug. 31, 1998 (JP) .......................................... 10-244735

(51) Int. Cl.$^7$ ..................... A61K 31/519; C07D 487/04
(52) U.S. Cl. .................... 514/233.2; 514/248; 544/116; 544/349
(58) Field of Search ................................ 544/116, 349; 514/233.2, 248

(56) References Cited

FOREIGN PATENT DOCUMENTS

| | | |
|---|---|---|
| EP | 0 620 214 A1 | 10/1994 |
| EP | 0 620 214 A | 10/1994 |
| EP | 0 620 215 A1 | 10/1994 |
| EP | 0 675 110 A1 | 10/1995 |
| WO | WO 97/21664 | 6/1987 |
| WO | WO 96/03120 A | 2/1996 |
| WO | WO 96/03120 | 2/1996 |
| WO | WO 96/03376 | 2/1996 |
| WO | WO 96/03383 | 2/1996 |
| WO | WO 96/03383 A | 2/1996 |
| WO | WO 97/21716 | 6/1997 |
| WO | WO 98/18464 | 5/1998 |
| WO | WO 98/24437 | 6/1998 |
| WO | WO 98/24756 | 6/1998 |
| WO | WO 98/24794 | 6/1998 |
| WO | WO 98/25609 | 6/1998 |
| WO | WO 99/00360 | 1/1999 |

OTHER PUBLICATIONS

S. Hagishita et al., J. Med. Chem., vol. 39, "Potent Inhibitors of Secretory Phospholipase A2: Synthesis and Inhibitory Activities of Indolizine and Indene Derivatives," pp. 3636–3658 (1996).

G. Karmas et al., J. Am. Chem. Soc., vol. 74, "The Preparation of Hydroxyprazines and Derived Chloropyrazines," pp. 1580–1584 (1952).

E. Corey et al., Tetrahedron Letters, No. 31, "Pyridinium Chlorochromate. An Efficient Reagent for Oxidation of Primary and Secondary Alcohols to Carbonyl Compounds," pp. 2647–2560 (1975).

A. Mancuso et al., J. Org. Chem., vol. 43, No. 12, "Oxidation of Long–Chain and Related Alcohols to Carbonyls by Dimethyl Sulfoxide 'Activated' by Oxalyl Chloride," pp. 2480–2482 (1978).

D. Dess et al., J. Org. Chem., vol. 48, "Readily Accessible 12–I–5$^1$ Oxidant for the Conversion of Primary and Secondary Alcohols to Aldehydes and Ketones," pp. 4155–4156 (1983).

P. Anelli et al., J. Org. Chem., vol. 52, "Fast Selective Oxidation of Primary Alcohols to Aldehydes or to Carboxylic Acids and of Secondary Alcohols to Ketones Mediated by Oxoammonium Salts Under Two–Phase Conditions," pp. 2559–2562 (1987).

N. Miyaura et al., Synthetic Communications, vol. 11, No. 7, "The Palladium–Catalyzed Cross–Coupling Reaction of Phenylboronic Acid with Haloarenes in the Presence of Bases," pp. 513–519 (1981).

K. Sonogashira et al., Tetrahedron Letters, No. 50, "A Convenient Synthesis of Acetylenes: Catalytic Substitutions of Acetylenic Hydrogen with Bromoalkenes, Iodoarenes, and Bromopyridines," pp. 4467–4470 (1975).

V. Bobošik et al., Monatshefte Für Chemie, vol. 126, "Synthesis and Reactions of 2,3–dimethylfuro[3,2–c]pyridines#," pp. 747–752 (1995).

E. Stoner et al., Tetrahedron, vol. 51, No. 41, "Benzylation via Tandem Grignard Reaction –Iodotrimethylsilane (TMSI) Mediated Reduction," pp. 11043–11062 (1995).

K. Kusuda et al., Tetrahedron Letters, vol. 30, No. 22, "A Highly Efficient Deoxygenation of α–Oxygenated Esters Via SmI$_2$–Inducted Electron Transfer Process," pp. 2945–2948 (1989).

S. Berge et al., J. Pharm. Sci., vol. 66, No. 1, "Pharmaceutical Salts," pp. 1–19 (1977).

(List continued on next page.)

Primary Examiner—Fiona T. Powers
(74) Attorney, Agent, or Firm—Foley & Lardner

(57) ABSTRACT

(I)

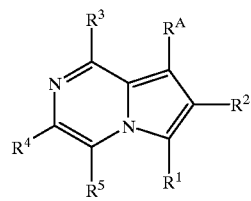

wherein R$^1$ is —(L$^1$)—R$^6$ wherein L$^1$ is a divalent linking group of 1 to 18 atoms or the like, and R$^6$ is a carbocyclic ring substituted by at least one non-interfering substituent or the like; R$^2$ is C1 to C3 alkyl, C3 to C4 cycloalkyl or the like group; R$^3$ is —(L$^2$)-(acidic group); R$^4$ and R$^5$ are hydrogen atoms, non-interfering substituents, carbocyclic groups or the like; R$^A$ is —C(=X)—C(=X)—NH$_2$ or the like; and X is independently oxygen atom or sulfur atom; the prodrugs thereof, their pharmaceutically acceptable salts, or their solvates, and a composition for inhibiting sPLA$_2$ containing them as effective ingredients.

24 Claims, No Drawings

OTHER PUBLICATIONS

Design of Prodrugs, pp. 7–9 and 21–24 (1985), Elsevier, New York.

D. McHattie et al., Heterocycles, vol. 34, No. 9, "The Synthesis of Pyrrolo[1,2–α]Pyrazin–1(2H)–Ones and Pyrrolo[1,2–b]Pyridazin–6(5H)–Ones," pp. 1759–1771 (1992).

E. Alexander et al., Organic Syntheses Collective, vol. 3, "Ethyl n–Butylcyanoacetate," pp. 385–386 (1955).

E. Alexander et al., J. Am. Chem. Soc., vol. 66, "A Simultaneous Condensation–Reduction Method for the Preparation of Ethyl Monoalkylcyanoacetates," pp. 886–888 (1944).

I. Yamawaki et al., Eur. J. Med. Chem., vol. 28, "Synthesis and aldose reductase inhibitory activity of acetic acid derivatives of pyrrolo[1,2–c]imidazole," pp. 481–498 (1993).

S. Ram et al., Synthetic Communications, vol. 22, No. 18, "Temperature and Solvent Dependent Catalytic Transfer Hydrogenolysis in Aromatic Aldehydes and Ketones Via Ammonium Formate," pp. 2673–2681 (1992).

L. Reynolds et al., Analytical Biochemistry, vol. 204, "Analysis of Human Synovial Fluid Phospholipase $A_2$ on Short Chain Phosphyatidylcholine–Mixed Micelles: Development of a Spectrophotometric Assay Suitable for a Microtiterplate Reader," pp. 190–197 (1992).

PYRROLO[1,2-A]PYRAZINE SPLA₂ INHIBITOR

TECHNICAL FIELD

The present invention relates to a pyrrolo[1,2-a]pyrazine derivative effective for inhibiting sPLA$_2$-mediated fatty acid release.

BACKGROUND ART sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, cardiac infarction, and so on. The participation of sPLA$_2$ is considered to be extremely wide and, besides, its action is potent.

There are known, as examples of sPLA$_2$ inhibitor, indole derivatives in EP-620214 (JP Laid-Open No. 010838/95), EP-620215 (JP Laid-Open No. 025850/95), EP-675110 (JP Laid-Open No. 285933/95), WO 96/03376, and WO 99/00360; indene derivatives in WO 96/03120; indolizine derivatives in WO 96/03383; naphthalene derivatives in WO 97/21664 and WO 97/21716; tricyclic derivatives in WO 98/18464; pyrazole derivatives in WO 98/24437; phenylacetamide derivatives in WO 98/24756; phenyl glyoxamide derivatives in WO 98/24794; pyrrole derivatives in WO 98/25609.

DISCLOSURE OF INVENTION

The present invention provides pyrrolo[1,2-a]pyrazine derivatives having sPLA$_2$ inhibiting activity and being useful for treatment of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, psoriasis, cardiac failure, and cardiac infarction.

The present invention relates to a compound represented by the formula (I):

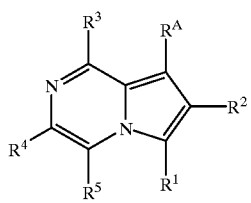

(I)

wherein R$^1$ is hydrogen atom or a group selected from (a) C6 to C20 alkyl, C6 to C20 alkenyl, C6 to C20 alkynyl, carbocyclic groups, and heterocyclic groups, (b) the groups represented by (a) each substituted independently with at least one group selected from non-interfering substituents, and (c) —(L$^1$)—R$^6$ wherein L$^1$ is a divalent linking group of 1 to 18 atom(s) selected from hydrogen atom(s), nitrogen atom(s), carbon atom(s), oxygen atom(s), and sulfur atom(s), and R$^6$ is a group selected from the groups (a) and (b);

R$^2$ is hydrogen atom, or a group containing 1 to 4 non-hydrogen atoms;

R$^3$ is —(L$^2$)—(acidic group) wherein L$^2$ is an acid linker having an acid linker length of 1 to 5;

R$^4$ and R$^5$ are selected independently from hydrogen atom, non-interfering substituents, carbocyclic groups, carbocyclic groups substituted with a non-interfering substituent(s), heterocyclic groups, and heterocyclic groups substituted by a non-interfering substituent(s); and R$^A$ is a group represented by the formula:

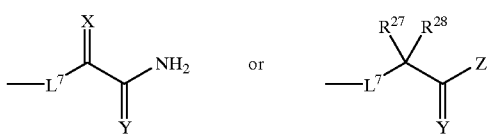

wherein L$^7$ is a divalent linker group selected from a bond or a divalent group selected from —CH$_2$—, —O—, —S—, —NH—, or —CO—, R$^{27}$ and R$^{28}$ are independently hydrogen atom, C1 to C3 alkyl or a halogen; X and Y are independently an oxygen atom or a sulfur atom; and Z is —NH$_2$ or —NHNH$_2$; the prodrugs thereof; or their pharmaceutically acceptable salts; or their solvates.

Preferred subclass of compounds of formula (I) are those where for R$^1$ is the divalent linking group —(L$^1$)— is a group represented by any one of the following formula (Ia) or (Ib) or (Ic):

 (Ia)

 (Ib)

 (Ic)

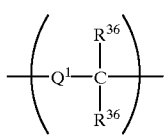

wherein Q$^1$ is a bond or any one of the divalent groups (Ia) or (Ib) and each R$^{36}$ is independently hydrogen atom, C1 to C8 alkyl, C1 to C8 haloalkyl, or C1 to C8 alkyloxy. Particularly preferred as the linking group —(L$^1$)— of R$^1$ is an alkylene chain of 1 or 2 carbon atoms, namely, —(CH$_2$)— or —(CH$_2$CH$_2$)—.

Preferred sPLA$_2$ inhibitor compounds of the invention are those represented by the formula (II):

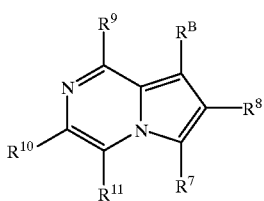

(II)

wherein R$^7$ is hydrogen atom or —(CH$_2$)m—R$^{12}$ wherein m is an integer from 1 to 6, and R$^{12}$ is (d) a group represented by the formula:

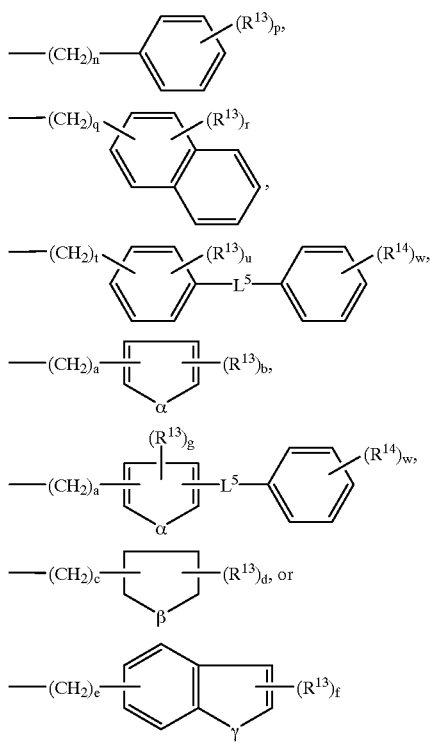

wherein a, c, e, n, q, and t are independently an integer from 0 to 2, R$^{13}$ and R$^{14}$ are independently selected from a halogen, C1 to C10 alkyl, C1 to C10 alkyloxy, C1 to C10 alkylthio, aryl, heteroaryl, and C1 to C10 haloalkyl, α is an oxygen atom or a sulfur atom, L$^5$ is —(CH$_2$)v—, —C=C—, —C≡C—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, g is an integer from 0 to 2, r is an integer from 0 to 7, and u is an integer from 0 to 4, or is (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen;

R$^8$ is C1 to C3 alkyl, C1 to C3 alkenyl, C3 to C4 cycloalkyl, C3 to C4 cycloalkenyl, C1 to C2 haloalkyl, C1 to C3 alkyloxy, or C1 to C3 alkylthio;

R$^9$ is —(L$^3$)—R$^{15}$ wherein L$^3$ is represented by the formula:

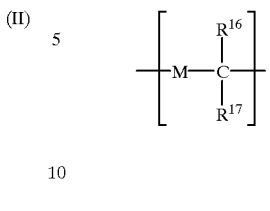

wherein M is —CH$_2$—, —O—, —N(R$^{24}$)—, or —S—, R$^{16}$ and R$^{17}$ are independently hydrogen atom, C1 to C10 alkyl, aryl, aralkyl, alkyloxy, haloalkyl, carboxy, or a halogen, and R$^{24}$ is hydrogen atom or C1 to C6 alkyl, and R$^{15}$ is represented by the formula:

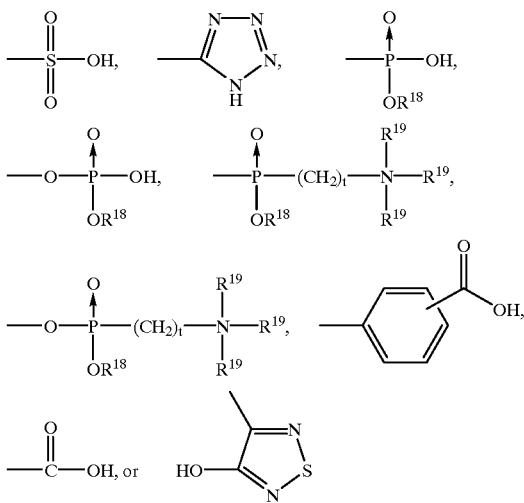

wherein R$^{18}$ is hydrogen atom, a metal, or C1 to C10 alkyl, R$^{19}$ is independently hydrogen atom, or C1 to C10 alkyl, and t is an integer from 1 to 8;

R$^{10}$ and R$^{11}$ are independently hydrogen atom or a non-interfering substituent selected from hydrogen, C1 to C8 alkyl, C2 to C8 alkenyl, C2 to C8 alkenyl, C7 to C12 aralkyl, C7 to C12 alkaryl, C3 to C8 cycloalkyl, C3 to C8 cycloalkenyl, phenyl, tolyl, xylyl, biphenyl, C1 to C8 alkyloxy, C2 to C8 alkenyloxy, C2 to C8 alkynyloxy, C2 to C12 alkyloxyalkyl, C2 to C12 alkyloxyalkyloxy, C2 to C12 alkylcarbonyl, C2 to C12 alkylcarbonylamino, C2 to C12 alkyloxyamino, C2 to C12 alkyloxyaminocarbonyl, C1 to C12 alkylamino, C1 to C6 alkylthio, C2 to C12 alkylthiocarbonyl, C1 to C8 alkylsulfinyl, C1 to C8 alkylsulfonyl, C2 to C8 haloalkyloxy, C1 to C8 haloalkylsulfonyl, C2 to C8 haloalkyl, C1 to C8 hydroxyalkyl, —C(O)O(C1 to C8 alkyl), —(CH$_2$)z—O—(C1 to C8 alkyl), benzyloxy, aryloxy, arylthio, —(CONHSO$_2$R$^{25}$), —CHO, amino, amidino, halogen, carbamyl, carboxyl, carbalkoxy, —(CH$_2$)z—CO$_2$H, cyano, cyanoguanidinyl, guanidino, hydrazide, hydrazino, hydrazido, hydroxy, hydroxyamino, iodo, nitro, phosphono, —SO$_3$H, thioacetal, thiocarbonyl, or carbonyl, R$^{25}$ is C1 to C6 alkyl or aryl, z is an integer from 1 to 8; and $R^B$ is a group represented by the formula:

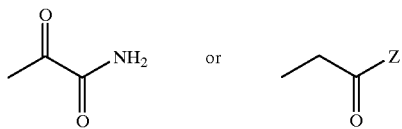

wherein Z is the same as defined above; the prodrugs thereof, or their pharmaceutically acceptable salts, or their solvates.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

The invention also relates to preferred compounds represented by formula (I) or (II) the prodrugs thereof, or their pharmaceutically acceptable salts, or their solvates, wherein said $R^1$ and $R^7$ are represented by the formula:

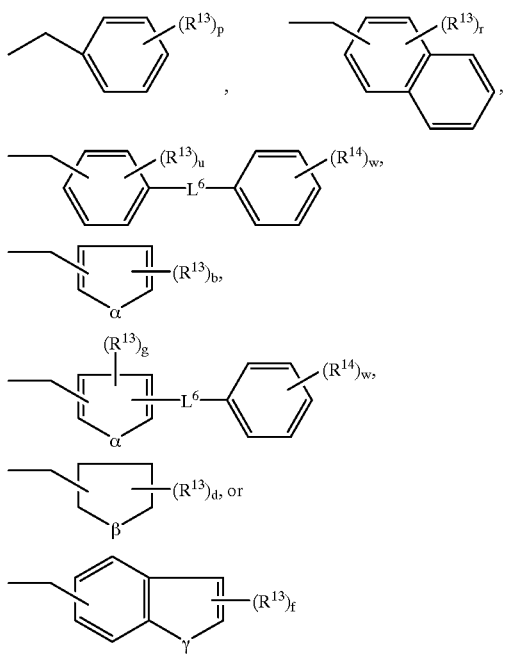

wherein $R^{13}$, $R^{14}$, b, d, f, g, p, r, u, w, α, β, and γ are the same as defined above, $L^6$ is a bond, —CH₂—, —C=C—, —C≡C—, —O—, or —S—.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

The invention also relates to preferred compounds represented by formula (I) and (II), the prodrugs thereof, or their pharmaceutically acceptable salts, or their solvates, wherein for the formula (I) and (II) respectively the substituent $R^2$ or $R^8$ is selected from C1 to C3 alkyl or C3 to C4 cycloalkyl.

The invention also relates to a preferred compound of formula (I) or (II), the prodrugs thereof or their pharmaceutically acceptable salts, or their solvates, wherein the $L^2$ and $L^3$ are —O—CH₂—.

The invention also relates to a preferred compound represented by the formula (III):

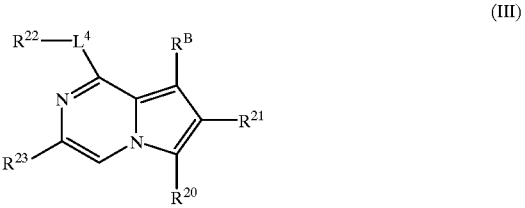

(III)

wherein $R^{20}$ is a group represented by the formula:

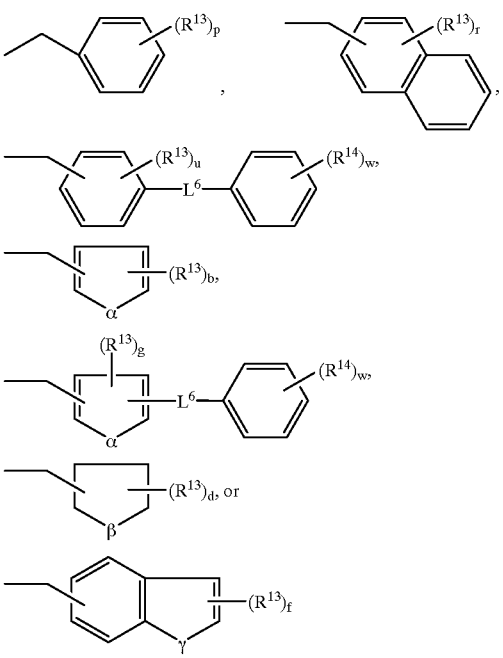

wherein $L^6$, $R^{13}$ $R^{14}$, b, d, f, g, p, r, u, w, α, β and γ are the same as defined above;

$R^{21}$ is C1 to C3 alkyl or C3 to C4 cycloalkyl;

$L^4$ is —O—CH₂—, —S—CH₂—, —N($R^{24}$)—CH₂—, —CH₂—CH—, —O—CH(CH₃)—, or —O—CH((CH₂)₂Ph)— wherein $R^{24}$ is hydrogen atom or C1 to C6 alkyl and Ph is phenyl;

$R^{22}$ is —COOH, —SO₃H, or P(O)(OH)₂;

$R^{23}$ is hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, arylthio, a carbocyclic group, or a heterocyclic group; and $R^B$ is the same as defined above; the prodrugs thereof; or their pharmaceutically acceptable salts; or their solvates.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

The invention also relates to most preferred compounds represented by the formula (IV):

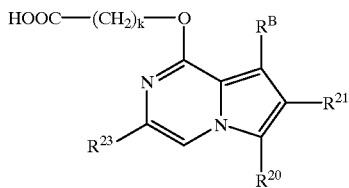

(IV)

wherein $R^{20,}$ $R^{21},$ $R^{23,}$ and $R^B$ are the same as defined above; and k is an integer from 1 to 3; the prodrugs thereof; or their pharmaceutically acceptable salts; or their solvates.

The invention also relates to a preferred compound, the prodrugs thereof, or their pharmaceutically acceptable salts, or their solvates as described in formula (III) wherein $L^4$ is —O—CH$_2$—.

The invention further relates to a preferred compound, the prodrugs thereof, or their pharmaceutically acceptable salts, or their solvates as described in formula (I), (II), (III), or (IV), wherein $R^A$ and $R^B$ are —COCONH$_2$—.

The invention also relates to preferred compounds formula (I), (II), (III), or (IV), the prodrugs thereof, or their pharmaceutically acceptable salts, or their solvates wherein $R^A$ and $R^B$ are —CH$_2$CONH$_2$—.

The invention further relates to preferred compounds of formula (I), (II), (III), or (IV), the prodrugs thereof, or their pharmaceutically acceptable salts, or their solvates wherein $R^A$ and $R^B$ are —CH$_2$CONHNH$_2$—.

The invention also relates to preferred compounds of formula (I), (II), (III), or (IV) in the form of ester type prodrug.

The invention further relates to specific preferred sPLA$_2$ inhibitor compounds of formula (I), (II), (III), or (IV), namely, a pyrrolo[1,2-a]pyrazine compound selected from the group consisting of:
[6-Benzyl-7-ethyl-8-oxamoylpyrrolo[1,2-a]pyrazin-1-yl]oxyacetic acid,
[6-Cyclohexylmethyl-7-ethyl-8-oxamoylpyrrolo [1,2-a]pyrazin-1-yl]oxyacetic acid,
[7-Ethyl-6-(3-methoxybenzyl)-8-oxamoylpyrrolo[1,2-a]pyrazin-1-yl]oxyacetic acid,
[6-(Benzo[b]thiophen-6-ylmethyl)-7-ethyl-8-oxamoylpyrrolo [1,2-a]pyrazin-1-yl]oxyacetic acid,
[6-Benzyl-7-ethyl-3-methyl-8-oxamoylpyrrolo[1,2-a]pyrazin-1-yl]oxyacetic acid,
[7-Ethyl-6-(4-fluorobenzyl)-3-methyl-8-oxamoylpyrrolo [1,2-a]pyrazin-1-yl]oxyacetic acid,
[6-(2-Biphenylmethyl)-7-ethyl-3-methyl-8-oxamoylpyrrolo [1,2-a]pyrazin-1-yl]oxyacetic acid,
[6-Cyclopentylmethyl-7-ethyl-3-methyl-8-oxamoylpyrrolo [1,2-a]pyrazin-1-yl]oxyacetic acid,
[6-(2-Benzyl)benzyl-7-ethyl-3-methyl-8-oxamoylpyrrolo [1,2-a]pyrazin- 1 -yl]oxyacetic acid,
[7-Ethyl-6-(2-(4-fluorophenyl)benzyl)-3-methyl-8-oxamoylpyrrolo[1,2-a]pyrazin-1-yl]oxyacetic acid,
[7-Ethyl-6-(3-fluorobenzyl)-3-methyl-8-oxamoylpyrrolo [1,2-a]pyrazin-1 -yl]oxyacetic acid,
[6-Benzyl-7-ethyl-3-isopropyl-8-oxamoylpyrrolo [1,2-a]pyrazin- 1-yl]oxyacetic acid,
[6-Benzyl-3,7-diethyl-8-oxamoylpyrrolo [1,2-a]pyrazin-1-yloxyacetic acid,
[6-Benzyl-7-ethyl-8-oxamoyl-3-phenylpyrrolo[1,2-a]pyrazin-1-yl]oxyacetic acid,
[6-Benzyl-7-ethyl-3-isobutyl-8-oxamoylpyrrolo[1,2-a]pyrazin-1-yl]oxyacetic acid,
[3,6-Dibenzyl-7-ethyl-8-oxamoylpyrrolo[1,2-a]pyrazin-1-yl]oxyacetic acid,
[7-Ethyl-3-methyl-8-oxamoyl-6-(2-(2-thienyl)benzyl) pyrrolo[1,2-a]pyrazin- 1 -yl]oxyacetic acid,
[7-Ethyl-3-methyl-8-oxamoyl-6-(2-phenylethynylbenzyl) pyrrolo [1,2-a]pyrazin- 1-yl]oxyacetic acid,
[7-Ethyl-3-methyl-8-oxamoyl-6-(2-phenyloxybenzyl) pyrrolo [1,2-a]pyrazin-1-yl]oxyacetic acid,
[7-Ethyl-3-methyl-8-oxamoyl-6-(2-(3-thienyl)benzyl) pyrrolo [1,2-a]pyrazin- 1 -yl]oxyacetic acid,
[7-Ethyl-3-methyl-6-(2-(5-methylthien-2-yl)benzyl)-8-oxamoylpyrrolo[1,2-a]pyrazin-1-yl]oxyacetic acid,
[7-Ethyl-6-(2-(4-methoxyphenyl)benzyl)-3-methyl-8-oxamoylpyrrolo [1,2-a]pyrazin-1-yl ]oxyacetic acid,
[7-Ethyl-3-methyl-6-(2-(4-methylphenyl)benzyl)-8-oxamoylpyrrolo[ 1,2-a]pyrazin- 1-yl]oxyacetic acid,
[7-Ethyl-3-methyl-8-oxamoyl-6-(2-(2-phenylethyl)benzyl) pyrrolo[1,2-a]pyrazin- 1 -yl]oxyacetic acid,
[6-Benzyl-7-cyclopropyl-3-methyl-8-oxamoylpyrrolo[1,2-a]pyrazin- 1 -ylloxyacetic acid,
[7—Cyclopropyl-6-(4-fluorobenzyl)-3-methyl-8-oxamoylpyrrolo[1,2-a]pyrazin- 1 -yl]oxyacetic acid,
[6-Benzyl-3-cyclohexyl-7-ethyl-8-oxamoylpyrrolo[1,2-a] pyrazin-1 -yl]oxyacetic acid,
[6-(2-Biphenylmethyl)-3-cyclohexyl-7-ethyl-8-oxamoylpyrrolo[1,2-a]pyrazin- 1-yl]oxyacetic acid,
[6-Benzyl-3,7-dimethyl-8-oxamoylpyrrolo [ 1,2-a]pyrazin-1-ylloxyacetic acid,
[7-Ethyl-3-methyl-6-(5-methylthien-2-ylmethyl)-8-oxamoylpyrrolo[1,2-a]pyrazin-1-yl ]oxyacetic acid,
[6-(Benzo[b]thiophen-3-ylmethyl)-7-ethyl-3-methyl-8-oxamoylpyrrolo [1,2-a]pyrazin- 1-yl ]oxyacetic acid,
Sodium [7-ethyl-6-(4-fluorobenzyl)-3-methyl-8-oxamoylpyrrolo [1,2-a]pyrazin-1-yl]oxyacetate,
Sodium [7-ethyl-6-(2-(4-fluorophenyl)benzyl)-3-methyl-8-oxamoylpyrrolo[1,2-a]pyrazin-1 -yl]oxyacetate,
Sodium [7-ethyl-3-methyl-8-oxamoyl-6-(2-(2-thienyl) benzyl)pyrrolo[1,2-a]pyrazin-1-yl ]oxyacetate,
Sodium [7-ethyl-3-methyl-8-oxamoyl-6-(2-(3-thienyl) benzyl)pyrrolo [1,2-a]pyrazin-1-yl ]oxyacetate,
and the prodrugs thereof; the parent acids thereof, or their pharmaceutically acceptable salts; or their solvates.

Most preferred as sPLA$_2$ inhibitors of the invention are
Methyl[7-ethyl-6-(2-(4-fluorophenyl)benzyl)-3-methyl-8-oxamoylpyrrolo [1,2-a]pyrazin-1 -yl]oxyacetate,
Ethyl[7-ethyl-6-(2-(4-fluorophenyl)benzyl)-3-methyl-8-oxamoylpyrrolo[1,2-a]pyrazin-1-yl]oxyacetate,
Morpholinylethyl [7-ethyl-6-(2-(4-fluorophenyl)benzyl)-3-methyl-8-oxamoylpyrrolo[1,2-a ]pyrazin-1-yl]oxyacetate,
Sodium[7-ethyl-6-(2-(4-fluorophenyl)benzyl)-3-methyl-8-oxamoylpyrrolo[1,2-a]pyrazin-1 -y)oxyacetate,
Methyl[7-ethyl-3-methyl-8-oxamoyl-6-(2-(2-thienyl) benzyl)pyrrolo[1,2-a]pyrazin-1-yl ]oxyacetate, Ethyl [7-ethyl-3-methyl-8-oxamoyl-6-(2-(2-thienyl)benzyl) pyrrolo[1,2-a]pyrazin-1-yl ]oxyacetate,
Morpholinylethyl [7-ethyl-3-methyl-8-oxamoyl-6-(2-(2-thienyl)benzyl)pyrrolo[1,2-a]pyrazin-1-yl]oxyacetate, and
Sodium [7-ethyl-3-methyl-8-oxamoyl-6-(2-(2-thienyl) benzyl)pyrrolo[1,2-a]pyrazin- 1-yl ]oxyacetate.

The invention also relates to a pharmaceutical composition containing as active ingredient a compound as described in any one of formula (I) or (II) or (III) or (IV) supra., or as named, supra., or as tabulated in Tables 14 to 25, infra., or as described in any one of the Examples, infra.

The invention further relates to a pharmaceutical composition as described in the preceding paragraph, which is for inhibiting sPLA$_2$.

The invention also relates to a pharmaceutical composition as described in the preceding paragraph, which is for treatment or prevention of Inflammatory Diseases.

The invention further is also a method of inhibiting sPLA$_2$ mediated release of fatty acid which comprises contacting sPLA$_2$ with a therapeutically effective amount of a pyrrolo[1,2-a]pyrazine compound.

The invention is also a method of treating a mammal, including a human, to alleviate the pathological effects of Inflammatory Diseases; wherein the method comprises administration to said mammal of a pyrrolo[1,2-a]pyrazine compound.

The invention further relates to a pyrrolo[1,2-a]pyrazine compound of described in any one of formula (I) or (II) or (III) or (IV) supra., or as named, supra., or as tabulated in Tables 14 to 25, infra., or as described in any one of the Examples, infra, or a pharmaceutical formulation containing an effective amount of said compound for use in treatment of Inflammatory Diseases.

The invention also relates to a compound or formulation as described in the preceding paragraph containing an effective amount of a pyrrolo[1,2-a]pyrazine compound for use as an inhibitor for inhibiting sPLA$_2$ mediated release of fatty acid.

The invention further relates to a pyrrolo[1,2-a]pyrazine sPLA$_2$ inhibitor substantially as hereinbefore described with reference to any of the Examples.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooctyl); cycloalkenyl (such as cyclobutylenyl, cyclopentenyl, cyclohexenyl, cycloheptenyl, and cyclooptenyl); phenyl, spiro[5,5]undecanyl, naphthyl, norbornyl, bicycloheptadienyl, tolyl, xylyl, indenyl, stilbenyl, terphenylyl, diphenylethylenyl, phenylcyclohexenyl, acenaphthyl, anthoryl, biphenylyl, bibenzylyl, and a phenylalkylphenyl derivative represented by the formula:

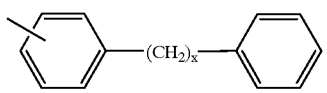

(V)

wherein x is an integer from 1 to 8.

The term "spiro[5,5]undecanyl" refers to the group represented by the formula:

Phenyl, cyclohexyl or the like is preferred as a carbocyclic groups in the R$^4$ and R$^5$.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrroly], pyrrolidinyl, piperidinyl, furyl, benzofuryl, thienyl, benzothienyl, pyrazolyl, imidazolyl, phenylimidazolyl, triazolyl, isoxazolyl oxazolyl, thiazolyl, thiadiazolyl, indolyl, carbazolyl, norharmanyl azaindolyl, benzofuranyl, benzothiophenyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and the like.

Furyl, thienyl or the like is preferred as a heterocyclic group in the R$^4$ and R$^5$.

Preferred carbocyclic and heterocyclic groups in R$^1$ are (g) a group represented by the formula:

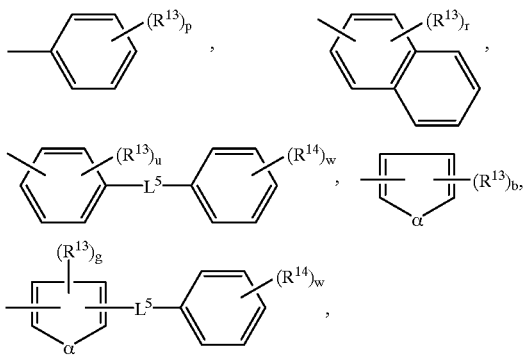

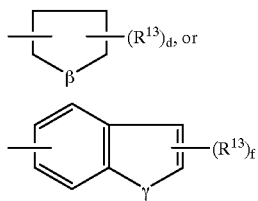

wherein $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl, a is an oxygen atom or a sulfur atom, $L^5$ is —$(CH_2)v$—, —C=C—, —C≡C—, —O—, or —S—, v is an integer from 0 to 2; α is an oxygen atom or a sulfur atom; β is —$CH_2$— or —$(CH_2)_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4. When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group. A more preferable example includes (h) a group represented by the formula:

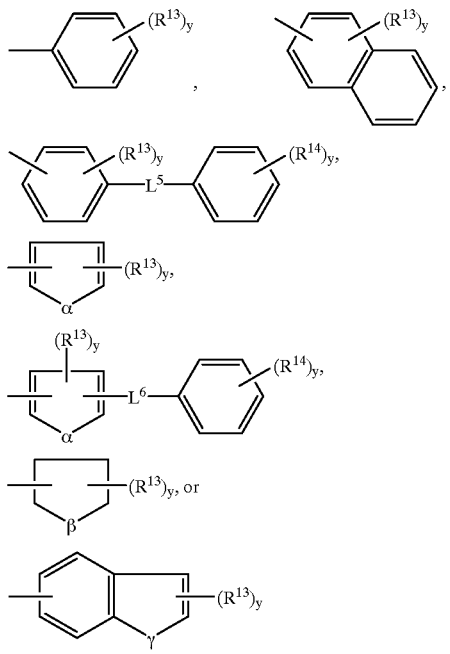

wherein $R^{13}$, $R^{14}$, α, β; and γ are the same as defined above, $L^6$ is a bond, —$CH_2$—, —C=C—, —C≡C—, —O—, or —S— and γ is 0 or 1. When $R^{13}$ is a substituent on the naphthyl group, the substituent may be substituted at any arbitrary position on the naphthyl group.

The "pyrrolo[1,2-a]pyrazine nucleus" is represented by the following structural formula together its numerical ring position for substituent placement:

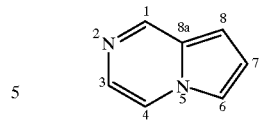

The term "non-interfering substituent" in the present specification means a group suitable for substitution at position 3 and 4 on the pyrrolo[1,2-a]pyrazine nucleus represented by the formula (I) as well as a group suitable for substitution of the above described "carbocyclic group" and "heterocyclic group". An example of the non-interfering substituents includes C1 to C8 alkyl, C2 to C8 alkenyl, C2 to C8 alkynyl, C7 to C12 aralkyl (such as benzyl and phenethyl), C7 to C12 alkaryl, C2 to C8 alkenyloxy, C2 to C8 alkynyloxy, C3 to C8 cycloalkyl, C3 to C8 cycloalkenyl, phenyl, tolyl, xylyl, biphenylyl, C1 to C8 alkyloxy, C2 to C12 alkyloxyalkyl (such as methyloxymethyl, ethyloxymethyl, methyloxyethyl, and ethyloxyethyl), C2 to C12 alkyloxyalkyloxy (such as methyloxymethyloxy and methyloxyethyloxy), C2 to C12 alkylcarbonyl (such as methylcarbonyl and ethylcarbonyl), C2 to C12 alkylcarbonylamino (such as methylcarbonylamino and ethylcarbonylamino), C2 to C12 alkyloxyamino (such as methyloxyamino and ethyloxyamino), C2 to C12 alkyloxyaminocarbonyl (such as methyloxyaminocarbonyl and ethyloxyaminocarbonyl), C1 to C12 alkylamino (such as methylamino, ethylamino, dimethylamino, and ethylmethylamino), C1 to C6 alkylthio, C2 to C12 alkylthiocarbonyl (such as methylthiocarbonyl and ethylthiocarbonyl), C1 to C8 alkylsulfinyl (such as methylsulfinyl and ethylsulfinyl), C1 to C8 alkylsulfonyl (such as methylsulfonyl and ethylsulfonyl), C2 to C8 haloalkyloxy (such as 2-chloroethyloxy and 2-bromoethyloxy), C1 to C8 haloalkylsulfonyl (such as chloromethylsulfonyl and bromomethylsulfonyl), C2 to C8 haloalkyl, C1 to C8 hydroxyalkyl (such as hydroxymethyl and hydroxyethyl), —C(O)O(C1 to C8 alkyl) (such as methyloxycarbonyl and ethyloxycarbonyl, —$(CH_2)z$—O—(C1 to C8 alkyl), benzyloxy, aryloxy (such as phenyloxy), arylthio (such as phenylthio), —$(CONHSO_2R^{25})$, —CHO, amino, amidino, halogen, carbamyl, carboxyl, carbalkyloxy, —$(CH_2)z$—COOH (such as carboxymethyl, carboxyethyl, and carboxypropyl), cyano, cyanoguanidino, guanidino, hydrazido, hydrazino, hydroxy, hydroxyamino, nitro, phosphono, —$SO_3H$, thioacetal thiocarbonyl, carbonyl, carbocyclic groups, heterocyclic groups and the like wherein z is an integer from 1 to 8 and $R^{25}$ is C1 to C6 alkyl or aryl. These groups may be substituted by at least one substituent selected from the group consisting of C1 to C6 alkyl, C1 to C6 alkyloxy, C2 to C6 haloalkyloxy, C1 to C6 haloalkyl, and halogens.

Preferable are halogens, C1 to C6 alkyl, C1 to C6 alkyloxy, C1 to C6 alkylthio, and C1 to C6 haloalkyl as the "non-interfering substituent" in the $R^1$. More preferable are halogens, C1 to C3 alkyl, C1 to C3 alkyloxy, C1 to C3 alkylthio, and C1 to C3 haloalkyl.

Preferable are (i) C1 to C6 alkyl, aralkyl, C1 to C6 alkyloxy, C1 to C6 alkylthio, C1 to C6 hydroxyalkyl, C2 to C6 haloalkyloxy, halogens, carboxy, C1 to C6 alkyloxycarbonyl, aryloxy, arylthio, carbocyclic groups, and heterocyclic groups as the "non-interfering substituents" in the $R^4$, $R^5$, $R^{10}$, and $R^{11}$. More preferable are (0) C1 to C6 alkyl, aralkyl, carboxy, C1 to C6 hydroxyalkyl, phenyl, and C1 to C6 alkyloxycarbonyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cydlopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a pyrrolo[1,2-a]pyrazine nucleus through a suitable linking atom (hereinafter defined as "acid linker"). An example of the acidic group includes (k) a group represented by the formula:

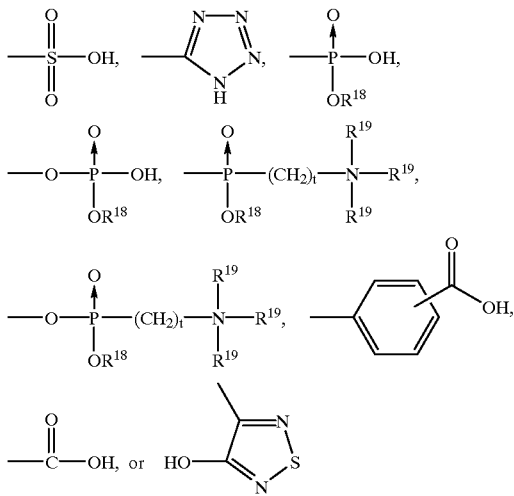

wherein $R^{18}$ is hydrogen atom, a metal, or C1 to C10 alkyl and each $R^{19}$ is independently hydrogen atom or C1 to C10 alkyl. Preferable is (1) —COOH, —SO$_3$H, or P(O)(OH)$_2$. More preferable is (m)—COOH.

The term "acid linker" in the present specification means a divalent linking group represented by a symbol —(L$^2$)—, and it functions to join 1-position of pyrrolo[1,2-a]pyrazine nucleus to an "acidic group" in the general relationship. An example of it includes (n) a group represented by the formula:

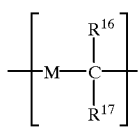

wherein M is —CH$_2$—, —O—, —N(R$^{24}$)—, or —S—, and $R^{16}$ and $R^{17}$ are independently hydrogen atom, C1 to C10 alkyL aryl, aralkyl, carboxy, or halogens. Preferable are (o) —O—CH$_2$—, —S—CH$_2$—, —N(R$^{24}$)—CH$_2$—, —CH$_2$—CH$_2$—, —O—CH(CH$_3$)—, or —O—CH((CH$_2$)$_2$Ph)— wherein $R^{24}$ is hydrogen atom or C1 to C6 alkyl and Ph is phenyl. More preferable is (o) —O—CH$_2$— or —S—CH$_2$—.

In the present specification, the term "acid linker length" means the number of atoms (except for hydrogen atoms) in the shortest chain of a linking group —(L$^2$)—which connects 1-position in pyrrolo[1,2-a]pyrazine nucleus with the "acidic group". The presence of a carbocyclic ring in —(L$^2$)—counts as the number of atoms approximately equivalent to the calculated diameter of the carbocyclic ring. Thus, a benzene and cyclohexane ring in the acid linker counts as two atoms in culculating the length of —(L$^2$)—. A preferable length is 2 to 3.

A symbol k in the formula (IV) is preferably 1.

The term "haloalkyl" in the present specification means the above described "alkyl" substituted with the above described "halo(gen" at arbitrary position(s). An example of the halo alkyl includes chloro methyl, trifluoro methyl, 2-chloroethyl, 2-bromoethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2,2,2-tritluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl, and 1-naphthyl are preferred.

The term "aralkyl" in the present specification means a group wherein the aforementioned "alkyl" is substituted with the above-mentioned "aryl". Such aryl may have a bond at any substitutable position . An example of it includes benzyl, phenethyl, phenylpropyl (such as 3-phenylpropyl), naphthylmethyl (such as 1-naphthylmethyl) and the like.

The term, "group containing 1 to 4 non-hydrogen atoms" refers to relatively small groups which form substituents at the 7 position of the pyrrolo[1,2-a]pyrazine nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO, —CN, —SO$_3$; and (ii) groups having hydrogen atoms which contain less than 4 non-hydrogen atoms such as —CH$_3$, —C$_2$H$_5$, —CH=CH$_2$, —CH(CH$_3$)$_2$,and cyclopropyl.

An example of the "alkyloxycarbonyl" in the present specification includes methyloxycarbonyl, ethyloxycarbonyl, n-propyloxycarbonyl and the like.

A group of preferable substituents as the R$^1$ to R$^5$ and the R$^A$ of the compound represented by the formula (I) will be shown in items (A) to (W). Items (f) to (m) are the same group as described above.

As the R$^1$, (A): —(L$^1$)—R$^6$, (B): —(CH$_2$)$_{1-2}$—(g), (C): —(CH$_2$)$_{,2}$—(g), and (D): —(CH,)$_{1-2}$—(h) are preferred.

As the R$^2$, (E): hydrogen atom, halogen, C1 to C3 alkyl, C3 to C4 cycloalkyl, or C1 to C3 alkyloxy; and (F): C1 to C3 alkyl or C3 to C4 cycloalkyl are preferred.

As the R$^A$, (G): —C(=O)—C(=O)—NH$_2$, —CH$_2$C(=O)—NH$_2$, or —CH$_2$C(=O) —NHNH$_2$; and (H): —C(=O)—C(=O)—NH$_2$ are preferred.

As the R$^3$, (I): —(n)—(k), (J): —(n)—(l), (K): —(n)—(m), (L): —(o)—(k), (M): —(o)—(l), (N): —(o)—(m), (O): —(p)—(k), (P): —(p)—(l), and (Q): —(p)—(m) are preferred.

As the $R^4$, (R): hydrogen atom or non-interfering substituent, (S): hydrogen atom or (i), and (T): hydrogen atom or 0) are preferred.

As the $R^5$, (U): hydrogen atom or (i), (V): hydrogen atom or (j), and (W): hydrogen atom are preferred.

A preferred group of compounds represented by the formula (I) will be shown hereinafter.

$(R^1,R^2,R^A,R^4,R^5)$=(A,E,G,R,U), (A,E,G,R,V), (A,E,G,R,W), (AE,G,S,U), (A,E,G,S,V),
(A,E,G,S,W), (A,E,G,T,U), (A,E,G,T,V), (A,E,G,T,W), (A,E,H,R,U), (A,E,H,R,V),
(A,E,H,R,W), (A,E,H,S,U), (A,E,H,S,V), (A,E,H,S,W), (A,E,H,T,U), (AE,H,T,V),
(A,E,H,T,W), (A,F,G,R,U), (AF,G,R,V), (AF,G,R,W), (A,F,G,S,U), (A,F,G,S,V),
(A,F,G,S,W), (A,F,G,T,U), (A,F,G,T,V), (AF,G,T,W), (A,F,H,R,U), (A,F,H,R,V),
(A,F,H,R,W), (A,F,H,S,U), (AF,H,S,V), (AF,H,S,W), (AF,H,T,U), (A,F,H,T,V),
(A,F,H,T,W), (B,E,G,R,U), (B,E,G,R,V), (B,E,G,R,W), (B,E,G,S,U), (B,E,G,S,V),
(B,E,G,S,W), (B,E,G,T,U), (B,E,G,T,V), (B,E,G,T,W), (B,E,H,R,U), (B,E,H,R,V),
(B,E,H,R,W), (B,E,H,S,U), (B,E,H,S,V), (B,E,H,S,W), (B,E,H,T,U), (B,E,H,T,V),
(B,E,H,T,W), (B,F,G,R,U), (B,F,G,R,V), (B,F,G,R,W), (B,F,G,S,U), (B,F,G,S,V),
(B,F,G,S,W), (B,F,G,T,U), (B,F,G,T,V), (B,F,G,T,W), (B,F,H,R,U), (B,F,H,R,V),
(B,F,H,R,W), (B,F,H,S,U), (B,F,H,S,V), (B,F,H,S,W), (B,F,H,T,U), (B,F,H,T,V).
(B ,F,H,T,W), (C,E,G,R,U), (C,E,G,R,V), (C,E,G,R,W), (C,E,G,S,U), (C,E,G,S,V),
(C,E,G,S,W), (C,E,G,T,U), (C,E,G,T,V), (C,E,G,T,W), (C,E,H,R,U), (C,E,H,R,V),
(C,E,H,R,W, (C,E,H,S,U), (C,E,H,S,V), (C,E,H,S,W), (C,E,H,T,U), (C,E,H,T,V),
(C,E,H,T,W), (C,F,G,R,U), (C,F,G,R,V), (C,F,G,R,W), (C,F,G,S,U), (C,F,G,S,V),
(C,F,G,S,W), (C,F,G,T,U), (C,F,G,T,V), (C,F,G,T,W), (C,F,H,R,U), (C,F,H,R,V),
(C,F,H,R,W), (C,F,H,S,U), (C,F,H,S,V), (C,F,H,S,W), (C,F,H,T,U), (C,F,H,T,V),
(C,F,H,T,W), (D,E,G,R,U), (D,E,G,R,V), (D,E,G,R,W), (D,E,G,S,U), (D,E,G,S,V),
(D,E,G,S,W), (D,E,G,T,U), (D,E,G,T,V), (D,E,G,T,W), (D,E,H,R,U), (D,E,H,R,V),
(D,E,H,R,W), (D,E,H,S,U), (D,E,H,S,V), (D,E,H,S,W), (D,E,H,T,U), (D,E,H,T,V),
(D,E,H,T,W), (D,F,G,R,U), (D,F,G,R,V), (D,F,G,R,W), (D,F,G,S,U), (D,F,G,S,V),
(D,F,G,S,W), (D,F,G,T,U), (D,F,G,T,V), (D,F,G,T, W), (D,F,H,R,U), (D,F,H,R,V),
(D,F,H,R,W), (D,F,H,S,U), (D,F,H,S,V), (D,F,H,S,W), (D,F,H,T,U), (D,F,H,T,V), and
(D,F,H,T,W).

Preferred embodiments of this invention are compounds wherein $R^3$ is any one of (I) to (Q) and $(R^1,R^2,R^A,R^4,R^5)$ is any one of the above combinations.

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, chronic rheumatism, arterial sclerosis, cereberal hemorrhage, cerebral infarction, cardiac failure, cardiac infarction, psoriasis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo out, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The terms, "mammal" and "mammalian" include human.

The term "solvate" includes, for example, solvates with organic solvents, hydrates, and the like.

The compounds of the invention represented by the general formula (I) can be synthesized in accordance with the following methods A to I.

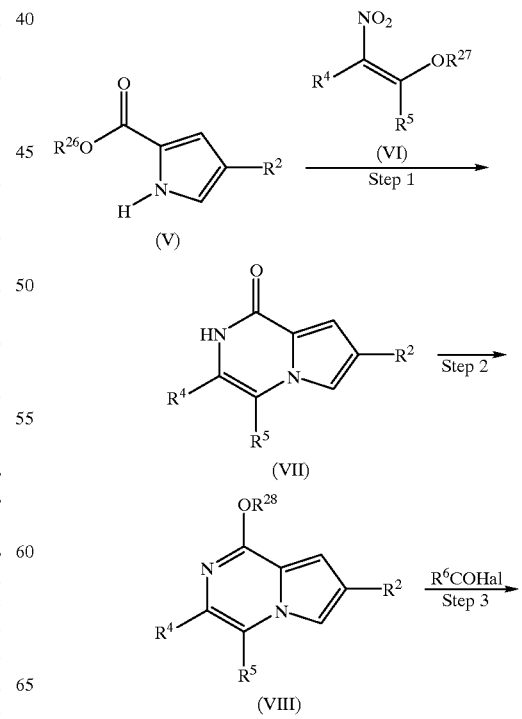

(Method A)

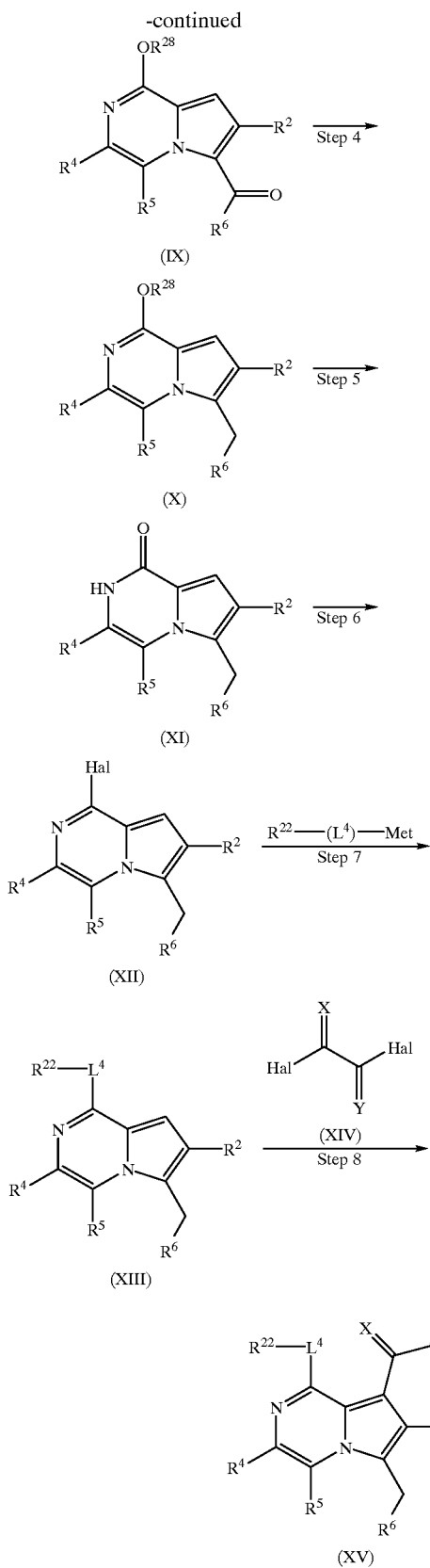

wherein $R^2$, $R^4$, $R^5$, $R^6$, $R^{22}$, X, Y, and $L^4$ are as defined above; $R^{26}$ $R^{27}$, and $R^{28}$ are C1 to C3 alkyl; Hal is a halogen, and Met is an alkali metal.

(Step 1)

The present step is the one for constructing pyrrolo[1,2-a]pyrazine ring, and it may be conducted in accordance with a process described in J. Chem. Soc., Perkin Trans. 1, 1990, 311–314 (The disclosure of which are incorporated herein by reference).

(Step 2)

The present step is the one for transforming the ketone at 1-position into an alkyloxy group. To the compound (VII) is added a halogenating agent such as phosphorus oxychloride, phenylphosphonic dichloride and the like, and the resulting mixture is refluxed for 1 to 8 hours, preferably 3 to 5 hours. The resulting compound is dissolved in an alcohol (for example, methanol, ethanol, and n-propanol), an alkali metal compound of C1 to C3 alcohol (for example, sodium methoxide, and sodium ethoxide), sodium p-toluenesulfinate and the like are added to the solution, and the mixture is stirred at 70° C. to 120° C., preferably 80° C. to 100° C. for 5 to 36 hours, preferably 12 to 24 hours. When the resulting product is subjected to a usual work-up, the compound (VIII) can be obtained.

(Step 3)

The present step is the one for introducing a substituent to 6-position of pyrrolo[1,2-a]pyrazine, and it may be carried out by Friedel—Crafts reaction. The compound (VIII) is dissolved in a solvent such as 1,2-dichloroethane, methylene chloride and the like, $R^6COHal$ and Lewis acid (for example, $AlCl_3$, $SbF_5$, $BF_3$ and the like) are added gradually to the solution at −78° C. to 10° C., preferably −20° C. to ice-cooling, and the resulting mixture is stirred at −10° C. to 10° C., preferably 0° C. to 10° C. for 5 to 30 minutes, preferably 10 to 20 minutes. Alternatively, the reaction may be carried out in such that the compound (VIII) is dissolved in $R^6COHal$ without using any solvents, and then, the step is continued in accordance with the same manner as that described above. When the resulting product is subjected to a usual work-up, the compound (IX) can be obtained (see J. Med. Chem., 39, 3636–58 (1996). The disclosure of which are incorporated herein by reference.)

(Step 4)

The present step is the one for reducing the carbonyl group at 6-position of pyrrolo[1,2-a]pyrazine to transform the same into methylene. Lewis acid (for example, $AlCl_3$ and the like) is dissolved in a solvent such as methylene chloride, tetrahydrofuran and the like, a reducing agent such as boron-t-butylamine complex, sodium borohydride and the like is added to the solution at −20° C. to 10° C., preferably under ice-cooling, and the resulting mixture is stirred for 5 to 30 minutes, preferably 10 to 20 minutes. The compound (IX) dissolved in methylene chloride, tetrahydrofuran and the like is added to the reaction mixture at −20° C. to 10° C., preferably under ice-cooling, the resulting mixture is stirred preferably for 20 to 30 minutes, and further the stir is continued at 15° C. to 40° C., preferably 20° C. to 30° C. for 1 to 5 hours, preferably 2 to 3 hours. When the resulting product is subjected to a usual work-up, the compound (X) can be obtained (see J. Med. Chem., 39, 3635–58 (1996). It is to be noted that The disclosure of which are incorporated herein by reference.)

(Step 5)

The present step is the one for transforming the alkyloxy group into ketone. An acid such as concentrated hydrochloric acid and the like is added to the compound (X), and the mixture is stirred at 80° C. to 150° C., preferably 100° C. to 120° C. for 1 to 5 hours preferably 2 to 3 hours. When the resulting product is subjected to a usual work-up, the compound (XI) can be obtained.

(Step 6)

The present step is the one for transforming the ketone at 1-position into a halogen. A halogenating agent such as phosphorus oxychloride, phenylphosphonic dichloride and the like is added to the compound (XI), and the mixture is refluxed for 1 to 8 hours, preferably 3 to 5 hours. When the resulting product is subjected to an ordinary work-up, the compound (XII) can be obtained.

(Step 7)

The present step is the one for transforming the halogen at 1-position into (—$L^4$—$R^{22}$). To a suspension of $R^{22}$—$L^4$—H and an alkali metal compound such as sodium and the like are added the compound (XII) and sodium p-toluenesulfinate or the like, and the mixture is stirred at 70° C. to 120° C., preferably 80° C. to 100° C. for 5 to 36 hours, preferably 12 to 24 hours. When the resulting product is subjected to an ordinary work-up, the compound (XIII) can be obtained.

(Step 8)

The present step is the one for introducing a substituent to 8-position. The compound (XIII) is dissolved in a solvent such as 1,2-dichloroethane, tetrahydrofuran and the like, Hal—C(=X)—C(=X)—Hal (for example, oxalyl chloride) and a base such as N-methylmorpholine, triethylamine and the like are added to the solution, and the mixture is stirred at 30° C. to 70° C., preferably 40° C. to 60° C. for 1 to 10 hours, preferably 3 to 6 hours. The reaction mixture is poured into cold aqueous ammonia, and the resulting mixture is stirred for 5 to 30 minutes, preferably 10 to 20 minutes. When the resulting product is subjected to an ordinary work-up, the compound (XV) can be obtained.

(Method B)

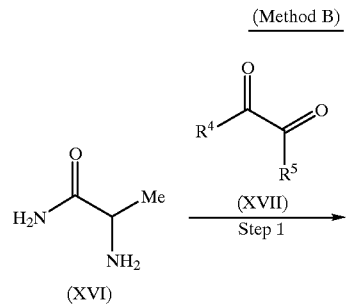

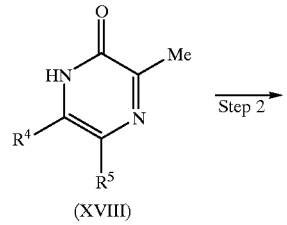

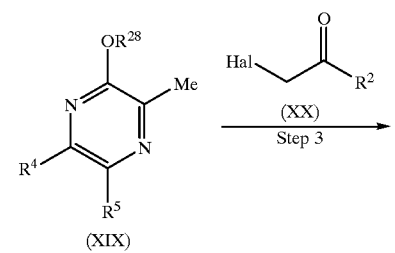

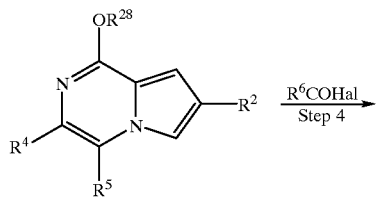

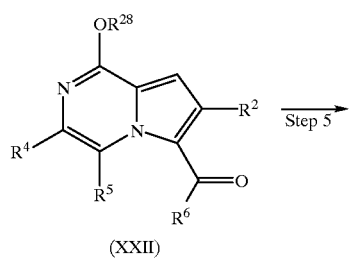

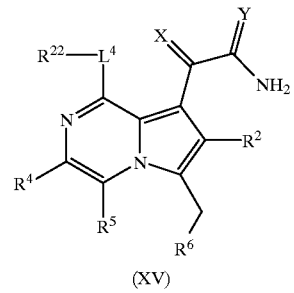

wherein $R^2$, $R^4$, $R^6$, $R^{22}$, R28, $L^4$, X, Y, and Hal are as defined above, and $R^5$ is hydrogen.

(Step 1)

The present step is the one for constructing pyrazine ring, and it may be carried out in accordance with the process described in J. Am. Chem. Soc., 74, 1580–84 (1952). (The disclosure of which are incorporated herein by reference.)

(Step 2)

The present step may be carried out in accordance with the same manner as that of the method A—step 2.

(Step 3)

The present step is the one for constructing pyrrolo[1,2-a]pyrazine ring. A mixture of the compound (XIX) and Hal—$CH_2$—C(=O)—$R^2$ is stirred at 40° C. to 90° C., preferably 50° C to 70° C. for 3 to 36 hours, preferably 12 to 24 hours to obtain a quaternary salt. The resulting quaternary salt is dissolved in a solvent such as 1,2-dichloroethane, acetonitrile and the like, a base such as 1,8-diazabicyclo[5,4,0]-undec-7-ene(DBU), triethylamine and the like is added to the solution, and the mixture is stirred at 40° C. to 90° C., preferably 50° C. to 70° C. for 3 to 36 hours, preferably 12 to 24 hours. When the resulting product is subjected to a usual work-up, the compound (XXI) can be obtained.

(Step 4)

The present step may be carried out in accordance with the same manner as that of the method A—step 3.

(Step 5)

The present step may be carried out in accordance with the same manner as that of the method A—steps 4 to 8.

(Method C)

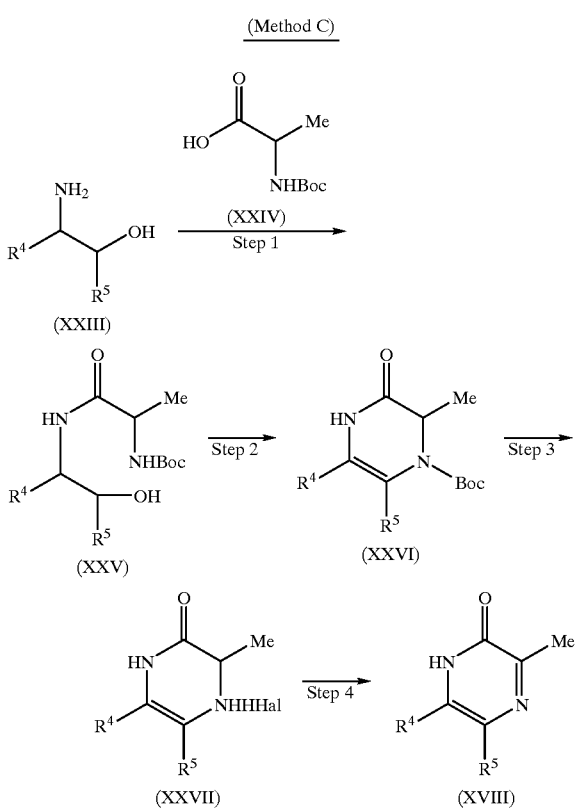

wherein $R^4$, $R^5$, and Hal are as defined above, and Boc is t-butoxycarbonyl.

(Step 1)

The present step is the one for conducting condensation reaction of the compound (XXIII) and the compound (XXIV). The compound (XXIII) is dissolved in a solvent such as tetrahydrofuran, dichloromethane, acetonitrile and the like, the compound (XXIV) and a condensation agent such as N,N-dicyclohexylcarbodiimide (DCC), 1-ethyl-3—(3-dimethylaminopropyl)carbodiimide (WSCD), N,N-dicarbonylimidazole, 2-halo-1-methylpyridinium iodide, di-2-pyridyl carbonate, 1,1'-oxalyldiimidazole and the like are added to the solution, and the resulting mixture is reacted at −20° C. to 80° C., preferably 0° C. to 40° C. for 1 to 30 hours, preferably 3 to 20 hours to obtain the compound (XXV).

(Step 2)

The present step is the one for effecting oxidation of hydroxyl group and ring closure reaction.

The oxidation reaction may be carried out in accordance with a manner applied generally. In this respect, the following four types of oxidation reaction are particularly preferred.

i) PCC Oxidation (The compound (XXV) is dissolved in a solvent such as dichloromethane and the like, pyridinium chlorochromate (PCC) is added to the solution, and the mixture is allowed to react at −20° C. to 60° C., preferably 0° C. to 40° C. for 1 to 30 hours, preferably 3 to 20 hours, to give an oxidized product.) (see Tetrahedron Lett., 2647–2650 (1975))

ii) Swern Oxidation (Dichloromethane is cooled to −78° C., oxalyl chloride, dimethyl sulfoxide, and the compound (XXV) are added successively to the solvent. The mixture is allowed to warm to −45° C. to 0° C., the mixture is allowed to react for 1 to 30 hours, preferably 1 to 10 hours. When the resulting product is subjected to a usual work-up, a aimed compound can be prepared.) (see J. Org. Chem., 43, 2480–2482 (1978))

iii) Dess-Martin Oxidation (A solution of Dess-Martin reagent in dimethyl sulfoxide or the like is allowed to react with compound (XXV) in a solvent such as tetrahydrofuran.) (see J. Org. Chem., 48, 4155–4156 (1983))

iv) Oxidation by Halogen Oxoacid (The compound (XXV) is allowed to react with an oxidizing agent such as halogen oxoacid and the like in the presence of 2,2,6,6-tetramethyl-1-piperizinyloxy (TEMPO) according to the process described in a literary document (J. Org. Chem., 52, 2559–2562 (1987)), whereby the compound can be prepared. In stead of TEMPO, 4-acetylamino-2,2,6,6-tetramethyl-1-piperidinyloxy, 4-benzoyloxy-2,2,6,6-tetramethyl-1-piperidinyloxy, 4-cyano-2,2,6,6-tetramethyl-1-piperidinyloxy or the like may be used. As the halogen oxoacid, sodium hypochlorite, sodium hypobromite, sodium bromite or the like is used. As the solvent, ethyl acetate, acetonitrile, dichloromethane or the like may be used.)

In ring closure reaction, the oxidized product prepared in accordance with the above step is dissolved in a solvent such as toluene, ethyl acetate, chloroform and the like, and the solution is allowed to react at −10° C. to 80° C., preferably 0° C. to 40° C. for 1 to 30 hours, preferably 5 to 20 hours, whereby the compound (XXVI) can be obtained. In the case where progress of the reaction is slow, it is sufficient to add a catalytic amount of a suitable acid (for example, p-toluenesulfonic acid and the like) to the solution.

(Step 3)

The present step is the one for deprotecting Boc group. The compound (XXVI) is dissolved in a solvent such as dichloromethane, ethyl acetate, toluene and the like, a mineral acid (for example, HCl, HBr, HI and the like) or an organic acid (for example, trifluoroacetic acid, camphorsulfonic acid and the like) is added to the solution, and the mixture is allowed to react at 0° C. to 100° C., preferably 20° C. to 100° C. for 1 to 20 hours, preferably 3 to 10 hours, whereby the compound (XXVII) can be prepared.

(Step 4)

The present step is the one for conducting dehydrogenation reaction. The compound (XXVII) is dissolved in a solvent such as decaline, quinoline, naphthalene and the like, Pd, Pt, Rh, Ni, S, or Se is added to the solution, and the mixture is allowed to react at 100° C. to 350° C. for 2 to 5 hours, whereby the compound (XVIII) can be obtained. In the case when a hydrogen receptor such as cyclohexene, maleic acid, and the like is allowed to exist in the reaction system, it is sufficient to be a reaction temperature of 100° C. to 150° C.

(Method D)

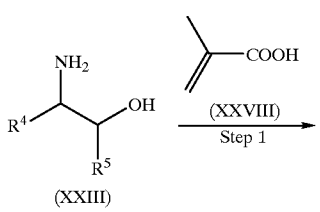

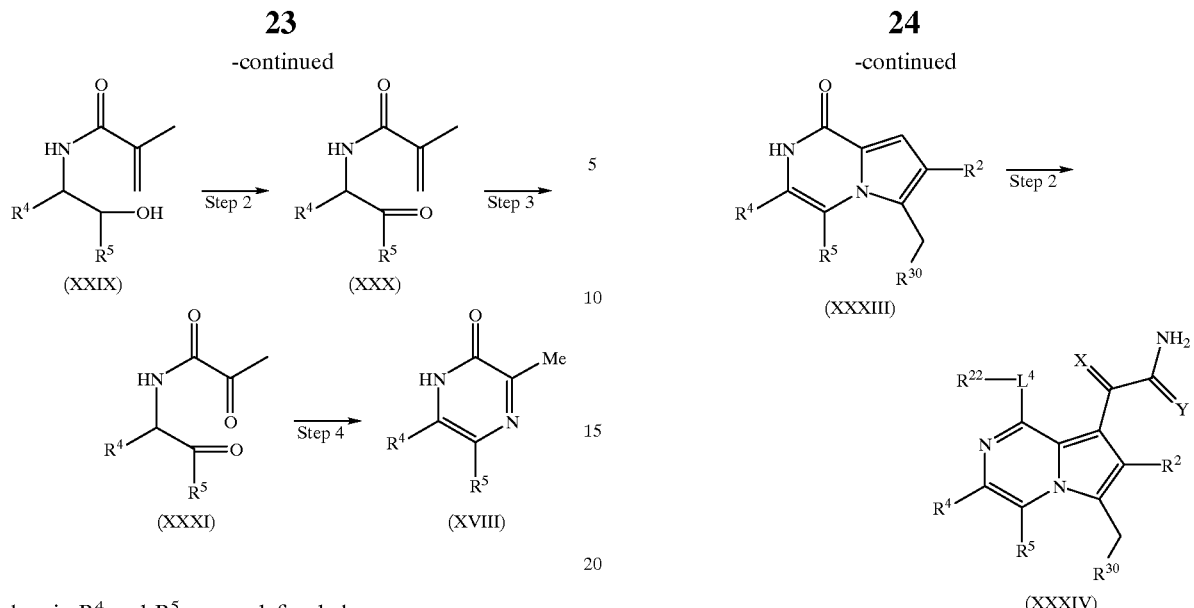

wherein $R^4$ and $R^5$ are as defined above.

(Step 1)

The present step may be carried out in accordance with the same manner as that of the method C—step 1.

(Step 2)

The present step may be carried out in accordance with the same manner as that of the oxidation step in the method C—step 2.

(Step 3)

The present step is the one for oxidizing methylene to form ketone. The compound (XXX) is dissolved in dichloromethane-methanol, ethyl acetate or the like, and ozone gas is bubbled through the solution at −78° C. to 0° C., preferably −78° C. to −30° C. After 5 minutes to 1 hour, dimethyl sulfide or triphenylphosphine is added to the resulting mixture, and the mixture is allowed to react at 0° C. to 60° C., preferably 10° C. to 40° C. for 1 to 2 hours, whereby the compound (XXXI) can be obtained.

(Step 4)

The present step is the one for effecting ring closure reaction. The compound (XXXI) is dissolved in a solvent such as ethanol and the like, ammonium acetate is added to the solution, and the mixture is refluxed for 5 minutes to 1 hour, whereby the compound (XVIII) can be prepared.

(Method E)

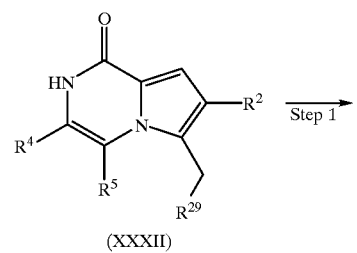

wherein $R^2$, $R^4$, $R^5$, $R^{22}$, $L^4$, X and Y are as defined above, $R^{29}$ is aryl or heteroaryl having a leaving group such as halogen, triilate, $R^{30}$ is aryl or heteroaryl substituted with aryl, heteroaryl, substituted vinyl, substituted acetylene, alkyl, aryloxy and the like.

(Step 1)

The present step is a step of a carbon-carbon bond forming reaction by Suzuki reaction or Sonogashira reaction using a palladium catalyst. By the present reaction, the compound (XXXII) is converted into the compound (XXXIII) in accordance with the methods described in Syn. Commun., 11, 513 (1981) (The disclosure of which are incorporated herein by reference), Tetrahedron Lett., 4467 (1975) (The disclosure of which are incorporated herein by reference) and the like.

Compound (XXXII) is reacted with optionally substituted aryl or optionally substituted heteroaryl having a $B(OH)_2$ (otherwise $B(Et)_2$) group such as phenylboronic acid in a solvent such as dimethylformamide, toluene, xylene, benzene, tetrahydrofuran etc. in the presence of a palladium catalyst (e.g., $Pd(Ph_3P)_4$) and a base (e.g., potassium carbonate, calcium carbonate, triethylamine, sodium methoxide etc.) to give the desired compound (XXXIII). This reaction is carried out at 0 to 100° C., preferably 0 to 80° C. This reaction is completed for 5 to 50 hours, preferably 15 to 30 hours. When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)) and then deprotected at an appropriate step.

Compound (XXXII) is reacted with optionally substituted aryl or optionally substituted heteroaryl having an ethynyl group such as ethynylbenzene in a solvent such as dimethylformamide, toluene, xylene, benzene, tetrahydrofuran etc. in the presence of a palladium catalyst (e.g., $Pd(Ph_3P)_2Cl_2$), a divalent copper reagent (e.g., CuI), and an organic base (e.g., triethylamine, and diisopropylethylamine) to give a desired compound (XXXIII). This reaction is carried out at 0 to 100° C., preferably 20 to 80° C. This reaction is completed for 3 to 30 hours, preferably 10 to 20 hours. When optionally substituted aryl or optionally substituted heteroaryl has a substituent(s) interfering this reaction, the substituent(s) can previously be protected in accordance with a method of "Protective Groups in Organic Synthesis" ( Theodora W. Green (John Wiley & Sons)), and then deprotected at an appropriate step.

In case that $R^{30}$ is aryl or heteroaryl substituted with aryloxy, the compound (XXXII) is dissolved in a solvent such as pyridine, and then cooper (II) oxide, a base (for example, potassium carbonate) and substituted phenols are added, and the resulting mixture was stirred at 10 to 150° C., preferably 100 to 150° C., for 1 to 24 hours, preferably 5 to 10 hours. The compound (XXXIII) is obtained by the usual work-up.

(Step 2)

The present step can be carried out in the same manner as those described in step 6 to 8 of Method A

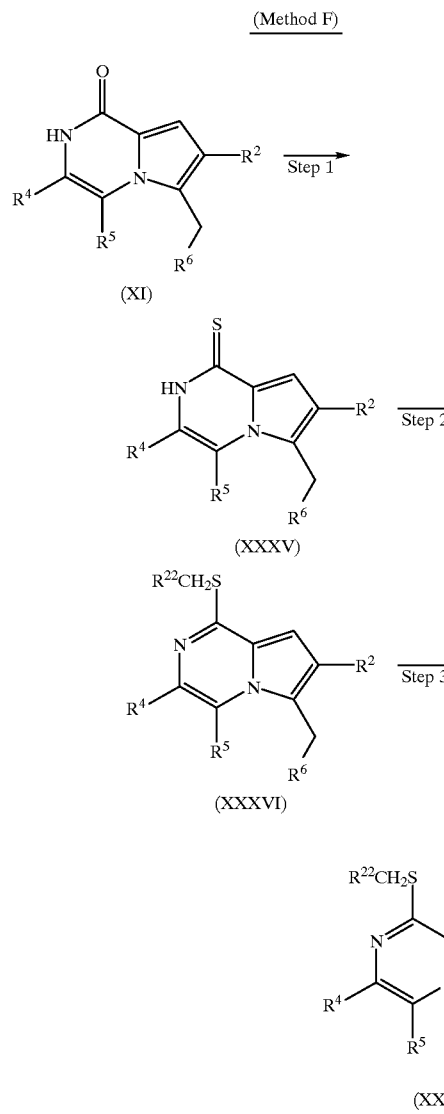

(Method F)

(XI)

(XXXV)

(XXXVI)

(XXXVII)

wherein $R^2$, $R^4$, $R^5$, $R^6$, $R^{22}$, X and Y are as defined above.

When $L^4$ is $CH_2S$ in Method A, (XXXVII) can also be synthesized by Method F.

(Step 1)

The present step is a step wherein the ketone group at C1-position is converted into thioketone. The reaction may be conducted in accordance with the method described in Monatsh chem, 126, 747 (1995) (The disclosure of which are incorporated herein by reference). The compound (XI) is dissolved in a solvent such as pyridine, and the resulting mixture is stirred with phosphorus pentasulfide at 10° C. to 150° C., preferably 100 to 150° C., for 1 to 5 hours, preferably 2 to 3 hours. The compound (XXXV) is obtained by the usual work-up. This step can also be conducted by reacting with compound (XI) and Lawesson reagent in a solvent such as tetrahydrofuran, dimethylformamide at 10 to 150° C., preferably 50 to 100° C., for 1 to 5 hours, preferably 2 to 3 hours.

(Step 2)

The present step is a step wherein the thioketone group at C1-position is converted into iminosulfide group.

The compound (XXXV) is dissolved in a solvent such as tetrahydrofuran, dimethylformamide, $R^{22}CH_2X$ (for example, bromoacetic acid methyl ester) and a base (for example, potassium carbonate) are added, and the resulting mixture is stirred at 0 to 100° C., preferably 10 to 50° C., for 1 to 5 hours, preferably 1 to 2 hours. The compound (XXXVI) is obtained by the usual work-up.

(Step 3)

The present step can be carried out in the same manner as that described in step 8 of Method A.

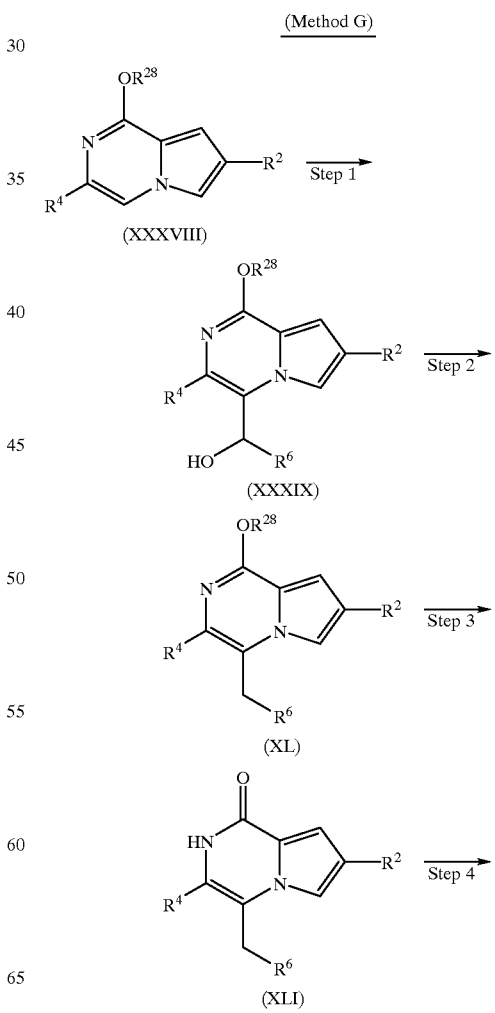

(Method G)

(XXXVIII)

(XXXIX)

(XL)

(XLI)

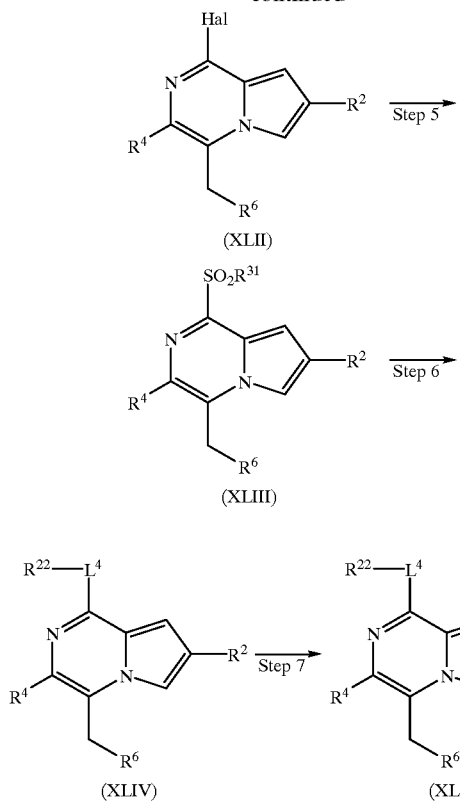

(Step 5)

The present step is a step wherein chloro group at C1-position of pyrrolo[1,2-a]pyrazine is converted to sulfonyl group. The compound (XLII) is dissolved in an alcoholic solvent such as ethanol or dimethyl sulfoxide, a sulfinate salt (for example, sodium p-toluenesulfinate) was added, and then the resulting mixture is stirred at 10 to 150° C., preferably 50 to 100° C., for 1 to 18 hours, preferably 3 to 8 hours. The catalytic amount of acid (for example, hydrochloric acid) may be added preferably. The compound (XLIII) is obtained by the usual work-up.

(Step 6)

The present step can be carried out in the same manner as that described in step 7 of Method A.

(Step 7)

The present step can be carried out in the same manner as that described in step 8 of Method A (Method H)

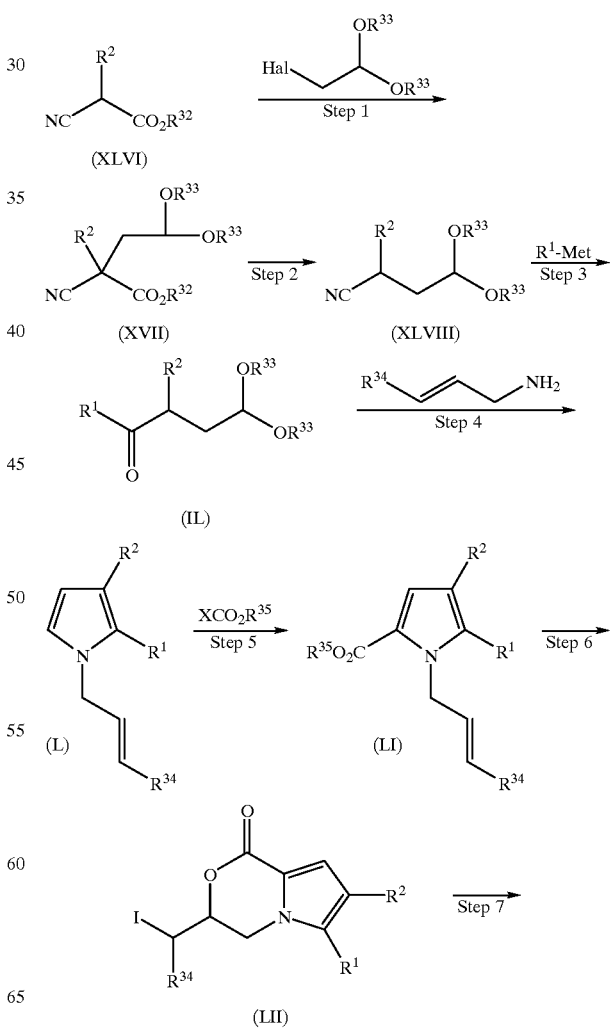

wherein $R^2$, $R^4$, $R^6$, $R^{22}$, $R^{28}$, $L^4$, Hal, X and Y are as defined above, $R^{31}L$ is C1–C3 alkyl or aryl.

(Step 1)

The present step is a step wherein a substituent is introduced to C4-position of pyrrolo[1,2-a]pyrazine without any substituent at C4-position. The compound (XXXVIII) is dissolved in a solvent such as diethyl ether, tetrahydrofuran, an alkyllithium (for example, methyllithium, n-butyllithium) was added at −78 to 10° C., preferably −30° C. to ice-cooling, and then the resulting mixture is stirred for 15 minutes to 1 hour, preferably 15 to 30 minutes. $R^6$—CHO is added to the above mixture and the mixture was stirred further 15 minutes to 1 hour, preferably 15 to 30 minutes. The compound (XXXIX) is obtained by the usual work-up.

(Step 2)

The present step is a step wherein the hydroxyl group at C4-position of pyrrolo[1,2-a]pyrazine is reduced, and converted into methylene group. The reaction can be conducted in accordance with the method described in Tetrahedron, 51, 11043 (1995) (The disclosure of which are incorporated herein by reference). Alternatively, the reaction may be conducted in accordance with the above step 4 of Method A, a catalytic hydrogenation method by using a reduction catalyst such as palladium-carbon and source of hydrogen such as hydrogen gas, ammonium formate (refer to Synth. Commun., 22, 2673 (1992), The disclosure of which are incorporated herein by reference), a method by using samarium iodide (refer to Tetrahedron Lett., 30, 2945 (1989), The disclosure of which are incorporated herein by reference) and the like.

(Step 3)

The present step can be carried out in the same manner as that described in step 5 of Method A (Step 4)

The present step can be carried out in the same manner as that described in step 6 of Method A.

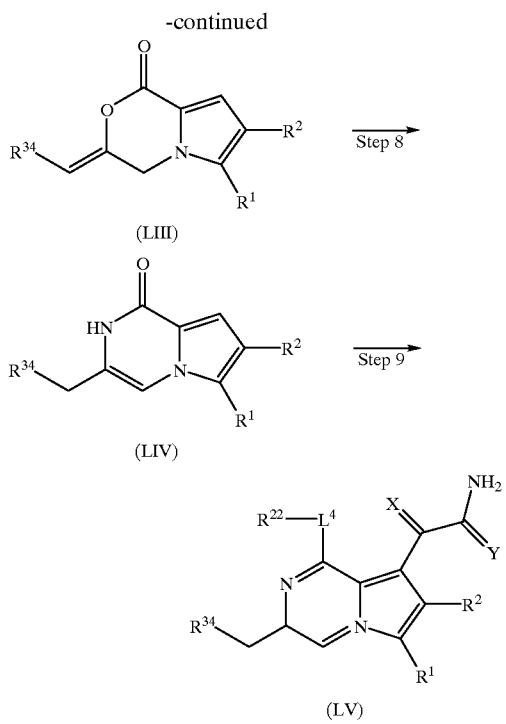

wherein $R^1$, $R^2$, $R^{22}$, $L^4$, X, Y and Hal are as defined above, $R^{32}$ and $R^{35}$ are C1–C3 alkyl, $R^{33}$ is lower alkyl, or a group which forms 1,3-dioxolane ring or 1,3-dioxane ring together with the adjacent oxygen atoms, $R^{34}$ is hydrogen atom, C1–C6 alkyl, C7–C12 aralkyl, C1–C6 alkyloxy, C1–C6 alkylthio, C1–C6 hydroxyalkyl, C2–C6 haloalkyloxy, halogen, carboxy, C1–C6 alkyloxycarbonyl, aryloxy, arylthio, a carbocyclic group or a heterocyclic group, Met is metal.

(Step 1)

The compound (XLVI) is dissolved in a solvent such as dimethylfomamide, an aikyl halide derivative (for example, bromoacetaldehyde ethyleneacetal and the like) and a base (for example, potassium carbonate, potassium t-butoxide, sodium hydride and the like) are added , and then the resulting mixture is stirred at 10 to 80° C., preferably 20 to 60° C., for 3 to 80 hours, preferably 5 to 70 hours. The compound (XLVII) is obtained by the usual work-up.

(Step 2)

The present step is a step of decarboxylation reaction. The compound (XLVII) is dissolved in a solvent such as dimethyl sulfoxide, a reagent such as potassium acetate, sodium acetate are added, and then the resulting mixture is stirred at 20 to 200° C., preferably 100 to 180° C., for 1 to 20 hours, preferably 3 to 15 hours. The compound (XLVIII) is obtained by the usual work-up.

(Step 3)

The present step is a step of addition reaction of alkyl metal reagent to nitrile group. A solution of the compound (XLVIII) in diethyl ether, tetrahydrofuran, dimethoxyethane or the like is added to Grignard reagent ($R^1$MgHal, Hal is halogen) or a solution of $R^1$Li in diethyl ether, tetrahydrofuran or dimethoxyethane at −20 to 30° C., and the mixture is stirred at 0 to 70° C, preferably 20 to 60° C, for 1 to 20 hours, preferably 2 to 10 hours. The compound (IL) is obtained by the usual work-up by using an acid such as diluted sulfuric acid.

(Step 4)

The present step is a step for constructing pyrrole ring. The compound (IL) is dissolved in a solvent such as tetrahydrofuran, substituted allylamine and a catalytic amount of an acid (for example, 1N hydrochloric acid) are added, and then the mixture is stirred at 0 to 100° C, preferably 0 to 50° C, for 1 to 5 hours, preferably 1 to 2 . The compound (L) is obtained by the usual work-up. Alternatively, the compound (IL) is converted into ketoaldehyde derivative by hydrolysis of acetal portion using an acid such as hydrochloric acid in a solvent such as tetrahydrofuran. Subsequently, the mixture is treated with substituted abylamine in a suitable solvent at 0 to 100° C., preferably 0 to 50° C., for 1 to 5 hours, preferably 1 to 2 hours to obtain the compound (L).

(Step 5)

The present step is a step for introducing alkoxycarbonyl group to pyrrole ring. The reaction can be carried out as described in step 3 of Method A by using chlorocarbonate. Alternatively, the compound (L) is converted into trichloroacetyl form by stirring it with trichloroacetyl chloride in a solvent such as tetrahydrofuran at 0 to 100° C., preferably 10 to 40° C., for 1 to 5 hours, preferably 1 to 2 hours. Subsequently, in a suitable alcohol, the mixture is treated with metal alkoxide of the same alcohol at 0 to 100° C., preferably 10 to 60° C., for 1 to 5 hours, preferably 1 to 2 hours to obtain the compound (LI).

(Step 6)

The present step is a step for constructing pyrrolomorpholine ring by iodo lactonization reaction. The compound (LI) is dissolved in a solvent such as acetonitrile, iodine was added, and the mixture is stirred at 0 to 50° C., preferably 10 to 30° C., for 1 to 10 hours, preferably 1 to 3 hours. The compound (LII) is obtained by the usual work-up.

(Step 7)

The present step is a step for forming double bond by eliminating HI. The compound (LII) is dissolved in a solvent such as toluene, acetonitrile, tetrahydrofuran, a base such as 1,8-diazabicyclo[5.4.0]-7-undecene is added, and the mixture is stirred at 0 to 100° C., preferably 20 to 80° C., for 1 to 5 hours, preferably 1 to 3 hours. The compound (LIII) is obtained by the usual work-up.

(Step 8)

The present step is a step for constructing pyrrolo[1,2-a] pyrazine ring, and can be conducted in accordance with the method described in J. Org. Chem., 53, 4650 (1988) (The disclosure of which are incorporated herein by reference). The compound (LIII) is dissolved in an alcoholic solvent or a solvent such as acetonitrile, tetrahydrofuran, a source of ammonia such as ammonium acetate is added, and the mixture is stirred at 0 to 100° C., preferably 20 to 80° C., for 3 to 24 hours, preferably 5 to 18 hours. The compound (LIV) is obtained by the usual work-up.

(Step 9)

The present step can be carried out in the same manner as those described in steps 6 to 8 of Method A.

(Method I)

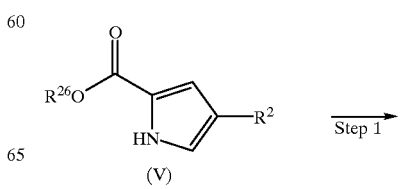

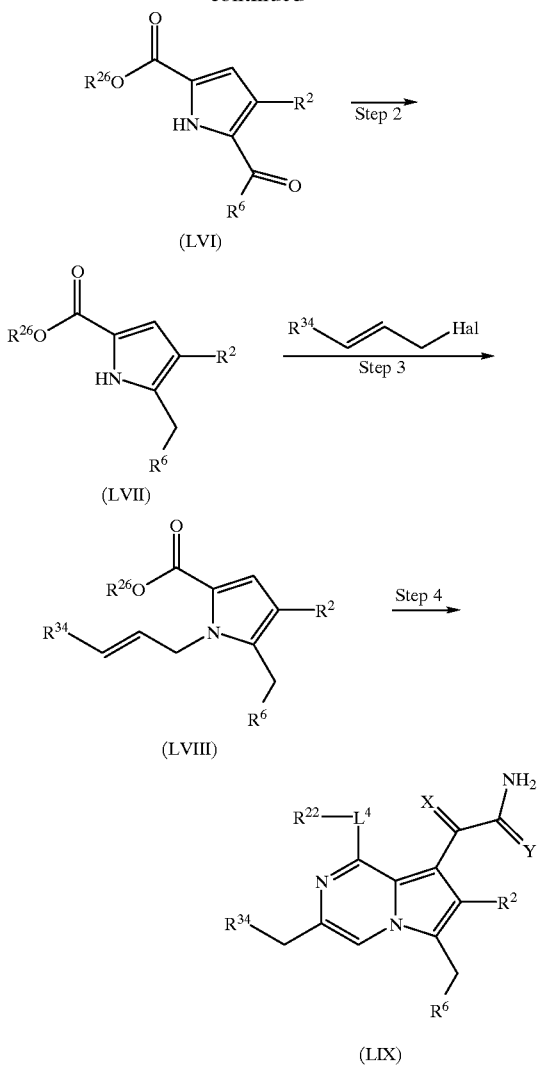

wherein $R^2$, $R^6$, $R^{22}$, $R^{26}$, $R^{34}$, $L^4$, X, Y and Hal are as defined above.

(Step 1)

The present step can be carried out in the same manner as that described in step 3 of Method A (Step 2)

The present step can be carried out in the same manner as that described in step 4 of Method A (Step 3)

The present step is a step of allylation of nitrogen at N1-position of pyrrole. The compound (LVII) is dissolved in a solvent such as tetrahydrofuran, dimethylformamide, allyl halide derivative and a base (for example, sodium hydride, potassium carbonate) is added, and the mixture is stirred at 0 to 100° C., preferably 0 to 50° C., for 1 to 10 hours, preferably 1 to 3 hours. The compound (LVIII) is obtained by the usual work-up.

(Step 4)

The present step can be carried out in the same manner as those described in steps 6 to 9 of Method H.

Where a compound of the present invention has an acidic or basic functional group, a variety of salts each having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates (phonetic), carbonates, chlorides, clubranates (phonetic), citrates, edetates (phonetic), edicirates (phonetic), estrates (phonetic), ethylates, fluorides, fumarates, gluseptates (phonetic), gluconates, glutamates, glycolialsanyrates (phonetic), hexylresorcinates, hydroxynaphthoates, iodides, isothionates, lactates, lactobionates, laurates, malates, malseates (phonetic), manderates (phonetic), methylates, methylbromides, methylnitrates, methylsulfates, mucates, napcylates (phonetic), nitrates, oleates, oxarates, palnitates, pantothenates, phosphates, polygalacturonates, salicirates, stearates, subacetates (phonetic), sucinates (phonetic), tanates (phonetic), tartrates, tosylates, trifluoroacetates, trifluoromethanesulfonates, valerates and the like. In case of forming a hydrate, a questioned compound may be coordinated with a suitable number of water molecules.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). Ester prodrugs are well known (see, Silverman, Richard B, The Organic Chemistry of Drug Design and Drug Action, Chapter 8, New York, N.Y. Academic Press, ISBN 0-12-643730-0) and are a preferred prodrug form for the compounds of this invention and also for prodrugs used in the method of treating Inflammatory Disease as taught herein. For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. Particularly preferred esters as prodrugs are methyl, ethyl, propyl, isopropyl n-butyl, isobutyl, tert-butyl morpholinoethyl, and N,N-diethylglycolamido.

Methyl ester prodrugs may be prepared by reaction of the sodium salt of a compound of Formula (I) (in a medium such as dimethylformamide) with iodo methane (available from Aldrich Chemical Co., Milwaukee, Wis. USA; Item No. 28,956-6).

Ethyl ester prodrugs may be prepared by reaction of the sodium salt of a compound of Formula (I) (in a medium such as dimethylformamide) with iodo ethane (available from Aldrich Chemical Co., Milwaukee, Wis. USA; Item No. 1-778-0).

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) with 4—(2-chloroethyl)morpholine hydrochloride (available from Aldrich Chemical Co., Milwaukee, Wis. USA, Item No. C4,220-3).

Double ester such as (acyloxy)alkyl ester or ((alkyloxycarbonyl)oxy)alkyl ester type prodrugs may be optionally manufactured.

The term "inhibit" means that release of fatty acid started by $sPLA_2$ decreases significantly by the compounds of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit $sPLA_2$ inhibiting activity as per the description of the experimental examples which will be described hereinafter. Accordingly, when a curatively effective amount of the compounds represented by the formulae (I), (II), (III), and (IV), the prodrug derivatives thereof, or their pharmaceutically acceptable salts, or their solvates is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, mange, cardiac failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier (phonetic), paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

A lyophilized preparation may be prepared by dissolving active ingredients in a solution such as water, if necessary, with a solubilizer such as citric acid, edetic acid, polyphosphoric acid and their salts and a stabilizer such as mannitol, xylitol, sorbitol, glucose, fructose, lactose and maltose and lyophilizing it.

While a dosage differs dependent upon a state of disease, a route of administration, patient's age, and a body weight, it is usually 0.01 to 50 mg/kg/day in case of oral administration in adult.

The method of the invention for inhibiting sPLA$_2$ mediated release of fatty acids comprises contacting mammalian sPLA$_2$ with a therapeutically effective amount of a pyrrolo [1,2-a]pyrazine sPLA$_2$ inhibitors (and formulation containing such inhibitors) as taught, supra.

Preferably compounds of the invention (per Formula (I) or (II) or (III) or (IV) or pharmaceutical formulations containing these compounds) are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The improved method of treatment for sepsis using the pyrrolo[1,2-a]pyrazine sPLA$_2$ inhibitors (and formulation containing such inhibitors) may be practiced as follows:

The inhibitors of this invention are given by injection, either subcutaneously or into muscle tissue or by injection into a vein. Intravenous injection is the preferred mode of delivery to the mammal being treated and offers the advantage of a quick effect and rapid access into the circulation system, particularly in emergency situations.

It may be appreciated that it may be necessary to make routine variations to the dosage depending on the age and condition of the patient. The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic Compound (I) dosage level of from about 0.01 mg/kg to about 50 mg/kg of body weight of an Active ingredient of this invention.

This invention is a method of treating or preventing Inflammatory diseased, (e.g., sepsis, rheumatoid arthritis, osteoarthritis, asthma) by administering to a mammal in need thereof a therapeutically effective amount inhibitor. The administration to a septic patient may be either continuous or intermittent.

The decision to begin the therapy for sepsis will be based upon the appearance of the clinical manifestations of sepsis or laboratory tests which show initiation of the sepsis cascade (inclusive of renal complications or coagulation abnormalities or multiple organ failure). Typical clinical manifestations are fever, chills, tachycardia, tachypnea, altered mental state, hypothermia, hyperthermia, accelerated or repressed breathing or heart rates, increased or decreased white blood cell count, and hypotension. These and other symptoms are well known in the art as set out in standard references such as, Harrison's Principles of Internal Medicine (ISBN 0-07-032370-4) 1994, pages 511–515.

The decision to determine the length of therapy may be supported by standard clinical laboratory results from commercially available assays or instrumentation supporting the eradication of the symptoms defining sepsis. The method of the invention may be practiced by continuously or intermittently administering a therapeutically effective dose of the inhibitor. The administration can be conducted for up to a total of about 60 days with a preferred course of therapy lasting for up to 10 days.

The decision to end therapy by the method of the invention may be supported by standard clinical laboratory results from commercially available assays or instrumentation or the disappearance of clinical symptoms characteristic of sepsis. The therapy may be restarted upon the return of sepsis. Pediatric forms of sepsis are also successfully treated by the methods, compounds, and formulations of this invention.

When the compound of the present invention is a crystallized, it may show various crystal forms and crystal habits.

The present invention will be described in more detail in conjunction with examples and test examples hereinafter, but it is to be noted that the present invention is not limited thereto.

In the examples, the following abbreviations are used.

Me: methyl
Et: ethyl
Pr: propyl
Bu: butyl
Ph: phenyl
DBU: 1,8-diazabicyclo [5.4.0]-7-undecene
Boc: t-butyloxycarbonyl
DMSO: dimethylsulfoxide

BEST MODE FOR CARRYING OUT THE INVENTION

Example 1

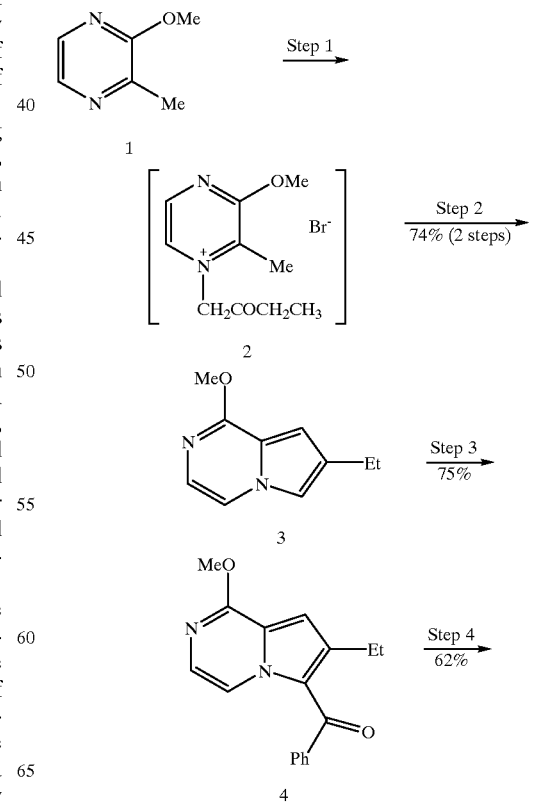

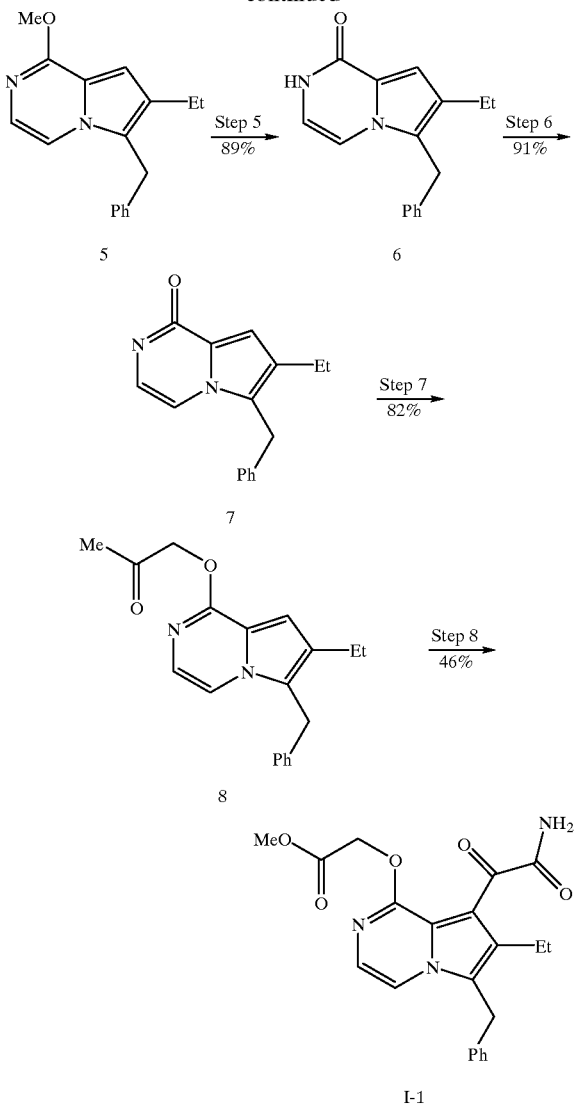

Example 1—Step 1

A mixture of 720 mg (5.81 mmol) of compound (1) and 904 mg (6.00 mmol) of 1-bromo-2-butanone was warmed at 60° C. for 20 hours to obtain a quaternary salt (compound (2)). NMR (CDCl$_3$) δ7 1.17(t, J=7.2 Hz, 3H), 2.77(s, 3H), 2.94(q, J=7.2 Hz, 2H), 4.19(s, 3H), 6.93(s, 2H), 8.57(d, J=3.9 Hz, 1H), 9.17(d, J=3.9 Hz, 1H).

Example 1—Step 2

To the crude compound (2) obtained in the step 1 were added 22 ml of 1,2-dichloroethane and 1.32 g (8.72 mmol) of DBU, and the resulting mixture was heated at 70° C. and stirred in an oil bath for 20 hours. To the reaction solution were added chloroform, water, and brine to separate an organic layer, and an aqueous layer was further extracted with chloroform. The organic layer was combined, dried over magnesium sulfate, thereafter the solvent is removed, and the residue was subjected to silica gel column chromatography. The fractions eluting with chloroform-methanol (100:1) were collected to give compound (3) (750 mg, 74% yield) as an oil.

NMR (CDCl$_3$) δ7 1.27(t, J=7.4 Hz, 3H), 2.69(q, J=7.4 Hz, 2H), 4.04(s, 3H), 6.62(s, 1H), 7.00–7.03(m, 1H), 7.16(d, J=0.8 Hz, 1H), 7.39–7.42(m, 1H).

Example 1—Step 3

The compound (3) (2.4 g (13.6 mmol)) was dissolved in 15 ml of benzoyl chloride, and 5.42 g (40.8 mmol) of aluminum chloride was added to the solution at an internal temperature of −10° C. to 0° C. over 10 minutes. The resulting mixture was further stirred at 5° C. for 15 hours. The reaction solution was poured into a mixed solution of ice-water and chloroform. The organic layer was separated and the aqueous layer was extracted with chloroform. The organic layer was washed with aqueous sodium bicarbonate and brine, dried over magnesium sulfate, and concentrated in vacuo and the residue was subjected to silica gel chromatography. The fractions eluting with chloroform-methanol (40:1) were collected to give compound (4) (2.68 g, 75% yield) as a crystal. The resulting crystal was recrystallized from ether and hexane. Melting point: 83–84° C.

Elemental Analysis C$_{17}$H$_{16}$N$_2$O$_2$, Calcd.: C, 72.84; H, 5.75; N, 9.99 Found: C, 72.94; H, 5.78; N, 10.16

NMR (CDCl$_3$) δ7 1.08(t, J=7.4 Hz, 3H), 2.33(q, J=7.4 Hz, 2H), 4.10(s, 3H), 6.72(s, 1H), 7.31(s, 1H), 7.44–7.70(m, 5H), 8.66(d, J=0.9 Hz, 1H). IR (CHCl$_3$) 1615 cm$^{-1}$.

Example 1—Step 4

To a solution of 240 mg (1.8 mmol) of aluminum chloride in 12 ml of methylene chloride was added 312 mg (3.6 mmol) of boron-t-butylamine complex under ice-cooling over 3 minutes. The resulting mixture was stirred under the same condition as described above for 10 minutes. To the resulting mixture was added dropwise a solution of 168 mg (0.6 mmol) of the compound (4) in 2.5 ml of methylene chloride under ice-cooling, thereafter the mixture was stirred for 20 minutes, and further stirred at room temperature for 3 hours. To the reaction mixture were added chloroform, ice-water, and diluted hydrochloric acid, the admixture was stirred for several minutes, thereafter the organic layer was separated, and the aqueous layer was further extracted with chloroform. The organic layer was washed with brine, dried over magnesium sulfate, and concentrated in vacuo. The residue was subjected to alumina column chromatography. The fractions eluting, with chloroform-hexane (2:1) were collected to give compound (5) (99 mg, 62% yield).

The compound was recrystallized from ether and hexane. Melting point: 56–57° C.

Elemental Analysis C$_{17}$H$_{18}$N$_2$O, Calcd.: C, 76.66; H, 6.81; N, 10.52 Found: C, 76.47; H, 6.80; N, 10.53

NMR (CDCl$_3$) δ1.27(t, J=7.5 Hz, 3H), 2.69(q, J=7.5 Hz, 2H), 4.04(s, 3H), 4.21(s, 2H), 6.73(s, 1H), 6.95–7.29(m, 7H).

Example 1—Step 5

To 1.7 g (6.38 mmol) of the compound (5) was added 51 ml of concentrated hydrochloric acid, and the resulting mixture was heated and stirred in an oil bath at 110° C. for 140 minutes. The reaction mixture was concentrated in vacuo. The residue was poured into a mixed solution of ice-water and chloroform, and sodium bicarbonate (12 g)

was gradually added to the mixture. The organic layer was separated and the aqueous layer was further extracted with chloroform. The organic layer was washed with brine, dried over magnesium sulfate, and concentrated in vacuo to obtain crude crystal of compound (6) (1.44 g, 89% yield). The crude crystal can be used for the next step. The crude crystal was recrystallized from ethyl acetate to give the compound of which melting point is 204–207° C.

Elemental Analysis as $C_{17}H_{18}N_2O_2$, Calcd.: C, 72.32; H, 6.43; N, 9.92 Found: C, 72.11; H, 6.48; N, 9.98

NMR (CDCl$_3$) δ1.24(t, J=7.6 Hz, 3H), 2.62(q, J=7.6 Hz, 2H), 4.16(s, 2H), 6.35–6.41(m, 1H), 6.69–6.72(m, 1H), 7.01–7.29(m, 6H), 9.97(brs, 1H).

IR (CHCl$_3$) 3419, 3164, 1647 cm$^{-1}$.

Example 1—Step 6

To 1.18 g (4.68 mmol) of the compound (6) was added 35 ml of phosphorous oxychloride and the mixture was refluxed in oil bath for 4 hours. The residue obtained by distilling off excess phosphorus oxychloride was dissolved in chloroform, and the mixture was poured into ice-water. The resulting mixture was extracted with chloroform. The organic layer was washed with water, dried over magnesium sulfate, and concentrated in vacuo. The resulting residue was subjected to silica gel column chromatography. The fractions eluting with chloroform-methanol (50:1) were collected to give compound (7) (1.15 g, 91% yield) as an oil.

NMR (CDCl$_3$) δ1.31(t, J=7.8 Hz, 3H), 2.75(q, J=7.8 Hz, 2H), 4.25(s, 2H), 6.87(s, 1H), 6.99–7.02(m, 2H), 7.17–7.38 (m, 5H).

Example 1—Step 7

To a suspension of methyl glycolate (2 ml) and sodium (200 mg (8.70 mmol)) were added successively a solution of 250 mg (0.923 mmol) of compound (7) in 1 ml of methyl glycolate, and 25 mg of sodium p-toluenesulfinate, and the resulting mixture was heated at 90° C. in oil bath for 20 hours. The reaction mixture was diluted with chloroform and brine was added to the resulting mixture. The organic layer was separated and the aqueous layer was further extracted with chloroform. The organic layer was dried over magnesium sulfate and concentrated in vacuo. The residue was subjected to silica gel column chromatography. The fractions eluting with ethyl acetate-hexane were collected to give compound (8) (245 mg, 82% yield) as an oil.

NMR (CDCl$_3$) δ1.28(t, J=7.5 Hz, 3H), 2.71(q, J=7.5 Hz, 2H), 3.78(s, 3H), 4.22(s, 2H), 5.01(s, 2H), 6.83(s, 1H), 6.89–7.29(m, 7H).

Example 1—Step 8

To a solution of 245 mg (0.756 mmol) of compound (8) in 11 ml of 1,2-dichloroethane were added 480 mg (3.78 mmol) of oxalyl chloride and 382 mg (3.78 mmol) of N-methylmorpholine, and the resulting mixture was heated at 50° C. in oil bath for 4 hours. The reaction mixture was poured into aqueous ammonia, and the mixture was stirred at room temperature for 10 minutes, and then extracted with chloroform. The organic layer was washed with brine, dried over magnesium sulfate, and concentrated in vacuo. The residue was subjected to alumina column chromatography. The fractions eluting with chloroform were collected to give compound (I-1) (137 mg, 46% yield) as a crystal. The crude crystal was recrystallized from a chloroform and methanol to obtain compound of which melting point is 151–152° C.

Elemental Analysis $C_{21}H_{21}N_3O_5$, Calcd.: C, 63.79; H, 5.35; N, 10.63 Found: C, 63.67; H, 5.56; N, 10.43

NMR (CDCl$_3$) δ1.21(t, J=7.5 Hz, 3H), 2.85(q, J=7.5 Hz, 2H), 3.75(s, 3H), 4.24(s, 2H), 4.97(s, 2H), 5.70(brs, 1H), 6.68(brs, 1H), 7.06–7.14(m, 3H), 7.23–7.31(m, 4H).

IR (CHCl$_3$) 3515, 3401, 1762, 1702, 1655 cm$^{-1}$.

Example 2

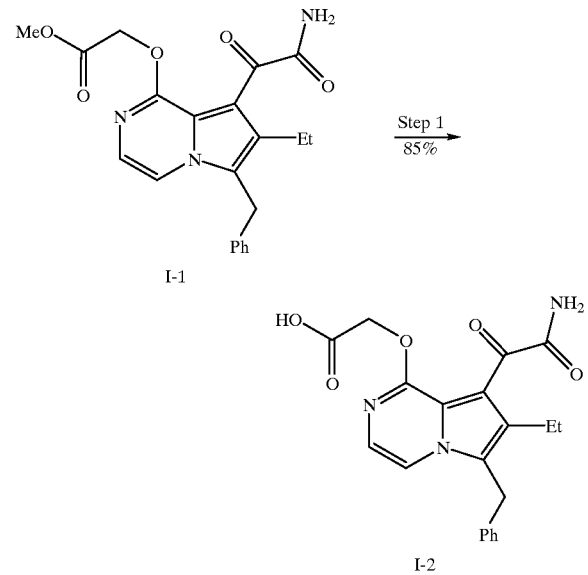

Example 2—Step 1

To a solution of 110 mg (0.278 mmol) of compound (I-1) in 15 ml of methanol was added 0.56 ml (0.556 mmol) of 1 N sodium hydroxide, and the resulting mixture was stirred at room temperature for 18 hours. The reaction mixture was concentrated in vacuo, and ice-water was added to the residue. To the resulting mixture was added 1 N hydrochloric acid (0.65 ml) and stirred at room temperature. The precipitated crystal was collected by filtration to give compound (I-2) (90 mg, 85% yield). The resulting crude crystal was recrystallized from methanol and chloroform to give compound of which decomposition point is 211–213° C.

NMR (DMSO-d6) δ1.07(t, J=7.2 Hz, 3H), 2.77(q, J=7.2 Hz, 2H), 4.34(s, 2H), 4.65(s, 2H), 7.10–7.31(m, 6H), 7.46 (brs, 1H), 7.73(d, J=4.8 Hz, 1H), 8.03(brs, 1H)

IR (KBr) 3425, 1709, 1668, 1640 cm$^{-1}$.

The compounds (I-3) to (I-36) which were shown in Tables 1 to 4 were synthesized in a manner similar to those described in Examples 1 and 2.

TABLE 1
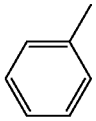
| Compound No. | $R^{36}$ | $R^{37}$ | $R^{38}$ | Melting point (° C.) | $^1$H-NMR: δ CDCl$_3$($R^{36}$ = Me), DMSO-d$_6$($R^{36}$ = H) |
|---|---|---|---|---|---|
| I-3 | Me | cyclopropyl | 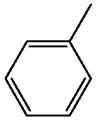 | 177–179 | 3.75(s, 3H), 4.38(s, 2H), 4.96 (s, 2H), 7.09(d, J=4.8Hz, 1H), 7.17(d, J=4.8Hz, 1H) |
| I-4 | H | cyclopropyl | 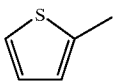 | 189–191 | 4.42(s, 2H), 4.79(s, 2H), 7.19 (d, J=5.1Hz, 1H), 7.71(d, J=5.1Hz, 1H) |
| I-5 | Me | Et | 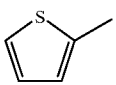 | 165–166 | 3.76(s, 3H), 4.38(s, 2H), 4.97 (s, 2H), 7.19(d, J=4.8Hz, 1H), 7.38(d, J=4.8Hz, 1H) |
| I-6 | H | Et | 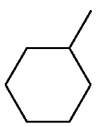 | 225–227 | 4.55(s, 2H), 4.81(s, 2H), 7.29 (d, J=4.8Hz, 1H), 7.92(d, J=4.8Hz, 1H) |
| I-7 | Me | Et | 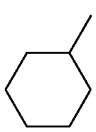 | 162–163 | 2.69(d, J=7.5Hz, 2H), 3.76(s, 3H), 4.96(s, 2H), 7.24(d, J=4.8Hz, 1H), 7.43(d, J=4.8Hz, 1H) |
| I-8 | H | Et | 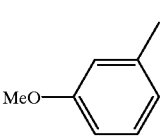 | 205–206 | 2.78(d, J=7.0Hz, 2H), 4.80(s, 2H), 7.29(d, J=4.8Hz, 1H), 7.98(d, J=4.8Hz, 1H) |
| I-9 | Me | Et | 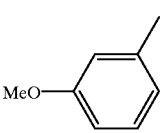 | 154–155 | 3.75(s, 3H), 3.76(s, 3H), 4.20 (s, 2H), 4.96(s, 2H), 7.13(d, J=4.8Hz, 1H), 7.26(d, J=4.8Hz, 1H) |
| I-10 | H | Et | 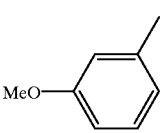 | 196–197.5 | 3.71(s, 3H), 4.32(s, 2H), 4.81 (s, 2H), 7.26(d, J=4.8Hz, 1H), 7.80(d, J=4.8Hz, 1H) |

TABLE 2

[Structure: pyrrolopyrazine core with R36O2C-CH2-O- substituent, oxoacetamide (C(=O)C(=O)NH2) group, R37 and CH2-R38 substituents]

| Compound No. | R36 | R37 | R38 | Melting point (° C.) | 1H-NMR: δ CDCl3(R36 = Me), DMSO-d6(R36 = H) |
|---|---|---|---|---|---|
| I-11 | Me | Et | 6-benzothiophenyl | 144–148 | 3.75(s, 3H), 4.37(s, 2H), 4.97 (s, 2H), 7.11(d, J=5.1Hz, 1H), 7.24(d, J=5.1Hz, 1H) |
| I-12 | H | Et | 6-benzothiophenyl | 209–211 | 4.49(s, 2H), 4.82(s, 2H), 7.25 (d, J=4.8Hz, 1H), 7.85(d, J= 4.8Hz, 1H) |
| I-13 | Me | Me | phenyl | 182–183 | 2.44(s, 3H), 3.75(s, 3H), 4.22 (s, 2H), 4.97(s, 2H) |
| I-14 | H | Me | phenyl | 207–208 | 2.36(s, 3H), 4.34(s, 2H), 4.81 (s,2H) |
| I-15 | Me | Et | cyclopentyl | 165–166 | 3.76(s, 3H),2.82(d, J=7.5Hz, 2H), 4.96(s, 2H), 7.24(d, J= 4.8Hz, 1H), 7.48(d, J=4.8Hz, 1H) |
| I-16 | H | Et | cyclopentyl | 203–205 | 2.91(d, J=7.8Hz, 2H), 4.80(s, 2H), 7.29(d, J=4.8Hz, 1H), 8.01(d, J=4.8Hz, 1H) |

TABLE 3

| Compound No. | R³⁶ | R³⁷ | R³⁸ | Melting point (°C.) | ¹H-NMR: δ CDCl₃(R³⁶ = Me), DMSO-d₆(R³⁶ = H) |
|---|---|---|---|---|---|
| I-17 | Me | Et | 2-methylphenyl | 192–194 | 2.17(d, J=0.9Hz, 3H), 3.75(s, 3H), 4.20(s, 2H), 4.97(s, 2H) |
| I-18 | H | Et | 2-methylphenyl | 207–208 | 2.18(s, 3H), 4.33(s, 2H), 4.81(s, 2H), 7.71(s, 1H) |
| I-19 | Me | Et | 4-fluorophenyl | 167–168 | 2.19(d, J=0.9Hz, 3H), 3.76(s, 3H), 4.17(s, 2H), 4.98(s, 2H) |
| I-20 | H | Et | 4-fluorophenyl | 204–205 | 2.18(d, J=0.9Hz, 3H), 4.31(s, 2H), 4.80(s, 2H), 7.72(d, J=0.9Hz, 1H) |
| I-21 | Me | Et | 2-biphenylyl | 164.5–165.5 | 2.12(d, J=0.9Hz, 3H), 3.73(s, 3H), 4.09(s, 2H), 4.94(s, 2H), 7.72(d, J=0.9Hz, 1H) |
| I-22 | H | Et | 2-(pyridin-2-yl)phenyl | 192–194 | 2.14(d, J=0.9Hz, 3H), 4.19(s, 2H), 4.80(s, 2H) |
| I-23 | Me | Et | cyclopentyl | 135–136.5 | 2.29(d, J=1.2Hz, 3H), 2.78(d, J=7.5Hz, 2H), 3.75(s, 3H), 4.96(s, 2H), 7.28(d, J=1.2Hz, 1H) |
| I-24 | H | Et | cyclopentyl | 192–193 | 2.26(s, 3H), 2.87(d, J=7.5Hz, 2H), 4.80(s, 2H), 7.86(s, 1H) |
| I-25 | Me | Et | 2-fluorophenyl | 187–188 | 2.20(d, J=0.9Hz, 3H), 3.75(s, 3H), 4.20(s, 2H), 4.97(s, 2H) |

TABLE 3-continued
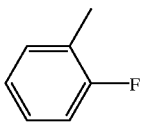
| Compound No. | R³⁶ | R³⁷ | R³⁸ | Melting point (° C.) | ¹H-NMR: δ CDCl₃(R³⁶ = Me), DMSO-d₆(R³⁶ = H) |
|---|---|---|---|---|---|
| I-26 | H | Et | 2-F-benzyl | 218–219 | 2.20(s, 3H), 4.33(s, 2H), 4.81 (s, 2H), 7.77(s, 1H) |
TABLE 4
| Compound No. | R³⁶ | R³⁷ | R³⁸ | Melting point (° C.) | ¹H-NMR: δ CDCl₃(R³⁶ = Me), DMSO-d₆(R³⁶ = H) |
|---|---|---|---|---|---|
| I-27 | Me | Et | 2-methylbenzyl-phenyl | 134.5–136 | 2.03(d, J=0.9Hz, 3H), 3.74(s, 3H), 4.03(s, 2H), 4.17(s, 2H), 4.94(s, 2H), 6.39(d, J=0.9Hz, 1H) |
| I-28 | H | Et | 2-methylbenzyl-phenyl | 180.5–182.5 | 2.07(d, J=0.6Hz, 3H), 4.19(s, 2H), 4.21(s, 2H), 4.80(s, 2H), 7.04(s, 1H) |
| I-29 | Me | Et | 2-methyl-4'-F-biphenyl | 147–149 | 2.13(d, J=0.9Hz, 3H), 3.74(s, 3H), 4.06(s, 2H), 4.95(s, 2H), 6.75(d, J=0.9Hz, 1H) |

TABLE 4-continued
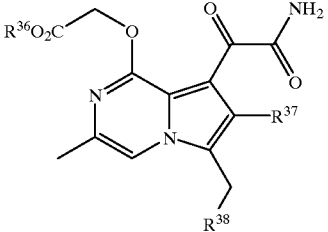
| Compound No. | R³⁶ | R³⁷ | R³⁸ | Melting point (° C.) | ¹H-NMR: δ CDCl₃(R³⁶ = Me), DMSO-d₆(R³⁶ = H) |
|---|---|---|---|---|---|
| I-30 | H | Et | 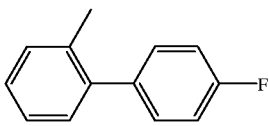 | 175–177 | 2.15(s, 3H), 4.18(s, 2H), 4.80 (s, 2H), 7.36(s, 1H) |
| I-31 | Me | Et | 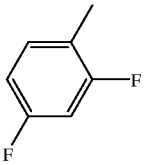 | 161–163 | 2.21(d, J=0.9Hz, 3H), 3.76(s, 3H), 4.15(s, 2H), 4.98(s, 2H) |
| I-32 | H | Et | 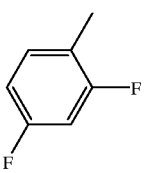 | 208–210 | 2.20(d, J=0.9Hz, 3H), 4.30(s, 2H), 4.81(s, 2H), 7.78(d, J= 0.9Hz, 1H) |
| I-33 | Me | Et | 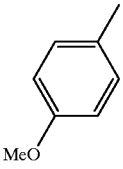 | 189–190 | 2.18(s, 3H), 3.75(s, 3H), 3.78 (s, 3H), 4.14(s, 2H), 4.97(s, 2H), 7.06(s, 1H) |
| I-34 | H | Et | 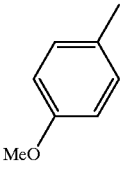 | 200–201.5 | 2.18(d, J=0.6Hz, 3H), 3.69(s, 3H), 4.24(s, 2H), 4.80(s, 2H), 7.06(s, 1H), 7.68(d, J=0.6Hz, 1H) |
| I-35 | Me | Et | 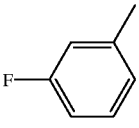 | 179.5–181 | 2.19(d, J=0.9Hz, 3H), 3.76(s, 3H), 4.20(s, 2H), 4.97(s, 2H), 7.03(d, J=0.9Hz, 1H) |
| I-36 | H | Et | 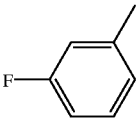 | 190.5–193 | 2.19(d, J=0.9Hz, 3H), 4.35(s, 2H), 4.81(s, 2H), 7.74(d, J= 0.9Hz, 1H) |

Example 37

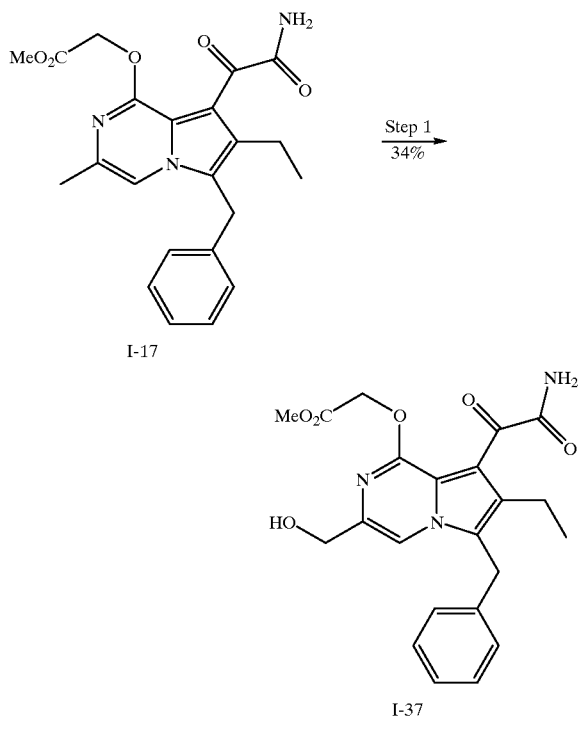

Example 38

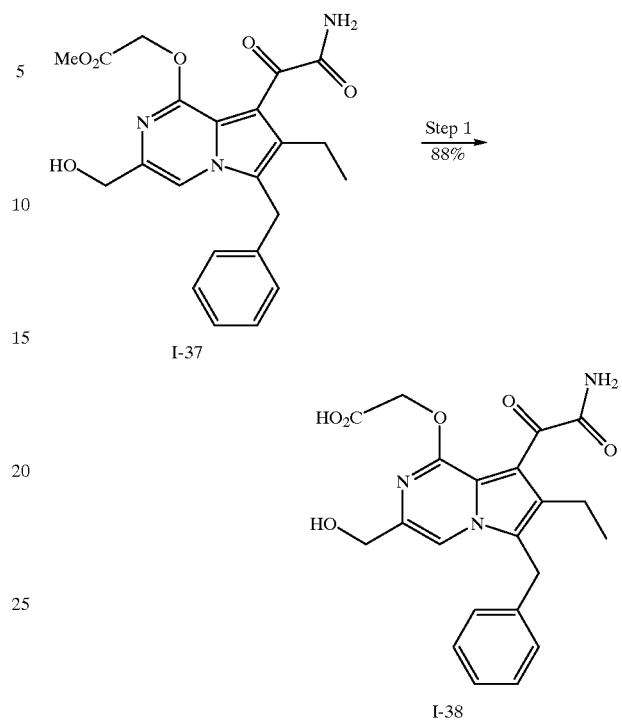

Example 37—Step 1

To a solution of 176 mg (0.430 mmol) compound (I-17) which was synthesized from 2,5-dimethyl-3-methoxypyrazine (Heterocycles, 1992, 34(9), 1759–1771) in accordance with the same manner as that of Example 1 in 6 ml of 1,4-dioxane was added 100 mg (0.860 mmol) of selenium dioxide, and the resulting mixture was refluxed or 9 hours. The resulting mixture was concentrated in vacuo and the residue was subjected to silica gel chromatography. The fractions eluting with chloroform-methanol (40:1) were collected to give compound (I-37) (63 mg, 34% yield) as yellow crystal.

Melting Point: 201–202° C.

Elemental Analysis $C_{22}H_{23}N_3O_6$, Calcd.: C, 62.11; H, 5.45; N, 9.88 Found: C, 62.11; H, 5.46; N, 9.84

$^1$H-NMR (CDCl$_3$) δ1.20 (t, J=7.5 Hz, 3H), 2.17 (brs, 1H), 2.84 (q, J=7.5 Hz, 2H), 3.75 (s, 3H), 4.23 (s, 2H), 4.43 (s, 2H), 4.97 (s, 2H), 5.56(brs, 1H), 6.70 (brs, 1H), 7.03–7.10 (m, 2H), 7.20–7.33 (m, 4H).

IR (KBr) 3418, 3260, 1758, 1692, 1630, 1606, 1502, 1344, 1213, 1159 cm$^{-1}$.

Example 38—Step 1

To a solution of 19 mg of the compound (I-37) in 0.5 ml of methanol and 0.5 ml of tetrahydrofuran was added 0.07 ml of 4 N sodium hydroxide at room temperature, and the resulting mixture was stirred at the same temperature for 1 hour. To the reaction mixture were added water and 1 ml of 1 N hydrochloric acid, and the resulting mixture was extracted with ethyl acetate. The organic layer was successively washed with water and brine, dried over sodium sulfate, and the concentrated in vacuo. The residue was recrystallized from ethyl acetate and hexane to give compound (I-38) (16 mg, 88% yield) as light yellow crystal.

Melting Point 211–212° C.

Elemental Analysis $C_{21}H_{21}N_3O_6$, Calcd.: C, 61.31; H, 5.14; N, 10.21 Found: C, 61.16; H, 5.19; N, 10.13

$^1$H-NMR (DMSO-d$_6$) δ1.07 (t, J=7.5 Hz, 3H), 2.77(q, J=7.5 Hz, 2H), 4.31 (d, J=3.0 Hz, 2H), 4.35 (s, 2H), 4.81 (s, 2H), 5.31 (brs, 1H), 7.10 (d, J=7.5 Hz, 2H), 7.21 (t, J=7.5 Hz, 1H), 7.30 (t, J=7.5 Hz, 2H), 7.50 (brs, 1H), 7.68 (s, 1H), 7.89 (brs, 1H).

IR (KBr) 3412, 1712, 1667, 1501, 1317, 1227, 1212, 1163 cm$^{-1}$.

Example 39

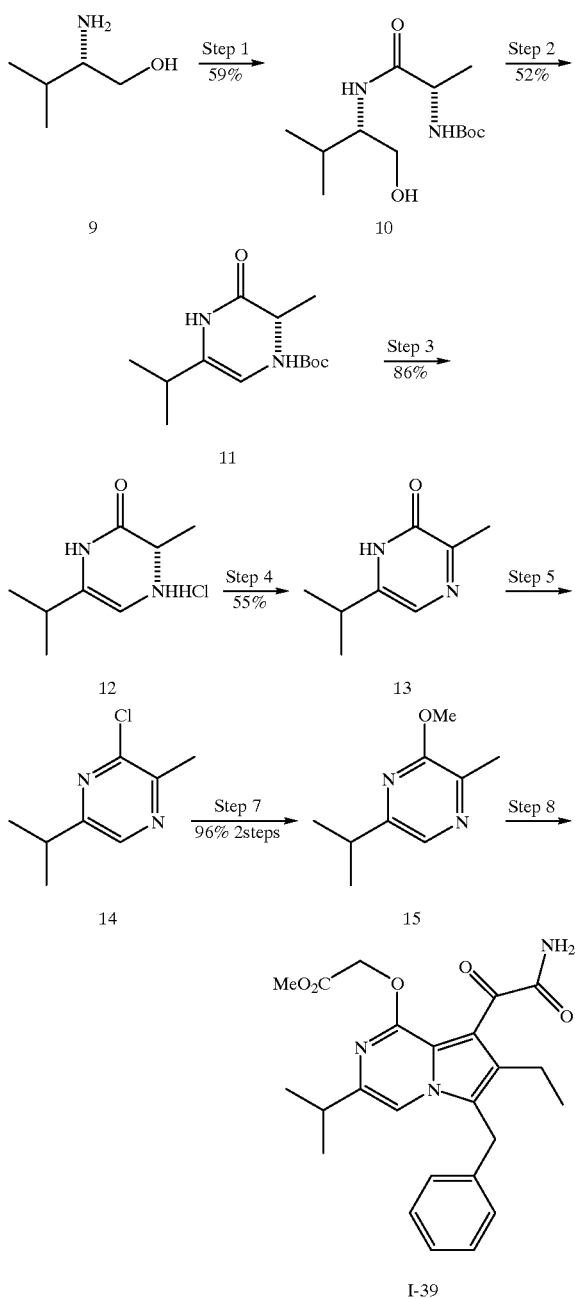

Example 39—Step 1

L-valinol (9) (22.7 g (220 mmol)) was dissolved in 200 ml of acetonitrile. To the mixture was added a solution of 41.7 g (220 mmol) of Boc-L-alanine in 100 ml of acetonitrile under ice-cooling. Thereafter, 46.6 g (242 mmol) of 1-ethyl-3-(3-dimethylaminopropyl)-carbodiimide hydrochloride was added, and the mixture was stirred at room temperature under nitrogen atmosphere for 24 hours. Acetonitrile was removed from the reaction mixture under reduced pressure, and the residue was poured into 100 ml of water, and extracted with ethyl acetate. The organic layer was washed with brine, dried over magnesium sulfate, and concentrated in vacuo. The residue (77.5 g) was poured into diluted aqueous hydrochloric acid. After pH was adjusted to 2 to 3, the whole was extracted again with ethyl acetate. The organic layer was washed with aqueous saturated sodium bicarbonate, dried over magnesium sulfate, and concentrated in vacuo to obtain compound (10) (35.7 g, 59% yield) as colorless crystal. A little quantities of the crystals were recrystallized from diethyl ether-hexane to obtain colorless needles.

Melting Point: 96.0–97.0° C.

Elemental Analysis as $C_{18}H_{26}N_2O_4$, Calcd.: C, 56.91; H, 9.55; N, 10.21 Found: C, 56.77; H, 9.51; N, 10.14

$^1$H-NMR (CDCl$_3$) δ0.94 (dd, J=8.7, 6.9 Hz, 6H), 1.37 (d, J=7.2 Hz, 3H), 1.45 (s, 9H), 1.89 (m, 1H), 2.28 (brs, 1H), 3.57–3.77 (m, 3H), 4.14 (quint, J=7.2 Hz, 1H), 5.05 (d, J=6.6 Hz, 1H), 6.50 (d, J=7.5 Hz, 1H).

IR (CHCl$_3$) 3626, 3437, 1695, 1496, 1455, 1392, 1369, 1325 cm$^{-1}$.

Example 39—Step 2

The compound (10) (31.5 g (107 mmol)) was dissolved in 350 ml of ethyl acetate. To the mixture were successively added 167 mg (1.07 mmol) of TEMPO (2,2,6,6-tetramethylpiperidin-1-oxide), 1.27 g (10.7 mmol) of potassium bromide, and 268 ml of 0.4 N aqueous NaOCl (pH was adjusted to 9.60 with NaHCO$_3$) at −6 ° C. (internal temperature) and the resulting mixture was stirred at the same temperature. After 45 minutes, the reaction mixture was poured into 100 ml of water, shaken, and extracted with ethyl acetate. The ethyl acetate layer was washed with brine, and the aqueous layer was further extracted with ethyl acetate. After drying the organic layers with magnesium sulfate, the solvent was removed under reduced pressure, and dried under reduced pressure to obtain 25.3 g of light cream-colored foam. The residue was dissolved in 200 ml of toluene, and the mixture was allowed to stand at room temperature for 2 hours. The reaction mixture was concentrated under reduced pressure, and the residue was subjected to silica gel chromatography. The fractions eluting with hexane-ethyl acetate (7:1) were collected to give compound (11) (14.1 g, 52% yield) as colorless crystal. A little quantities of the crystals were recrystallized from diethyl ether-hexane to obtain colorless prisms.

Melting Point: 165.0–166.0° C.

Elemental Analysis $C_{13}H_{22}N_2O_3$, Calcd.: C, 61.39; H, 8.72; N, 11.01 Found: C, 61.33; H, 8.74; N, 10.95

$^1$H-NMR (CDCl$_3$) δ1.15 (d, J=6.9 Hz, 6H), 1.27 (d, J=6.9 Hz, 3H), 1.50 (s, 9H), 2.39 (m, 1H), 4.73 (m, 1H), 5.90 and 6.08 (each brs, total 1H), 7.89 (brs, 1H).

IR (CHCl$_3$) 3408, 1685, 1472, 1454, 1437, 1395, 1370, 1325 cm$^{-1}$.

Example 39—Step 3

To a suspension of 1.02 g (3.99 mmol) of compound (11) in 5 ml of ethyl acetate was added 10 ml (40.0 mmol) of 4 N hydrochloric acid in ethyl acetate, and the resulting mixture was stirred at room temperature. After 2 hours, the precipitated crystal was collected by filtration, and washed with ethyl acetate to obtain compound (12) (655 mg, 86% yield) as colorless crystal.

$^1$H-NMR (CD$_3$OD) δ1.57 (d, J=7.2 Hz, 3H), 1.77 (s, 6H), 3.92 (m, 1H), 4.13 (q, J=7.2 Hz, 1H), 4.30 and 4.35 (each s, total 1H).

Example 39—Step 4

646 mg (3.39 mmol) of the compound (12) was dissolved in 2 ml of water, and sodium bicarbonate was gradually added to be alkaline. The reaction mixture was extracted with ethyl acetate, and further with dichloromethane. The organic layer was dried over magnesium sulfate, concentrated in vacuo, and dried under reduced pressure to obtain 517 mg of colorless crystal. The residue (517 g) was dissolved in 6.95 ml of cyclohexene and 1.4 ml of methanol, and 290 mg of 10% Pd—C was added to the mixture, and the resulting mixture was stirred at 80° C. for 3.5 hours. After the reaction mixture was cooled to room temperature, Pd—C was filtered off. The filtrate was concentrated in vacuo. The residue (630 mg) was subjected to silica gel chromatography. The fractions eluting with toluene-ethyl acetate (1:1) were collected to give compound (13) (285 mg, 55% yield) as colorless crystal. A little quantities of crystals were recrystallized from diethyl ether-hexane to obtain as colorless prisms.

Melting Point: 133.0–134.0° C.

Elemental Analysis $C_8H_{12}N_2O\cdot 0.1\ H_2O$, Calcd.: C, 62.40; H, 7.99; N, 18.19 Found: C, 62.61; H, 7.98; N, 18.24

$^1$H-NMR (CDCl$_3$) δ1.33 (d, J=7.2 Hz, 6H), 2.42 (s, 3H), 2.84 (m, 1H), 7.17 (s, 1H), 12.48 (brs, 1H).

IR (CHCl$_3$) 3373, 1649, 1612, 1534, 1467, 1433, 1389, 1372 cm$^{-1}$.

Example 39—Steps 5 and 6

To 4.09 g (26.9 mmol) of the compound (13) was added 11.2 ml of phosphorus oxychloride, and the mixture was refluxed under nitrogen atmosphere for 1 hour. After cooling the reaction mixture, the mixture was gradually poured into 100 ml of ice-water and 60 ml of diethyl ether. To the mixture was added 45 ml of 28% aqueous ammonia to adjust pH to 5 to 6. About 40 ml of 5 N sodium hydroxide was further added thereto to be alkaline, and then extracted with diethyl ether. The organic layer was dried over magnesium sulfate, and the solvent was removed under normal pressure to obtain 5.38 g of compound (14) as brown oil.

$^1$H-NMR (CDCl$_3$) δ1.32 (d, J=6.9 Hz, 6H), 2.62 (s, 3H), 3.06 (m, 1H), 8.26 (s, 1H).

To a solution of 5.38 g compound (14) in 18 ml of methanol was added 18.6 ml (93.0 mmol) of 28% sodium methoxide in methanol, and the resulting mixture was refluxed for 1 hour. After cooling the reaction mixture, it was concentrated in vacuo. The residue was poured into 30 ml of water, and the mixture was extracted with diethyl ether. The organic layer was washed with brine and dried over magnesium sulfate. The solvent was removed under normal pressure to obtain compound (15) (4.27 g, 96% yield) as brown oil.

$^1$H-NMR (CDCl$_3$) δ1.28 (d, J=6.9 Hz, 6H), 2.42 (s, 3H), 2.95 (m, 1H), 3.96 (s, 3H), 7.85 (s, 1H).

Example 39—Step 7

Using the compound (15) as a starting material, compound (I-39) was synthesized in a manner similar to that described in Example 1.

Example 40

The compound (I-40) was synthesized by carrying out the same reaction as described in Example 2.

Example 41

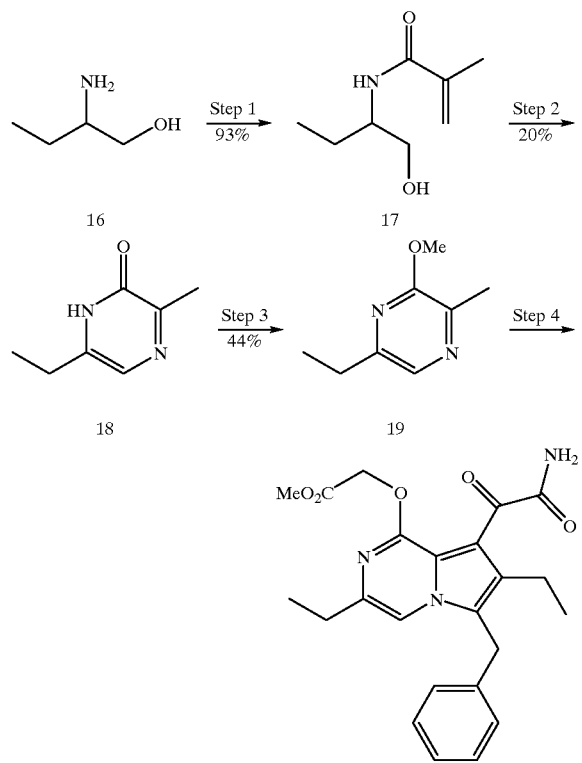

Example 41—Step 1

Under ice-cooling, 7.24 g (84.0 mmol) of methacrylic acid, 16.3 g (84.0 mmol) of 1-ethyl-3-(3-dimethylaminopropyl)-carbodiimide hydrochloride, and 7.54 g (84.0 mmol) of 2-amino-1-buthanol (16) were dissolved in 100 ml of dichloromethane, and the mixture was stirred at room temperature for 20 hours. Dichloromethane was removed, then water was added to the residue, and the whole was extracted with ethyl acetate. The organic layer was washed successively with 10% hydrochloric acid, aqueous saturated sodium bicarbonate, and brine, dried over sodium sulfate, and concentrated in vacuo to obtain compound (17) (12.4 g, 93% yield) as yellow oil.

$^1$H-NMR (CDCl$_3$) δ0.98 (t, J=7.5 Hz, 3H), 1.59 (m, 2H), 1.98 (s, 3H), 3.64(dd, J=11.1, 6.0 Hz, 1H), 3.74 (dd, J=11.1, 3.3 Hz, 1H), 3.93 (m, 1H), 5.36 (s, 1H), 5.73 (s, 1H), 5.99 (brs, 1H).

IR (CHCl$_3$) 3428, 3004, 2962, 1711, 1655, 1617, 1514 cm$^{-1}$.

Example 41—Step 2

To a solution of 49.0 ml (690 mmol) of dimethyl sulfoxide in 50 ml of dichloromethane was added gradually 29.5 ml (345 mmol) of oxalyl chloride at −78° C. After stirring the mixture for 10 minutes, a solution of 18.1 g (115 mmol) of compound (17) in 100 ml of dichloromethane was added, and the resulting mixture was stirred at −78° C. for 1 hour. To the mixture was added 96.0 ml (690 mmol) of triethylamine, and the mixture was further stirred for 1 hour. To the reaction mixture was added 10% hydrochloric acid, and extracted with ethyl acetate. The organic layer was dried over sodium sulfate and concentrated in vacuo.

The residue was dissolved in 300 ml of dichloromethane and 100 ml of methanol, and ozone gas was bubbled through the solution at −78° C. At the time when a color of the reaction solution was turned to blue, 36.0 ml (575 mmol) of dimethyl sulfide was added, and the resulting mixture was stirred at room temperature for 2 hours. The reaction mixture was washed with brine, dried over sodium sulfate, and concentrated in vacuo.

The residue was dissolved in 200 ml of ethanol. To the mixture was added 17.7 g (230 mmol) of ammonium acetate and the resulting mixture was refluxed for 1 hour. After distilling off ethanol, water was added to the residue, and extracted with ethyl acetate. The organic layer was washed with brine, dried over sodium sulfate, and concentrated in vacuo. The residue was subjected to silica gel chromatography. The fractions eluting with ethyl acetate were collected to give compound (18) (3.19 g, 20% yield) as white crystal.

Melting Point: 151.0–153.0° C.

FABMS (m/z) 139 ([M+H]$^+$)

$^1$H-NMR (DMSO-d$_6$) δ1.14 (t, J=7.5 Hz, 3H), 2.41 (q, J=7.5 Hz, 2H), 2.21 (s, 3H), 7.02 (s, 1H), 12.08 (brs, 1H).

IR (KBr) 2971, 2920, 1653, 1619, 1367 cm$^{-1}$.

Example 41—Step 3

A mixture of 2.72 g (19.7 mmol) of the compound (18) and 13.5 ml (145 mmol) of phosphorus oxychloride was refluxed for 30 minutes. The reaction mixture was gradually poured into ice-water, and neutralized with 4 N sodium hydroxide with stirring. The resulting mixture was extracted with diethyl ether, and the organic layer was dried over sodium sulfate. To the residue obtained by distilling off the solvent under normal pressure was added 44.0 ml (44.0 mmol) of 1 N sodium methoxide in methanol, and the mixture was refluxed for 5 hours. Methanol was removed under normal pressure, then water was added to the residue, and extracted with diethyl ether. The organic layer was dried over sodium sulfate, and thereafter the solvent was removed under normal pressure to obtain compound (19) (1.32 g, 44% yield) as brown oil.

$^1$H-NMR (CDCl$_3$) δ1.29 (t, J=7.6 Hz, 3H), 2.42 (s, 3H), 2.69 (q, J=7.6 Hz, 2H), 3.97 (s, 3H), 7.85 (s, 1H).

IR (CHCl$_3$) 2968, 1546, 1452, 1369 cm$^{-1}$.

Example 41—Step 4

Using the compound (19) as a starting material, compound (I-41) was synthesized in a manner similar to that described in Example 1.

Compound (I-42) to compound (I-50) were synthesized by carrying out the same reactions as described in Example 1 to Example 41. Results obtained are shown in Tables 5 to 6.

TABLE 5

| Compound No. | R$^{36}$ | R$^{38}$ | R$^{39}$ | Melting point (° C.) | $^1$H-NMR: δ CDCl$_3$(R$^{36}$ = Me), DMSO-d$_6$(R$^{36}$ = H) |
|---|---|---|---|---|---|
| 1.39 | Me |  | isopropyl | 190–191 | 1.10(d, J=6.9Hz, 6H), 3.73 (s, 3H), 4.21(s, 2H), 4.93(s, 2H) |
| I-40 | H |  | isopropyl | 211–213 | 1.11(d, J=6.9Hz, 6H), 4.34 (s, 2H), 4.78(s, 2H), 7.59(s, 1H) |
| I-41 | Me |  | Et | 154–156 | *3.65(s, 3H), 4.34(s, 2H), 4.87(s, 2H), 7.69(s, 1H) |
| I-42 | H | 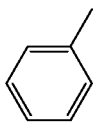 | Et | 197–198 | 4.34(s, 2H), 4.79(s, 2H), 7.67(s, 1H) |

TABLE 5-continued

| Compound No. | $R^{36}$ | $R^{38}$ | $R^{39}$ | Melting point (° C.) | $^1$H-NMR: δ CDCl$_3$($R^{36}$ = Me), DMSO-d$_6$($R^{36}$ = H) |
|---|---|---|---|---|---|
| I-43 | Me | benzyl | phenyl | 203–205 | *3.68(s, 3H), 4.51(s, 2H), 4.99(s, 2H), 8.40(s, 1H) |
| I-44 | H | benzyl | phenyl | 233–234 | 4.50(s, 2H), 4.91(s, 2H), 8.38(s, 1H) |
| I-45 | Me | benzyl | isobutyl | 129–130 | 2.25(d, J=7.2Hz, 2H), 3.72 (s, 3H), 4.22(s, 2H), 4.94(s, 2H), 7.01(s, 1H) |
| I-46 | H | benzyl | isobutyl | 216–217 | 2.30(d, J=6.9Hz, 2H), 4.34 (s, 2H), 4.78(s, 2H), 7.63(s, 1H) |
| I-47 | Me | | | 151–153 | *3.65(s, 3H), 4.33(s, 2H), 4.87(s, 2H), 7.70(s, 1H) |
| I-48 | H | | | 202–204 | 4.33(s, 2H), 4.80(s, 2H), 7.68(s, 1H) |

*measured with DMSO-d$_6$

TABLE 6

R³⁶O₂C-CH₂-O- [pyrrolopyrazine core with C(O)C(O)NH₂ at one position, ethyl, CH₂R³⁸, and R³⁹ substituents]

| Compound No. | R³⁶ | R³⁸ | R³⁹ | Melting point (° C.) | ¹H-NMR: δ CDCl₃(R³⁶ = Me), DMSO-d₆(R³⁶ = H) |
|---|---|---|---|---|---|
| I-49 | Me | (phenyl) | benzyl | 178–180 | *3.51(s, 3H), 3.76(s, 2H), 4.33(s, 2H), 4.82(s, 2H), 7.84(s, 1H) |
| I-50 | H | (phenyl) | benzyl | 200–202 | *3.77(s, 2H), 4.30(s, 2H), 4.78(s, 2H), 7.75(s, 1H) |

*measured with DMSO-d₆

Example 51

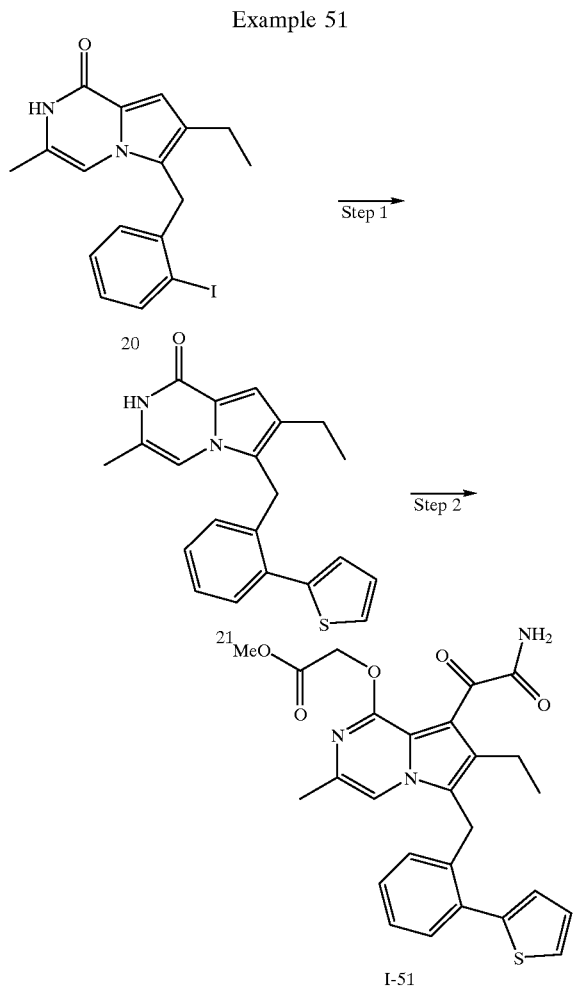

Example 51—Step 1

2-Thiopheneboronic acid (391 mg, 3.06 mmol) and 2 ml of 2M sodium carbonate were added to a solution of 800 mg of the compound (20) (2.04 mmol) and 118 mg of tetrakis (triphenylphosphine) palladium (0.102 mmol) in 18 ml of dimethoxyethane—ethanol (5:1) under argon atmosphere, and the resulting mixture was refluxed for 4 hours. To the reaction mixture was added 12 ml of 1N hydrochloric acid, and the resulting mixture was extracted with chloroform. The organic layer was washed with brine, dried over sodium sulfate, and concentrated in vacuo. The residue was subjected to the silica gel column chromatography. The fractions eluting with chloroform-methanol (98:2) were collected to obtain the compound (21) (592 mg, yield 83%) as a colorless crystal.

¹H-NMR(DMSO-d₆) δ1.04(t, J=7.5 Hz, 3H), 1.94(s, 3H), 2.36(q, J=7.5 Hz, 2H), 4.20(s, 2H), 6.60(s, 1H), 6.65(m, 1H), 6.74(s, 1H), 7.19–7.68(m, 6H), 10.40(brs, 1H).

Example 51—Step 2

Using the compound (21) as a starting material, compound (I-51) was synthesized in a manner similar to that described in step 6 to step 8 of Example 1.

Example 52

The compound (I-52) was synthesized by the same reaction described in Example 2 by using the compound (I-51) as a starting material.

Example 53

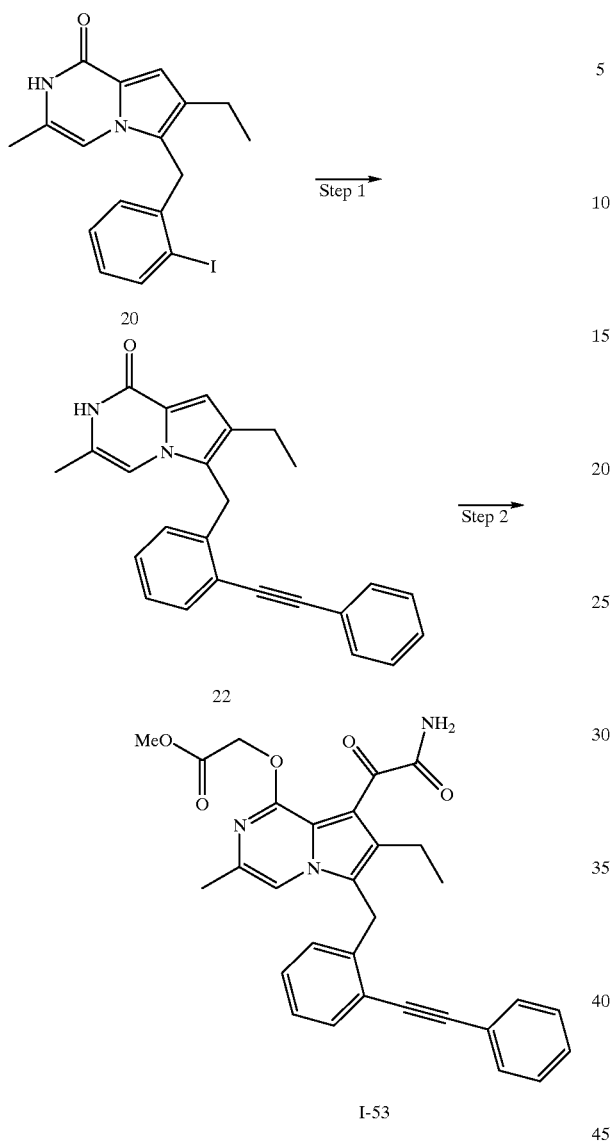

Example 53—Step 1

To a solution of 1 g of the compound (20) (2.55 mmol) in 10 ml of dimethylformamide were added 339 mg of phenylacetylene (3.31 mmol), 59 mg of dichlorobis(triphenylphosphine)palladium (0.084 mmol), 45 mg of cooper (1) iode (0.24 mmol) and 490 mg of triethylamine (4.84 mmol). The resulting mixture was stirred at 50° C. for 3 hours under argon atmosphere. After the reaction was completed, the resulting mixture was added to 2N hydrochloric acid and extracted with ethyl acetate. The organic layer was washed with brine, dried over sodium sulfate, and concentrated in vacuo. The residue was purified by the silica gel column chromatography to obtain the compound (22) (844 mg, yield 90%) as a colorless powder.

$^1$H-NMR(DMSO-$d_6$) δ1.08(3H, t, J=7.5 Hz), 1.93(3H, s), 2.46(2H, q, J=7.5 Hz), 4.36(2H, s), 6.74(1H, m), 6.76(1H, s), 6.93(1H, s), 7.26–7.61(8H, m), 10.40(1H, br).

Example 53—Step 2

Using the compound (22) as a starting material, compound (I-53) was synthesized in a manner similar to that described in step 6 to step 8 of Example 1.

Example 54

The compound (I-54) was synthesized by the same reaction described in Example 2 by using the compound (I-53) as a starting material.

Example 55

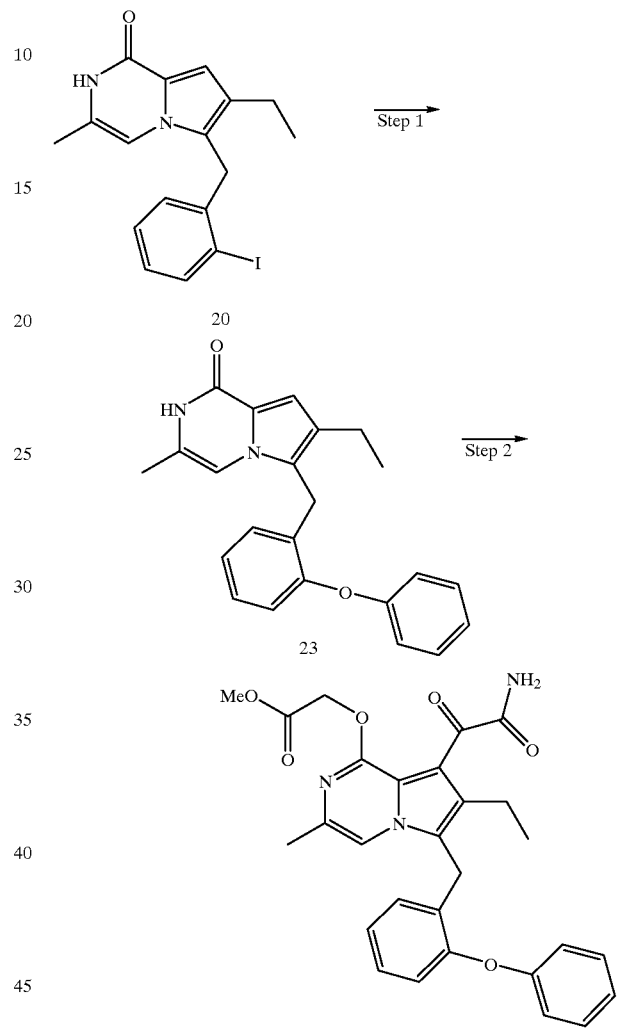

Example 55—Step 1

Cooper (II) oxide (1.11 g, 14.0 mmol) was added to a solution of 1.47 g of the compound (20) (3.50 mmol), 490 mg of phenol (5.21 mmol) and 1.48 g of potassium carbonate (10.5 mmol) in 7 ml of pyridine, and the resulting mixture was refluxed for 21 hours under nitrogen atmosphere. The reaction mixture was diluted with chloroform, filtered and then removed the solvent by distillation under reduced pressure. The residue was diluted with ethyl acetate, washed 2 times with 1N sodium hydrogensulfate, washed with brine, and then dried over sodium sulfate. The residue obtained by removing the solvent by distillation under reduced pressure was subjected to the silica gel column chromatography. The fractions eluting with n-hexane-ethyl acetate (5:1) were collected to obtain the compound (23) (1.35 g, yield 100%) as a colorless oil.

¹H-NMR(CDCl₃) δ1.11(t, J=7.4 Hz, 3H), 2.28(q, J=7.4 Hz, 2H), 2.33(d, J=0.9 Hz, 3H), 4.08(s, 3H), 6.62(d, J=0.9 Hz, 1H), 6.79–7.05(m, 4H), 7.17–7.24(m, 3H), 7.38–7.45 (m, 2H), 8.75(s, 1H).

Example 55—Step 2

Using the compound (23) as a starting material, compound (I-55) was synthesized in a manner similar to that described in step 6 to step 8 of Example 1.

Example 56

The compound (I-56) was synthesized by the same reaction described in Example 2 by using the compound (I-55) as a starting material.

Example 57

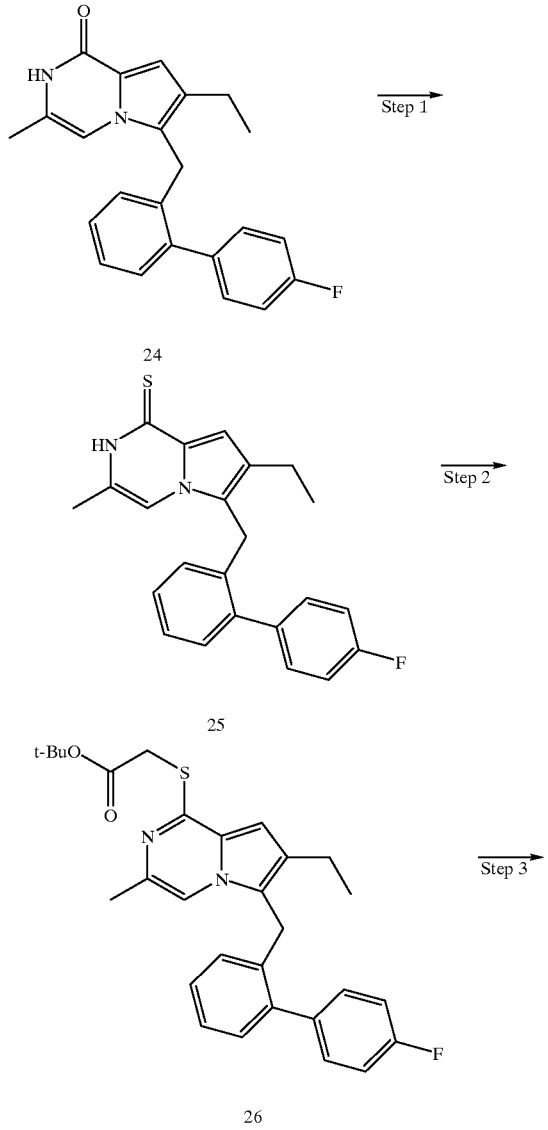

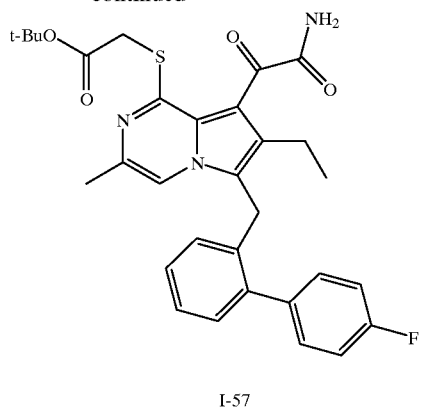

I-57

Example 57—Step 1

The compound (24) (860 mg, 2.39 mmol) and 394 mg of phosphorus pentasulfide (2.77 mmol) were dissolved in 8 ml of pyridine, and the resulting mixture was refluxed for 3 hours. After the reaction was completed, the resulting mixture was diluted with water and extracted with ethyl acetate. The organic layer was washed with 2N hydrochloric acid and brine successively, dried over sodium sulfate, and concentrated in vacuo. The residue was purified by the silica gel column chromatography to obtain the compound (25) (559 mg, yield 62%) as a yellow crystal.

¹H-NMR(DMSO-d₆) δ1.02(3H, t, J=7.5 Hz), 2.06(3H, s), 2.33(2H, q, J=7.5 Hz), 4.09(2H, s), 6.69(1H, d, J=7.5 Hz), 6.70(2H, s), 7.21–7.47(7H, m), 12.02(1H, br).

Example 57—Step 2

To a solution of 250 mg of the compound (25) (0.66 mmol) in 5 ml of dimethylformamide were added 275 mg of potassium carbonate (1.99 mmol), 155 mg of t-butyl bromoacetate (0.79 mmol) and 11 mg of potassium iodide (0.066 mmol), and the resulting mixture was stirred at room temperature for 15 minutes. After the reaction was completed, the resulting mixture was made acidic with 2N-hydrochloric acid and extracted with ethyl acetate. The organic layer was dried over sodium sulfate, and then removed the solvent by distillation. The residue was purified by the silica gel column chromatography to obtain the compound (26) (328 mg, yield 100%) as a yellow oil.

¹H-NMR(CDCl₃) δ1.20(3H, t, J=7.5 Hz), 1.46(9H, s), 2.19(3H, s), 2.57(2H, q, J=7.5 Hz), 3.97(2H, s), 4.04(2H, s), 6.63(1H, s), 6.69(1H, d, J=7.5 Hz), 6.74(1H, s), 7.13–7.36 (7H, m).

Example 57—Step 3

Using the compound (26) as a starting material, compound (I-57) was synthesized in a manner similar to that described in step 8 of Example 1.

¹H-NMR(CDCl₃) δ1.10(3H, t, J=7.5 Hz), 1.37(9H, s), 2.24(3H, d, J=0.9 Hz), 2.70(2H, q, J=7.5 Hz), 3.89(2H, s), 4.07(2H, s), 5.67(1H, br), 6.78(1H, d, J=7.5 Hz), 6.83(1H, d, J=0.9 Hz), 7.07(1H, br), 7.15–7.38(7H, m).

Melting point: 138–139° C.

Example 58

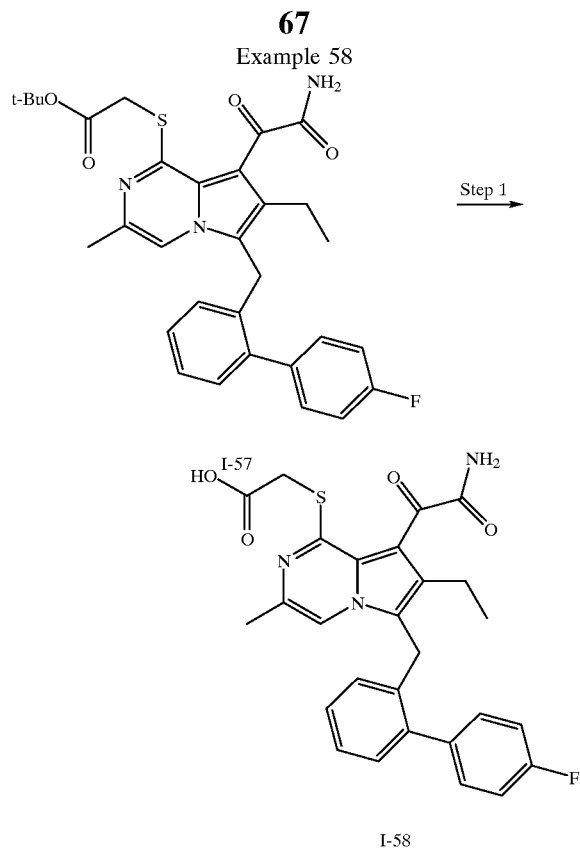

I-58

Example 58—Step 1

The compound (I-57) (46 mg, 0.082 mmol) was dissolved in 3 ml of dichloromethane. To the mixture was added 1 ml of trifluoroacetic acid, and the resulting mixture was stirred at room temperature for 4.5 hours. Trifluoroacetic acid was removed by distillation. To the residue was added water and the precipitated crystal was collected by filtration. The crystal was washed with water and dried to obtain the compound (I-58) (37 mg, yield 89%) as a yellow powder.

$^1$H-NMR(DMSO-$d_6$) δ0.86(3H, t, J=7.5 Hz), 2.25(3H, s), 2.50(2H, q, J=7.5 Hz), 3.93(2H, s), 4.20(2H, s), 6.64(1H, d, J=6.6 Hz), 7.23–7.51(7H, m), 7.48(1H, s), 7.82(1H, br), 8.20(1H, br).

Melting point: 103–105° C.

Example 59

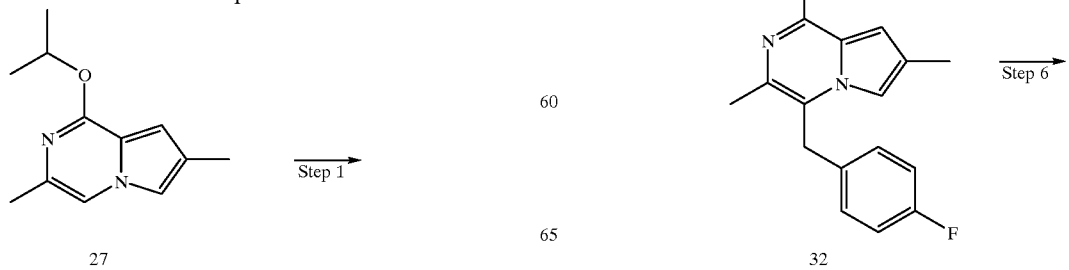

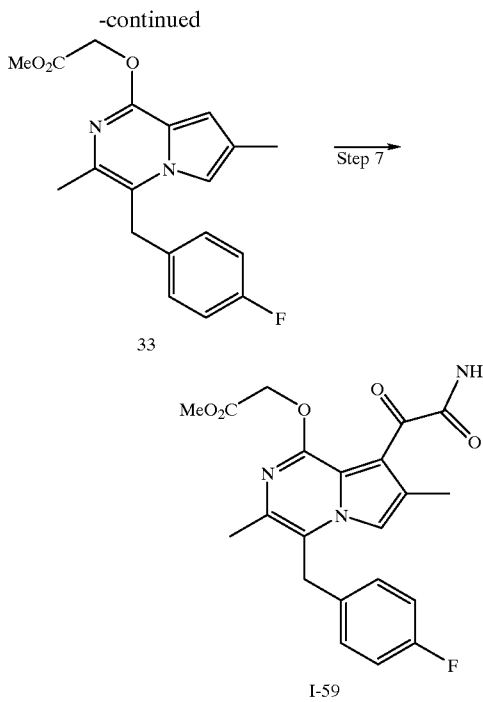

Example 59—Steps 1 to 3

To a solution of 1.01 g of the compound (27) (4.94 mmol) in 20 ml of tetrahydrofuran was added dropwise 3.90 ml of n-butyllithium in hexane (1.53 M, 5.97 mmol) at −20° C., and the resulting mixture was stirred for 30 minutes in the same condition. To the mixture was added 0.795 ml of 4-fluorobenzaldehyde (7.41 mmol) at −20° C. and the resulting mixture was stirred for 15 minutes in the same condition. To the reaction mixture were added 5 ml of aqueous ammonium chloride, 5 ml of water and ethyl acetate under ice-cooling. The organic layer was separated and the aqueous layer was extracted with ethyl acetate. The organic layer was washed with water and brine and dried over sodium sulfate. The oily residue (the compound (28)) obtained by removing the solvent by distillation under reduced pressure was subjected to the next reaction without any purification.

Chlorotrimethylsilane (7.95 ml, 62.6 mmol) was added slowly to a suspension of 9.44 g of sodium iodide (63.0 mmol) in 11 ml of acetonitrile at room temperature, and the resulting mixture was stirred for 15 minutes in the same condition. To the mixture was added slowly a solution of the compound (28) obtained above step in 15 ml of acetonitrile under ice-cooling, and the resulting mixture was stirred at room temperature for 2.75 hours. The reaction mixture was poured into a mixture of ice water and ethyl acetate to separate the organic layer. The aqueous layer was extracted with ethyl acetate. The organic layer was successively washed with 25 ml of aqueous sodium hydrogencarbonate, 25 ml of 10% sodium thiosulfate and 25 ml of brine, and dried over sodium sulfate. The oily residue (the compound (29)) obtained by removing the solvent by distillation under reduced pressure was subjected to next reaction without any purification.

To the compound (29) obtained as described above was added 15 ml of 36% hydrochloric acid at room temperature, and the resulting mixture was refluxed for 30 minutes. To the mixture was added 15 ml of water under ice-cooling. The insoluble substance was collected by filtration, washed with water, ether, and then dried under reduced pressure to obtain the compound (30) (1.08 g, yield 81% as a colorless powder.

$^1$H-NMR(CDCl$_3$) δ2.22(s, 3H), 2.44(s, 3H), 4.12(s, 2H), 7.02–7.16(m, 7H).

Example 59—Steps 4 to 5

Phosphorus oxychloride (2 ml) was added to 1.00 g of the compound (30) (3.70 mmol) at room temperature, the resulting mixture was refluxed for 15 minutes, and then excess phosphorus oxychloride was removed by distillation under reduced pressure. Ice was added to the residue, and the mixture was extracted with ethyl acetate. The organic layer was washed 2 times with 10 ml of aqueous sodium hydrogencarbonate, with 10 ml of water, and 10 ml of brine, and then dried over sodium sulfate. The crystalline residue (the compound (31)) obtained by removing the solvent by distillation under reduced pressure was subjected to next reaction without any purification.

To a suspension of the compound (31) and 1.32 g of sodium p-toluenesulfinate (7.41 mmol) in 10 ml of ethanol was added 0.11 ml of 1N hydrochloric acid (0.11 mmol) at room temperature, and the resulting mixture was refluxed for 6 hours. The reaction mixture was cooled under ice-cooling. The precipitated crystal was collected by filtration, washed 4 times with 2.5 ml of cold ethanol, and then dried under reduced pressure to obtain the compound (32) (1.28 g, yield 85%).

$^1$H-NMR(CDCl$_3$) δ2.31(s, 3H), 2.41(s, 3H), 2.54(s, 3H), 4.22(s, 2H), 6.92–7.07(m, 3H), 7.30–7.35(m, 3H), 8.02(d, J=8.4 Hz, 2H).

Example 59—Step 6

Methyl glycolate (0.675 ml, 8.57 mmol) was added slowly to a suspension of 249 mg of sodium hydride (60%, 6.21 mmol) in 10 ml of dimethylformamide under ice-cooling, and the resulting mixture was stirred at room temperature for 10 minutes. To the resulting mixture was added 1.00 g of the compound (32) (2.45 mmol) at room temperature, and the resulting mixture was stirred for 50 minutes in the same condition. The reaction mixture was poured into a mixture of 10% hydrochloric acid, ice water and ether to separate the organic layer. The aqueous layer was extracted with ether. The organic layer was washed successively with 20 ml of aqueous sodium hydrogencarbonate, 20 ml of water, and 20 ml of brine, and then dried over sodium sulfate. Hexane was added to the crystalline residue obtained by removing the solvent by distillation under reduced pressure, and the mixture was allowed to warm to produce slurry. The crystal was collected by filtration, washed with hexane, and then dried under reduced pressure to obtain the compound (33) (654 mg,, yield 78%).

$^1$H-NMR(CDCl$_3$) δ2.22(s, 3H), 2.35(s, 3H), 3.79(s, 3H), 4.14(s, 2H), 5.03(s, 2H), 6.65(dd, J=0.8, 1.4 Hz, 1H), 6.87(dd, J=0.8, 1.4 Hz, 1H), 6.96(m, 2H), 7.09(m, 2 H).

Example 59—Step 7

Oxalyl chloride (0.460 ml, 5.27 mmol) was added dropwise to a solution of 565 mg of the compound (33) (1.65 mmol) and 0.580 ml of N-methylmorpholine (5.28 mmol) in 5.5 ml of methylene chloride under ice-cooling, and the resulting mixture was stirred for 30 minutes in the same condition. The reaction mixture was poured into a mixture of 2 ml of 28% aqueous ammonia, 5 ml of ice water and ethyl acetate. The insoluble substance was removed by Celite filtration. To the filtration was added 8 ml of 10% aqueous hydrochloric acid. The organic layer was separated, washed with water and brine, dried over sodium sulfate, and concentrated in vacuo. The residue was subjected to the silica gel column chromatography. The fractions eluting with ethyl acetate were collected to obtain the compound (I-59) (35.4 mg, yield 5%) as a crystal. The resulting crystal was recrystallized from ethyl acetate and hexane. Melting point : 212–214° C.

$^1$H-NMR(CDCl$_3$) δ2.30(d, J=0.9 Hz, 3H), 2.40(s, 3H), 3.77(s, 3H), 4.18(s, 2H), 5.00(s, 2H), 5.50(brs, 1H), 6.60 (brs, 1H), 6.92(d, J=0.9 Hz, 1H), 6.95–7.11(m, 4H).

Example 60

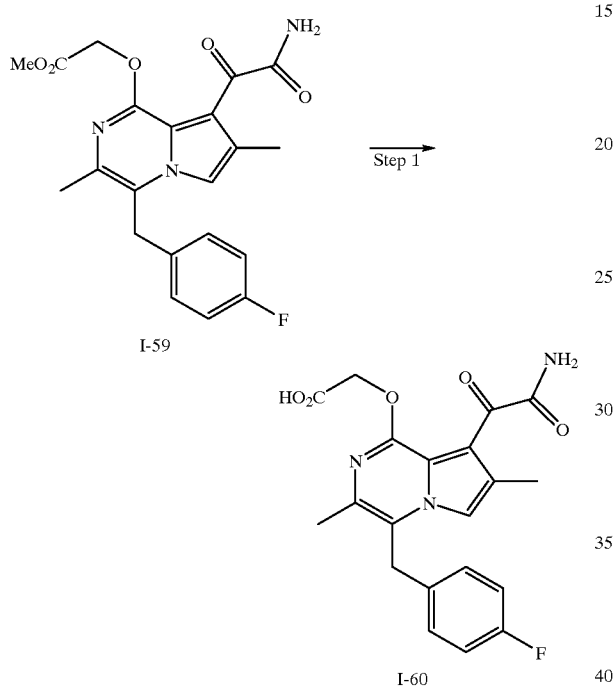

Example 60—Step 1

4N sodium hydroxide (0.0500 ml, 0.200 mmol) was added to a mixture of 19.8 mg of the compound (I-59) (0.0479 mmol), 0.5 ml of methanol and 0.5 ml of tetrahydrofuran at room temperature, and the resulting mixture was stirred for 30 minutes in the same condition. To the mixture was added 0.5 ml of 1N hydrochloric acid under ice-cooling, and the resulting mixture was extracted with ethyl acetate. The organic layer was washed with water and brine, dried over sodium sulfate, and concentrated in vacuo. The residue was recrystallized from ethyl acetate, methanol ,and hexane to obtain the compound (I-60) (19.0 mg, yield 99%) as a crystal. Melting point: 239.5–242.5° C.

$^1$H-NMR(DMSO-d$_6$) δ2.24(s, 3H), 2.38(s, 3H), 4.33(s, 2H), 4.82(s, 2H), 7.12(m, 2H), 7.24(m, 2H), 7.46(d, J=0.9 Hz, 1H), 7.48(brs, 1H), 7.85(brs, 1H).

Example 61

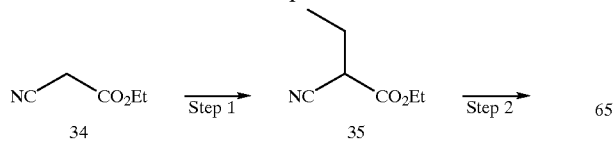

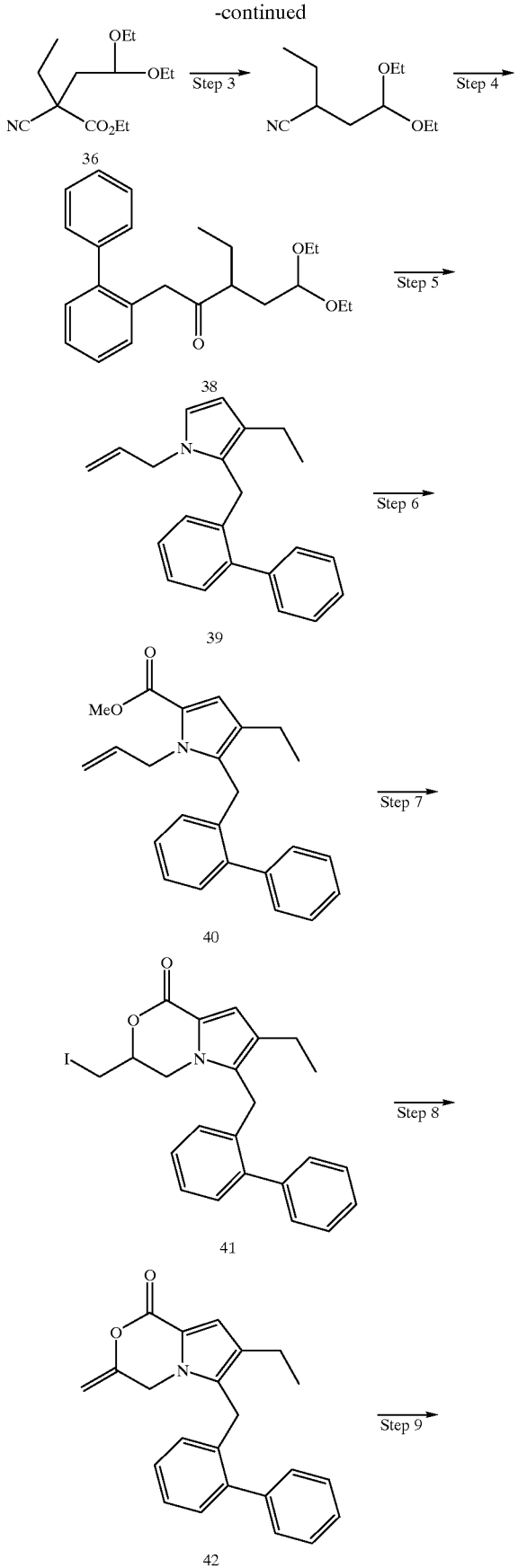

-continued

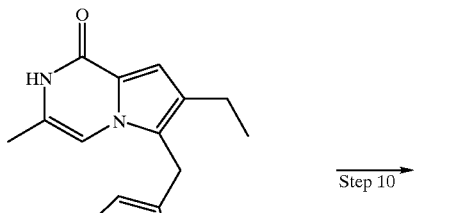

43

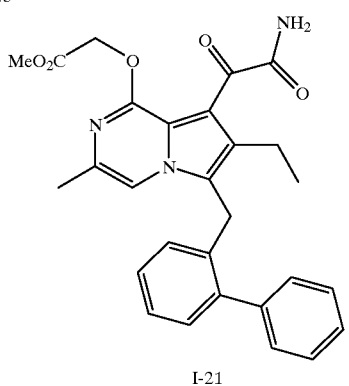

I-21

Example 61—Step 1

The compound (34) (18.2 g, 0.160 mol) and 9.43 g of 90% acetaldehyde (0.190 mol) were dissolved in 20 ml of acetic acid. To the resulting mixture was added a mixture of 300 mg of 10% palladium-carbon catalyst and 0.63 ml of piperidine (6.37 mmol) in 10 ml of acetic acid, and the mixture was stirred at room temperature for 3 hours with retaining 1 to 2 atm of pressure under hydrogen atmosphere. The catalyst was filtered off. The filtration was diluted with toluene, washed with water, and then distilled under reduced pressure to obtain the compound (35) (20.0 g, yield 88%) showing the boiling point of 92–94° C. (13 mmHg) as a colorless oil (refer to OS, III, 385, 1955; J. Am. Chem. Soc., 66, 886 1944)).

Example 61—Step 2

A mixture of 46.0 g of the compound (35) (0.326 mol), 77.1 g of bromo acetaldehyde diethylacetal (0.391 mol), 54.0 g of potassium carbonate (0.391 mol) and dimethylformamide (230 ml) was stirred with heating at 70° C. for 72 hours under nitrogen atmosphere. Dimethylformamide was removed by distillation under reduced pressure. Water was added to the residue, the mixture was extracted with toluene. The organic layer was washed with water, dried over magnesium sulfate, and the solvent was removed. The residue was distilled under reduced pressure to obtain the compound (36) showing boiling point of 105–106° C. (1 mmHg) (44.3 g, yield 56%) as a colorless oil.

$^1$H-NMR(CDCl$_3$) δ1.07(t, J=7.4 Hz, 3H), 1.18(t, J=7.0 Hz, 3H), 1.21(t, J=7.0 Hz, 3H), 1.33(t, J=7.0 Hz, 3H), 1.74–2.08(m, 3H), 2.39(dd, J=13.6, 8.2 Hz, 1H), 3.45–3.76 (m, 4H), 4.16–4.33(m, 2H), 4.77(dd, J=8.2, 4.0 Hz, 1H).

Example 61—Step 3

A mixture of 168.2 g of the compound (36) (0.691 mol), 74.6 g of potassium acetate (0.760 mol) and dimethyl sulfoxide (336 ml) was heated under nitrogen atmosphere in an oil bath at 160° C. for 15 hours. After cooling, water was added, and the mixture was extracted with ether. The organic layer was washed with water, dried over magnesium sulfate, and the solvent was removed. The residue was distilled under reduced pressure to obtain the compound (37) showing boiling point of 133–137° C. (33 mmHg) as a colorless oil (112.4 g, yield 88%).

$^1$H-NMR(CDCl$_3$) δ1.09(t, J=7.0 Hz, 3H), 1.22(t, J=7.0 Hz, 3H), 1.23(t, J=7.0 Hz, 3H), 1.58–1.99(m, 4H), 2.59–2.73 (m, 1H), 3.48–3.81(m, 4H), 4.68(dd, J=7.4, 4.2 Hz, 1H).

Example 61—Step 4

To a suspension of 1.53 g of magnesium (63.0 mmol) and 0.26 ml of 1,2-dibromoethane (3.00 mmol) in 50 ml of ether was added dropwise a solution of 12.2 g of 2-biphenylmethyl chloride (60.0 mmol) in 24 ml of ether under ice-cooling. The resulting mixture was allowed to warm to room temperature, and stirred until magnesium was dissolved. A solution of 9.26 g of the compound (37) (50.0 mmol) in 28 ml of ether was added to the mixture at room temperature, the resulting mixture was stirred for 16 hours and then refluxed for 3 hours. Aqueous solution (25 mnl) of ammonium chloride (5.35 g) as added to the reaction mixture under ice-cooling, the resulting mixture was made acidic with 63 ml of 2N sulfuric acid, and stirred under ice-cooling for 30 minutes, further at room temperature for 30 minutes. The reaction mixture was neutralized by sodium hydrogencarbonate, and extracted with toluene. The organic layer was washed with brine, dried over magnesium sulfate, and concentrated in vacuo. The residue was subjected to the silica gel chromatography. The fractions eluting with ethyl acetate: toluene (1:9) were collected to obtain the compound (38) as a colorless oil (17.6 g, yield 99%).

$^1$H-NMR(CDCl$_3$) δ0.68(t, J=7.2 Hz, 3H), 1.12(t, J=6.9 Hz, 3H), 1.15(t, J=7.2 Hz, 3H), 1.21–1.44(m, 2H), 1.50–1.62 (m, 1H), 1.87–1.96(m, 1H), 2.50(m, 1H), 3.24 —3.58(m, 4H), 3.74(d, J=16.8Hz, 1H), 3.82(d, J=16.8Hz, 1H), 4.27(t, J=6.0 Hz, 1H), 7.15— 7.42(m, 9H).

Example 61—Step 5

To a solution of 3.00 g of the compound (38) (8.50 mmol) in 30 ml of tetrahydrofuran was added 5 ml of 2N hydrochloric acid at room temperature, and the resulting mixture was stirred at the same temperature for 3 hours. The reaction mixture was poured into water, the mixture was extracted with ether, and the organic layer was washed with water, dried, and concentrated in vacuo. The residue was dissolved in 30 ml of tetrahydrofuran. To the resulting mixture was added allylamine (0.77 ml, 10.2 mmol) under ice-cooling, and the mixture was stirred at the same temperature for 1 hour. After evaporation to dryness under reduced pressure, the residue was subjected to the silica gel chromatography. The fractions eluting with hexane-hexane/ethyl acetate (50/1) were collected to obtain the compound (39) (1.92 g, yield 75%) as a colorless oil.

$^1$H-NMR (300M, CDCl$_3$): 1.15 (3H, t, J=7.8 Hz), 2.42 (2H, q, J=7.8 Hz), 3.82(2H, s), 4.00 (2H, d, J=6.0 Hz), 4.73 (1H, d, J=17.5 Hz), 4.91 (1H, d, J=10.2 Hz), 5.53 (1H, m), 6.05 (1H, s), 6.51 (1H, s), 6.87 (1H, m), 7.20–7.50 (8H, m).

Example 61—Step 6

To a solution of 200 mg of the compound (39) (0.67 mmol) in 2 ml of toluene were added 0.104 ml of methyl chlorocarbonate (1.34 mmol) and 153 mg of aluminum chloride (1.00 mmol) at room temperature, and the mixture was stirred at the same temperature for 30 minutes. The reaction mixture was. poured into water, extracted with ether, and the organic layer was washed with water, dried, and concentrated in vacuo. The residue was subjected to the silica gel column chromatography. The fractions eluting with hexane/ethyl acetate (10/1) were collected to obtain the compound (40) (140 mg, yield 59%) as a colorless oil.

$^1$H-NMR (300M, CDCl$_3$): 1.14 (3H, t, J=7.8 Hz), 2.38 (2H, q, J=7.8 Hz), 3.76 (3H, s), 3.83 (2H, s), 4.46 (1H, d, J=17.1 Hz), 4.60 (2H, m), 4.83 (1H, d, J=10.5 Hz), 5.64(1H, m), 6.82 (1H, d, J=8.1 Hz), 6.89 (1H, s), 7.20–7.50 ( 8H, s).

Example 61—Step 7

To a solution of 710 mg of the compound (40) (1.98 mmol) in 7 ml of acetonitrile was added 1.00 g of iodine (7.92 mmol) at room temperature, and the mixture was stirred at the same temperature for 20 hours. Ethyl acetate was poured into the reaction mixture, and the resulting mixture was washed with aqueous sodium sulfite, further with water, dried, and concentrated in vacuo. The residue was dissolved in hexane/ethyl acetate (1/1), and passed through the silica gel layer. The eluent was concentrated in vacuo to obtain the compound (41) (919 mg, yield 99%) as a colorless amorphous.

$^1$H-NMR (300M, CDCl$_3$): 1.13 (3H, t, J=7.5 Hz), 2.40 ( 2H, t, J=7.5 Hz), 3.15 (1H, t, J=7.59 Hz), 3.40 (2H, m), 3.80 ( 1H, m), 3.87 (1H, d, J=17.1 Hz), 3.92 (1H, d, J=17.1 Hz), 4.44 ( 1H, m), 6.87 ( 1H, m), 6.98 ( 1H, s), 7.20–7.50 ( 8H, m).

Example 61—Step 8

To a solution of 900 mg of the compound (41) (1.91 mmol) in 10 ml of toluene was added 0.43 ml of 1,8-diazabicyclo[5.4.0]-7-undecene (2.88 mmol) at room temperature, and the mixture was stirred at 80° C. for 1 hour. The solvent was removed by distillation and the residue was subjected to the silica gel chromatography. The fractions eluting with hexane/ethyl acetate (4/1)—(2/1) to obtain the compound (42) (620 mg, yield 95%) as a colorless oil.

$^1$H-NMR (CDCl$_3$) 1.12(3H, t, J=7.5 Hz), 2.37(2H, q, J=7.5 Hz), 3.91( 2H, s), 4.06(2H, s), 4.41(1H, d, J=2.1 Hz), 4.87(1H, d, J=2.1 Hz), 6.88(1H, d, J=7.5 Hz), 7.00 (1H, s), 7.30–7.50(8H, m).

Example 61—Step 9

To a solution of 550 mg of the compound (42) (1.61 mmol) in 10 ml of 99% ethanol was added 3.72 g of ammonium acetate, and the mixture was refluxed for 20 hours. The mixture was concentrated in vacuo. The residue was washed with water, dissolved in chloroform. Further, ethyl acetate was added to the mixture and concentrated. The precipitated crystal was collected by filtration to obtain the compound (43) (338 mg, yield 62%) as a colorless crystal. Melting point: 238–239° C.

$^1$H-NMR(DMSO-d$_6$) 1.02(3H, t, J=7.5Hz), 1.93(3H, s), 2.33(2H, q, J=7.5Hz), 4.03(2H, s), 6.50 (1H, s), 6.69 (1H, d, J=6.6Hz), 6.70 (1H, s), 7.20–7.50 (8H, m), 10.35 (1H, s).

Example 61—Step 10

Using the compound (43) as a starting material, compound (I-21) was synthesized in a manner similar to that described in step 6 to step 8 of Example 1.

Example 62

The compound (I-22) was synthesized by the same reaction described in Example 2 by using the compound (I-21) as a starting material.

Example 63

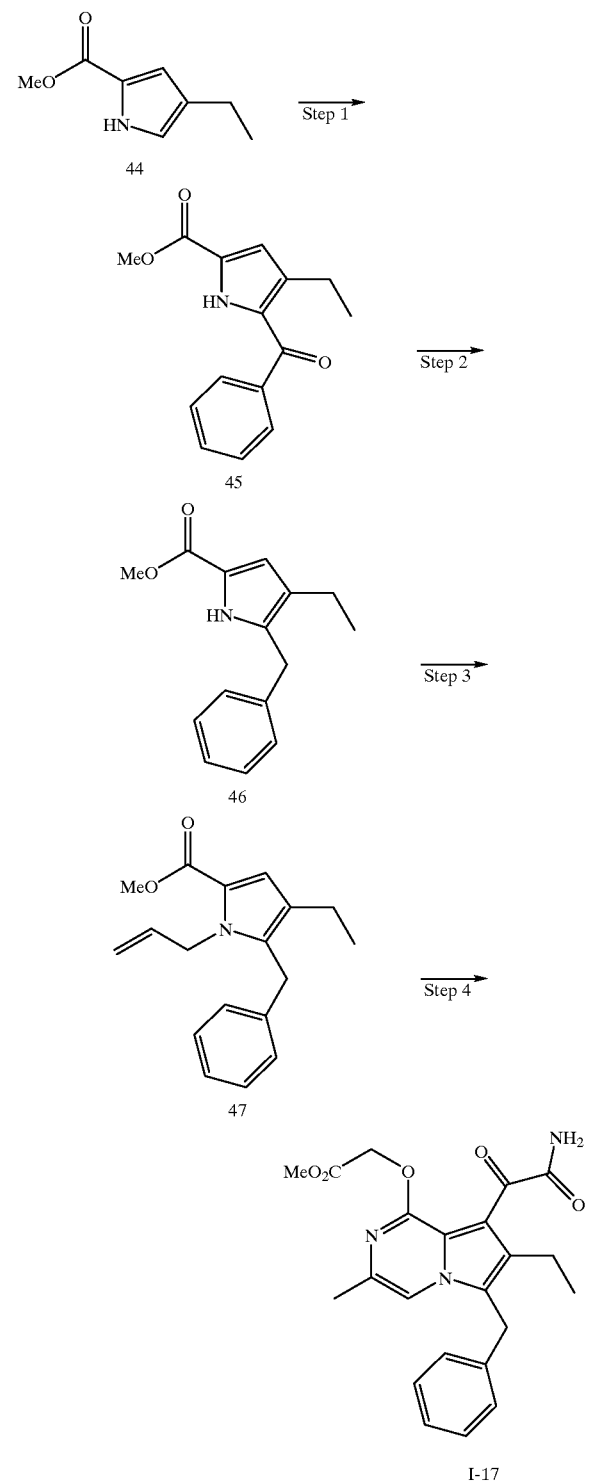

Example 63—Step 1

To a solution of 7.65 g of aluminum chloride (57.4 mmol) in 60 ml of nitromethane was added dropwise 6.65 ml of benzoyl chloride (57.3 mmol) under ice-cooling, and the mixture was stirred for 15 minutes in the same condition. To the mixture was added dropwise a solution of 2.93 g of the compound (44) (which can be synthesized in accordance with the method described in Our. J. Med. Chem., 28, 481 (1993)) in 40 ml of nitromethane under ice-cooling over 20 minutes, and the resulting mixture was stirred for 30 minutes in the same condition, further stirred at room temperature for 30 minutes. The reaction mixture was poured into a mixture of ice water and ethyl acetate to separate the organic layer. The aqueous layer was extracted with ethyl acetate. The organic layer was washed with 10 ml of 28% aqueous ammonia, 2 times with water, and with brine, dried over sodium sulfate, and concentrated in vacuo. The residue was subjected to the silica gel column chromatography. The fractions eluting with n-hexane-ethyl acetate (4:1) were collected to obtain the compound (45) (4.20 g, yield 85%,) as a colorless oil.

$^1$H-NMR(CDCl$_3$) δ1.14(t, J=7.5 Hz, 3H), 2.55(qd, J=7.5, 0.6 Hz, 2H), 3.89(s, 3H), 6.85(dt, 1H, J=2.7, 0.6 Hz), 7.46–7.53(m, 2H), 7.59(m, 1H), 7.71(m, 2H), 9.48 (brs, 1H).

Example 63—Step 2

To a solution of 776 mg of the compound (45) (3.02 mmol) in 15 ml of methanol was added 134 mg of sodium borohydride (3.55 mmol) under ice-cooling, and the mixture was stirred for 20 minutes in the same condition. Aqueous ammonium chloride (3 ml), water and ethyl acetate were added to the reaction mixture under ice-cooling to separate the organic layer. The aqueous layer was extracted with ethyl acetate. The organic layer was washed with water, brine, dried over sodium sulfate, and concentrated in vacuo. The residue was subjected to the next reaction without any purification.

To a suspension of 2.70 g of sodium iodide (18.0 mmol) in 3 ml of acetonitrile was added slowly 2.30 ml of chlorotrimethylsilane (18.1 mmol) at room temperature, and the mixture was stirred for 15 minutes in the same condition. To the mixture was added slowly a solution of the residue obtained above in 9 ml of acetonitrile under ice-cooling, and the resulting mixture was stirred at room temperature for 35 minutes. IN sodium hydroxide (10.5 ml) was added to the reaction mixture under ice-cooling, and resulting mixture was extracted 2 times with 30 ml of ethyl acetate. The organic layer was washed successively with 30 ml of 3% aqueous sodium thiosulfate, 30 ml of water, and 15 ml of brine, dried over sodium sulfate, and concentrated in vacuo. The residue was subjected to silica gel column chromatography. The fractions eluting with n-hexane-ethyl acetate (5:1) were collected to obtain the compound (46) (647 mg, yield 88%) as a colorless crystal.

$^1$H-NMR(CDCl$_3$) δ1.17(t, J=7.5 Hz, 3H), 2.45(q, J=7.5, 2H), 3.78(s, 3H), 3.94(s, 2H), 6.78(d, 1H, J=2.7 Hz), 7.12-7.17(m, 2H), 7.20-7.34(m, 3H), 8.56(brs, 1H).

Example 63—Step 3

A solution of 104 mg of the compound (46) (0.427 mmol) in 2 ml of dimethylformamide was added dropwise to 26.2 mg of sodium hydride (60%) (0.655 mmol) under ice-cooling, and the mixture was stirred at room temperature for 30 minutes. To the resulting mixture was added 0.0554 ml of allyl bromide (0.640 mmol) in the same condition, and stirred for 1 hour. Water and ether were added into the reaction mixture under ice-cooling to separate the organic layer. The aqueous layer was extracted with ether. The organic layer was washed with water and brine, dried over sodium sulfate, and concentrated in vacuo. The residue was subjected to the silica gel chromatography. The fractions eluting with n-hexane-ethyl acetate (10:1) were collected to obtain the compound (47) (80.4 mg, yield 66%) as a colorless oil. $^1$H-NMR(CDCl$_3$) δ1.16(t. J=7.5 Hz. 3H), 2.44(q, J=7.5 Hz,. 2H), 3.78(s,. 3H). 3.95(s, 2H), 4.70(ddt, J=17.1. 1.6, 1.6 Hz. 1H), 4.80(dt, J=4.8. 1.6 Hz, 2H). 5.01(ddt, J=10.2, 1.6 1.6 Hz, 1H), 5.84(ddt, J=17.1. 10.2, 4.8 Hz, 1H). 6.93(s, 1H), 7.02(m. 2H). 7.13–7.30(tm L3H).

Example 63—Step 4

The compound (I-17) was synthesized by the same reaction described in 7 to 10 step of Example 61 by using the compound (47) as a starting material.

Example 64

The compound (I-18) was synthesized by the same reaction described in Example 2 by using the compound (I-17) as a starting material.

The compounds (I-61) to (I-106) were synthesized by the same reaction described in Examples 1 to 64. The results are shown in Tables 7 to 13.

TABLE 7

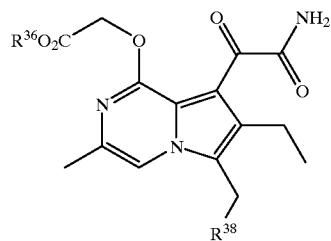

| Compound No. | $R^{36}$ | $R^{38}$ | Melting point (° C.) | $^1$H-NMR: δ CDCl$_3$($R^{36}$ = Me), DMSO-d$_6$($R^{36}$ = H) |
|---|---|---|---|---|
| I-51 | Me | 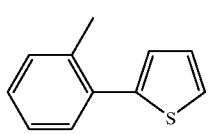 | 134.5–136 | 2.03(d, J=0.9Hz, 3H), 3.74(s, 3H), 4.03(s, 2H), 4.17(s, 2H), 4.94(s, 2H), 6.39(d, J=0.9Hz, 1H) |

TABLE 7-continued

| Compound No. | R³⁶ | R³⁸ | Melting point (°C.) | ¹H-NMR: δ CDCl₃(R³⁶ = Me), DMSO-d₆(R³⁶ = H) |
|---|---|---|---|---|
| I-52 | H | 2-methylphenyl-2-thienyl | 180.5–182.5 | 2.07(d, J=0.6Hz, 3H), 4.19(s, 2H), 4.21(s, 2H), 4.80(s, 2H), 7.04(s, 1H) |
| I-53 | Me | 2-methylphenyl-C≡C-phenyl | 147–149 | 2.13(d, J=0.9Hz, 3H), 3.74(s, 3H), 4.06(s, 2H), 4.95(s, 2H), 6.75(d, J=0.9Hz, 1H) |
| I-54 | H | 2-methylphenyl-C≡C-phenyl | 175–177 | 2.15(s, 3H), 4.18(s, 2H), 4.80(s, 2H), 7.36(s, 1H) |
| I-55 | Me | 2-methylphenyl-O-phenyl | 161–163 | 2.21(d, J=0.9Hz, 3H), 3.76(s, 3H), 4.15(s, 2H), 4.98(s, 2H) |
| I-56 | H | 2-methylphenyl-O-phenyl | 208–210 | 2.20(d, J=0.9Hz, 3H), 4.30(s, 2H), 4.81(s, 2H), 7.78(d, J=0.9Hz, 1H) |
| I-61 | Me | 2-methylphenyl-3-thienyl | 189–190 | 2.18(s, 3H), 3.75(s, 3H), 3.78(s, 3H), 4.14(s, 2H), 4.97(s, 2H), 7.06(s, 1H) |
| I-62 | H | 2-methylphenyl-3-thienyl | 200–201.5 | 2.18(d, J=0.6Hz, 3H), 3.69(s, 3H), 4.24(s, 2H), 4.80(s, 2H), 7.06(s, 1H), 7.68(d, J=0.6Hz, 1H) |
| I-63 | Me | 3-methylphenyl-(5-methyl-2-thienyl) | 179.5–181 | 2.19(d, J=0.9Hz, 3H), 3.76(s, 3H), 4.20(s, 2H), 4.97(s, 2H), 7.03(d, J=0.9Hz, 1H) |
| I-64 | H | 3-methylphenyl-(5-methyl-2-thienyl) | 190.5–193 | 2.19(d, J=0.9Hz, 3H), 4.35(s, 2H), 4.81(s, 2H), 7.74(d, J=0.9Hz, 1H) |

TABLE 7-continued
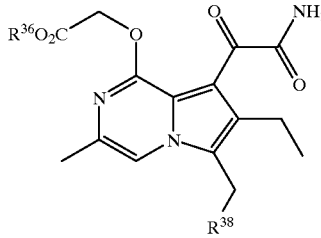
| Com-pound No. | $R^{36}$ | $R^{38}$ | Melting point (° C.) | $^1$H-NMR: δ CDCl$_3$($R^{36}$ = Me), DMSO-d$_6$($R^{36}$ = H) |
|---|---|---|---|---|
*measured with DMSO-d$_6$
TABLE 8
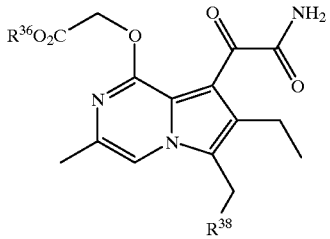
| Com-pound No. | $R^{36}$ | $R^{38}$ | Melting point (° C.) | $^1$H-NMR: δ CDCl$_3$($R^{36}$ = Me), DMSO-d$_6$($R^{36}$ = H) |
|---|---|---|---|---|
| I-65 | Me | 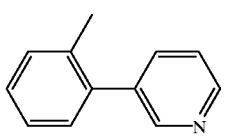 | | *2.14(d, J=0.6Hz, 3H), 3.67(s, 3H), 4.22(s, 2H), 4.88(s, 2H), 7.31(d, J=0.6Hz, 1H) |
| I-66 | H | 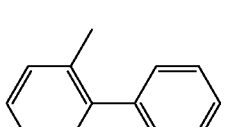 | | 2.15(s, 3H), 4.21(s, 2H), 4.72(s, 2H), 7.38(s, 1H) |
| I-67 | Me | 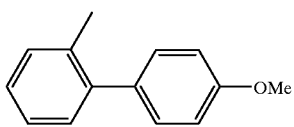 | | 2.12(d, J=1.2Hz, 3H), 3.74(s, 3H), 3.88(s, 3H), 4.09(s, 2H), 4.94(s, 2H), 6.76(d, J=12Hz, 1H) |
| I-68 | H | 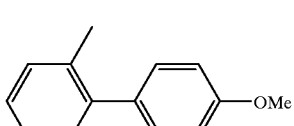 | | 2.14(s, 3H), 3.80(s, 3H), 4.20(s, 2H), 4.79(s, 2H), 7.32(s, 1H) |
| I-69 | Me | 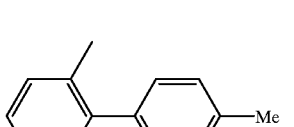 | 167.5–169.5 | 2.17(d, J=0.9Hz, 3H), 2.44(s, 3H), 3.74(s, 3H), 4.09(s, 2H), 4.94(s, 2H), 6.76(d, J=0.9Hz, 1H) |

TABLE 8-continued
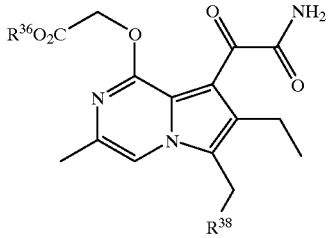
| Compound No. | R³⁶ | R³⁸ | Melting point (° C.) | ¹H-NMR: δ CDCl₃(R³⁶ = Me), DMSO-d₆(R³⁶ = H) |
|---|---|---|---|---|
| I-70 | H | 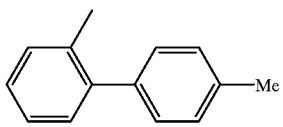 | 179.5–181.5 | 2.14(s, 3H), 2.36(s, 3H), 4.19 (s, 2H), 4.79(s, 2H), 7.34(s, 1H) |
| I-71 | Me | 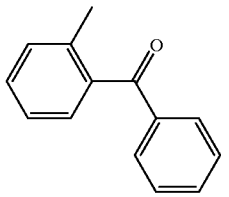 | 190–192 | 2.16(d, J=0.6Hz, 3H), 3.75(s, 3H), 4.27(s, 2H), 4.95(s, 2H), 7.20(d, J=0.6Hz, 1H) |
| I-72 | H | 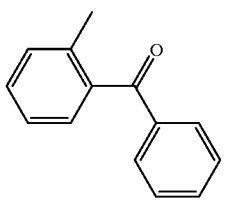 | 131–133 | 2.14(s, 3H), 4.32(s, 2H), 4.79 (s, 2H), 7.39(s, 1H) |
| I-73 | Me | 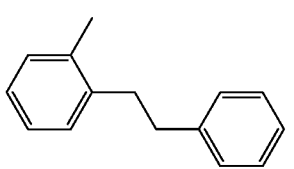 | 215–217 | *2.14(d, J=0.9Hz, 3H), 3.67(s, 3H), 4.22(s, 2H), 4.90(s, 2H), 7.44(d, J=0.9Hz, 1H) |
| I-74 | H | 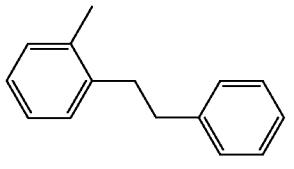 | 189–191 | 2.15(s, 3H), 4.21(s, 2H), 4.82 (s, 2H), 7.40(s, 1H) |
*measured with DMSO-d₆

TABLE 9
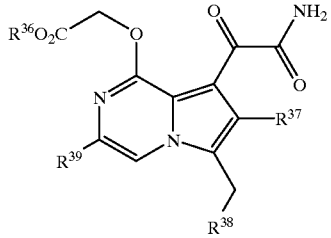
| Compound No. | $R^{36}$ | $R^{37}$ | $R^{38}$ | $R^{39}$ | Melting point (° C.) | $^1$H-NMR: δ CDCl$_3$($R^{36}$ = Me), DMSO-d$_6$($R^{36}$ = H) |
|---|---|---|---|---|---|---|
| I-75 | Me | cyclo-propyl | 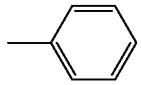 | Me | 210–211.5 | 2.15(d, J=0.9Hz, 3H), 3.74(s, 3H), 4.34(s, 2H), 4.96(s, 2H), 6.99 (d, J=0.9Hz, 1H) |
| I-76 | H | cyclo-propyl | 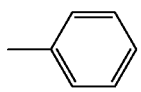 | Me | 194.5–196 | 2.15(d, J=0.6Hz, 3H), 4.38(s, 2H), 4.79(s, 2H), 7.62(d, J=0.6Hz, 1H) |
| I-77 | Me | cyclo-propyl | 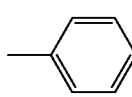 | Me | 179–182.5 | 2.16(1, J=0.9Hz, 3H), 3.75(s, 3H), 4.31(s, 2H), (s, 2H), 6.96 (d, J=0.9Hz, 1H) |
| I-78 | H | cyclo-propyl | 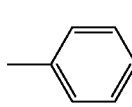 | Me | 185–187 | 2.16(d, J=0.9Hz, 3H), 4.37(s, 2H), 4.79(s, 2H), 7.64(d, J=0.9Hz, 1H) |
| I-79 | Me | Et | 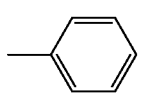 | 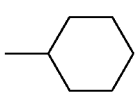 | 193–194 | 3.74(s, 3H), 4.21(s, 2H), 4.93(s, 2H), 7.05 (s, 1H) |
| I-80 | H | Et | 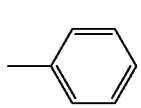 | 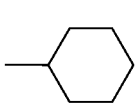 | 227–230 | 4.34(s, 3H), 4.77(s, 2H), 7.58(s, 1H) |
| I-81 | Me | Et | 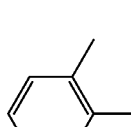 | 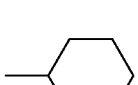 | 161.5–162.5 | 3.72(s, 3H), 4.10(s, 2H) 4.90(s, 2H), 6.74 (s, 1H) |
| I-82 | H | Et | 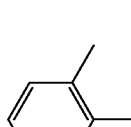 | 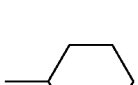 | 200–201.5 | 4.23(s, 3H), 4.76(s, 2H), 7.48(s, 1H) |

TABLE 10
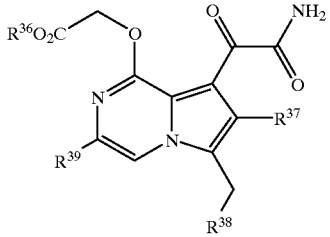
| Compound No. | R36 | R37 | R38 | R39 | Melting point (° C.) | 1H-NMR: δ CDCl3(R36 = Me), DMSO-d6(R36 = H) |
|---|---|---|---|---|---|---|
| I-83 | Me | Me | ⟨phenyl⟩ | Me | 205–207 | 2.18(d, J=1.2Hz, 3H), 2.42(s, 3H), 3.74(s, 3H), 4.19(s, 2H), 4.97(s, 2H), 7.11(d, J=1.2 Hz, 1H) |
| I-84 | H | Me | ⟨phenyl⟩ | Me | 199.5–201 | 2.19(d, J=0.9Hz, 3H), 2.34(s, 3H), 4.31(s, 2H), 4.81(s, 2H), 7.77(d, J=0.9Hz, 1H) |
| I-85 | Me | Et | ⟨5-methylthiophen-2-yl⟩ | Me | 203–204 | 2.23(d, J=1.2Hz, 3H), 2.40(s, 3H), 3.75(s, 3H), 4.25(s, 2H), 4.97(s, 2H), 7.22(d, J=1.2 Hz, 1H) |
| I-86 | H | Et | ⟨5-methylthiophen-2-yl⟩ | Me | 216.5–218 | 2.21(s, 3H), 2.32(s, 3H), 4.41(s, 2H), 4.80(s, 2H), 7.78(s, 1H) |
| I-87 | Me | Et | ⟨benzothiophen-3-yl⟩ | Me | 186–187 | 2.16(d, J=0.9Hz, 3H), 3.77(s, 3H), 4.32(d, J=1.5Hz, 2H), 4.99(s, 2H), 6.61(s, 1H), 7.05(d, J=0.9Hz, 1H) |
| I-88 | H | Et | ⟨benzothiophen-3-yl⟩ | Me | 211–213 | 2.17(s, 3H), 4.50(s, 2H), 4.82(s, 2H), 6.80(s, 1H), 7.72(s, 1H) |

TABLE 11
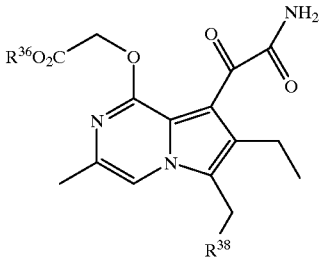
| Compound No. | R³⁶ | R³⁸ | Melting point (° C.) | ¹H-NMR(CDCl₃):δ |
|---|---|---|---|---|
| I-89 | Et |  | 184–186 | 1.81(t, J=7.8Hz, 3H), 2.18(s, 3H), 4.17(s, 2H), 4.22(q, J=7.8 Hz, 2H), 4.94(s, 2H), 6.96(s, 1H) |
| I-90 | Et | 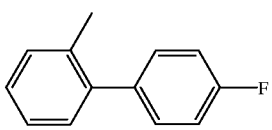 | 172–173 | 1.26(t, J=7.2Hz, 3H), 2.13(s, 3H), 4.05(s, 2H), 4.21(q, J=7.2 Hz, 2H), 4.92(s, 2H), 6.75(s, 1H) |
| I-91 | Et | 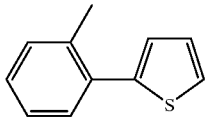 | 160–161 | 1.26(t, J=7.2Hz, 3H), 2.14(d, J=1.2Hz, 3H), 4.21(q, J=7.2 Hz, 2H), 4.25(s, 2H), 4.93(s, 2H), 6.85(d, J=1.2Hz, 1H) |
| I-92 | Et | 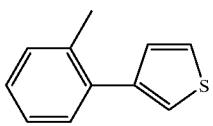 | 185–186 | 1.26(t, J=7.2Hz, 3H), 2.13(d, J=0.9Hz, 3H), 4.16(s, 2H), 4.22 (q, J=7.2Hz, 2H), 4.92(s, 2H), 6.79(d, J=0.9Hz, 1H) |
| I-93 | Pr |  | 182–183 | 0.89(t, J=7.5Hz, 3H), 1.63(m, 2H), 2.17(s, 3H), 4.12(t, J=6.6 Hz, 2H), 4.17(s, 2H), 4.95(s, 2H), 6.97(s, 1H) |
| I-94 | Pentyl |  | 175–176 | 0.88(t, J=6.9Hz, 3H), 1.29(m, 4H), 1.62(m, 2H), 2.17(s, 3H), 4.15(t, J=6.6Hz, 2H), 4.17(s, 2H), 4.95(s, 2H), 6.97(s, 1H) |
| I-95 | 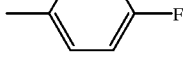 | 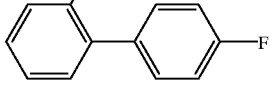 | 139–140 | 2.19(s, 3H), 2.50(m, 4H), 2.66 (t, J=5.7Hz, 2H), 3.71(t, J=4.5 Hz, 4H), 4.17(s, 2H), 4.30(t, J=5.7Hz, 2H), 5.03(s, 2H), 6.97 (s, 1H) |
| I-96 | | | | 2.14(s, 3H), 2.50(m, 4H), 2.66 (m, 2H), 3.70(m, 4H), 4.06(s, 2H), 4.30(t, J=5.4Hz, 2H), 5.01 (s, 2H), 6.75(s, 1H) |

TABLE 12

| Compound No. | R³⁶ | R³⁸ | Melting point (° C.) | ¹H-NMR(CDCl₃):δ |
|---|---|---|---|---|
| I-97 | morpholine-N-propyl | 2-methylphenyl-thiophen-2-yl | | 2.15(s, 3H), 2.49(m, 4H), 2.65 (t, J=5.4Hz, 2H), 3.70(m, 4H), 4.26(s, 2H), 4.29(t, J=5.4Hz, 2H), 5.01(s, 2H), 6.85(s, 1H) |
| I-98 | morpholine-N-propyl | 2-methylphenyl-thiophen-3-yl | | 2.13(d, J=0.9Hz, 3H), 2.40–2.80(m 6H), 3.66–3.78(m, 4H), 4.16(s, 2H), 4.26–4.36(m, 2H), 5.01(s, 2H), 6.80(d, J=0.9Hz, 1H) |
| I-99 | Na | 4-fluoro-methylphenyl | 250–265 | *2.18(s, 3H), 4.28(s, 2H), 4.81 (s, 2H), 7.31(s, 1H) |
| I-100 | Na | 2-methyl-4'-fluorobiphenyl | | **2.14(d, J=0.9Hz, 3H), 4.14 (s, 2H), 4.79(s, 2H), 6.99(d, J=0.9Hz, 1H) |
| I-101 | Na | 2-methylphenyl-thiophen-2-yl | | *2.15(d, J=0.9Hz, 3H), 4.32(s, 2H), 4.80(s, 2H), 7.05(d, J=0.9 Hz, 1H) |
| I-102 | Na | 2-methylphenyl-thiophen-3-yl | 260–263 | **2.12(d, J=0.9Hz, 3H), 4.25 (s, 2H), 4.42(s, 2H), 7.21(m, 1H) |

*measured with CD₃OD
**measured with DMSO-d₆

TABLE 13

| Compound No. | R³⁶ | Melting point (° C.) | ¹H-NMR(CDCl₃):δ |
|---|---|---|---|
| I-103 | Me-C(=O)-O-ethyl | 147–148 | 2.12(s, 3H), 2.18(s, 3H), 4.18 (s, 2H), 5.01(s, 2H), 5.81(s, 2H), 6.97(s, 1H) |

TABLE 13-continued

| Compound No. | R³⁶ | Melting point (° C.) | ¹H-NMR(CDCl₃):δ |
|---|---|---|---|
| I-104 | (pivaloyloxymethyl group: tBu-C(O)-O-CH₂-) | 143–144 | 1.20(s, 9H), 2.17(s, 3H), 4.17 (s, 2H), 5.01(s, 2H), 5.81(s, 2H), 6.97(s, 1H) |
| I-105 | MeO-C(O)-O-CH₂- | 148–150 | 2.18(s, 3H), 3.83(s, 3H), 4.17 (s, 2H), 5.02(s, 2H), 5.83(s, 2H), 6.97(s, 1H) |
| I-106 | cyclohexyl-O-C(O)-O-CH(Me)- | 125–130 | 1.10–2.00(m, 10H), 1.53(d, J=5.7Hz, 3H), 2.18(s, 3H), 4.17 (s, 2H), 4.65(m, 1H), 4.94(d, J=15.9Hz, 1H), 5.00(d, J=15.9 Hz, 1H), 6.82(q, J=5.7Hz, 1H), 6.98(s, 1H) |

The compounds shown in the following Tables 14 to 25 can be synthesized in accordance with the same method describe in the above Examples. The abbreviations used in Tables 14 to 25: AA, AB, AC, AD, AE, AF, AG, BA, BB, BC, BD, BE, BF, BG, BH, BI, BJ, BK, BL, BM, BN, BO, BP, BQ, BR, BS, BT, BU, BV, BW, BX, BY, BZ, CA, CB, CC, CD, CE, CF, CG, CH, CI, CJ, CK, CL, CM, and CN show the substituents described as follows.

AA: phenyl

AB: pyridin-CH₂-

AC: 4-MeO-C₆H₄-CH₂-

AD: 2-biphenyl-CH₂-

AE: 3-biphenyl-CH₂-

AF: 4-biphenyl-CH₂-

AG: phenyl-CH₂CH₂-

BA: 2-methyl-3-phenyl-thiophene

BB: 2-methyl-3-(4-fluorophenyl)-thiophene

-continued
BC 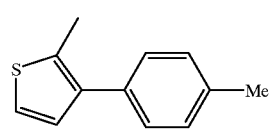
BD 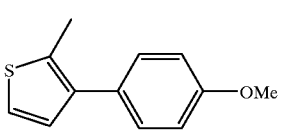
BE 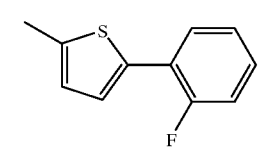
BF 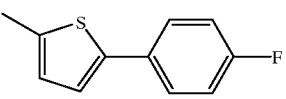
BG 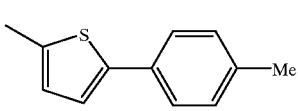
BH 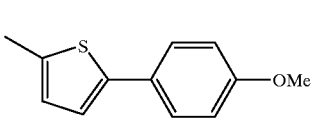
BI 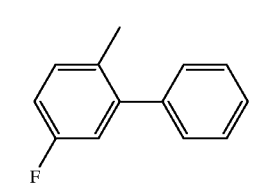
BJ 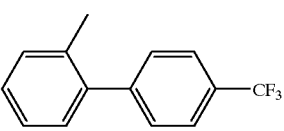
BK 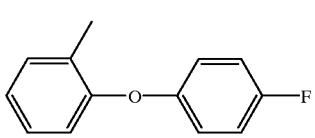
BL 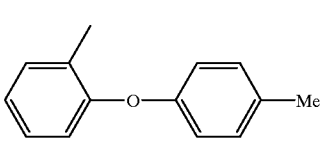
BM 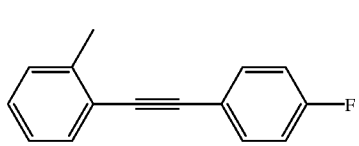
-continued
BN 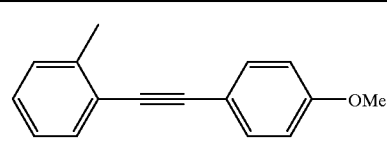
BO 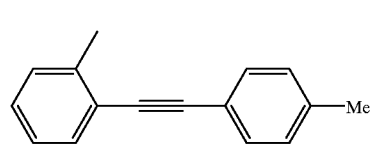
BP 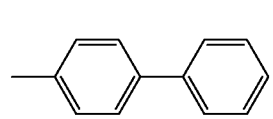
BQ 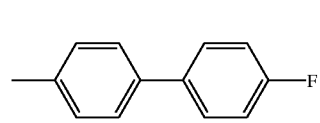
BR 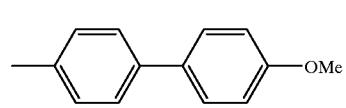
BS 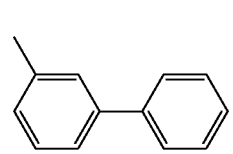
BT 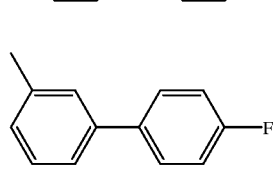
BU 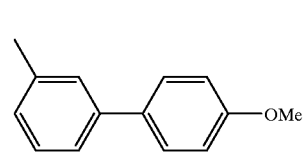
BV 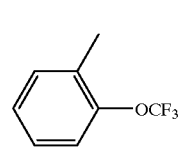
BW 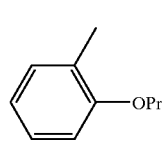
BX 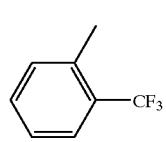

-continued
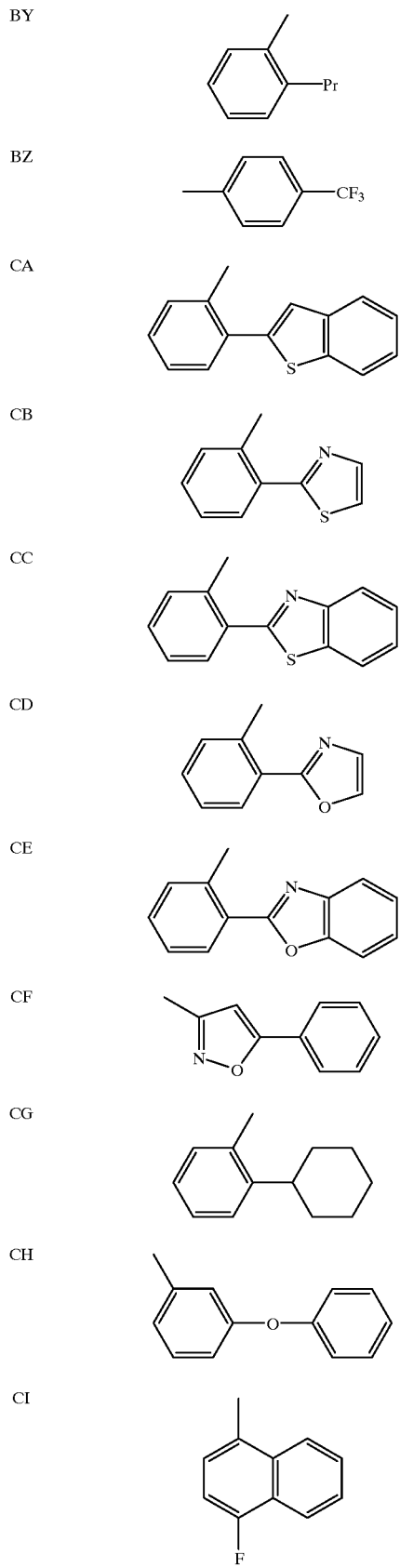
-continued
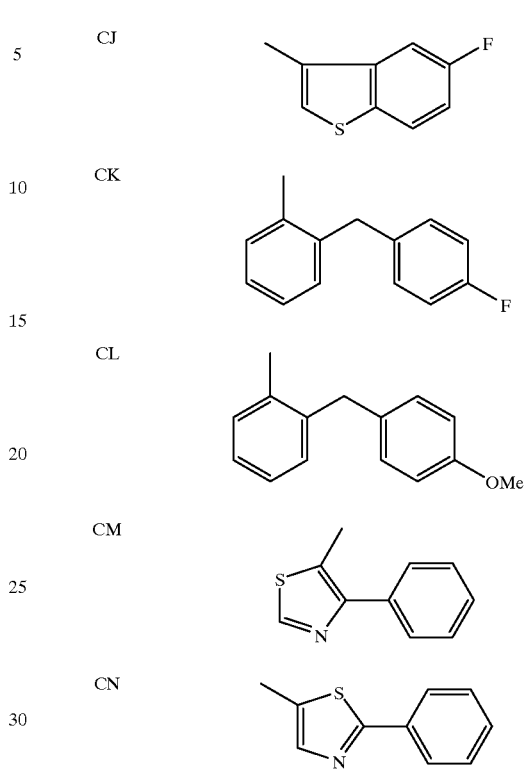
TABLE 14
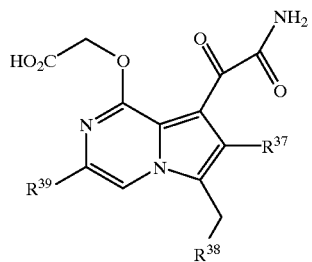
| Compound No. | R³⁷ | R³⁸ | R³⁹ |
|---|---|---|---|
| II-1 | Me | BA | Me |
| II-2 | Me | BB | Me |
| II-3 | Me | BC | Me |
| II-4 | Me | BD | Me |
| II-5 | Me | BE | Me |
| II-6 | Me | BF | Me |
| II-7 | Me | BG | Me |
| II-8 | Me | BH | Me |
| II-9 | Me | BI | Me |
| II-10 | Me | BJ | Me |
| II-11 | Me | BK | Me |
| II-12 | Me | BL | Me |
| II-13 | Me | BM | Me |
| II-14 | Me | BN | Me |
| II-15 | Me | BO | Me |
| II-16 | Me | BP | Me |
| II-17 | Me | BQ | Me |
| II-18 | Me | BR | Me |
| II-19 | Me | BS | Me |
| II-20 | Me | BT | Me |
| II-21 | Me | BU | Me |

TABLE 14-continued

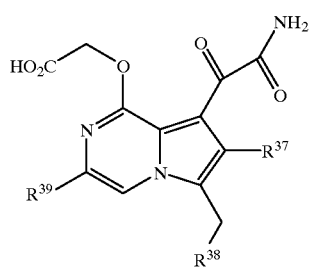

| Compound No. | R³⁷ | R³⁸ | R³⁹ |
|---|---|---|---|
| II-22 | Me | BV | Me |
| II-23 | Me | BW | Me |
| II-24 | Me | BX | Me |
| II-25 | Me | BY | Me |
| II-26 | Me | BZ | Me |
| II-27 | Me | CA | Me |
| II-28 | Me | CB | Me |
| II-29 | Me | CC | Me |
| II-30 | Me | CD | Me |
| II-31 | Me | CE | Me |
| II-32 | Me | CF | Me |
| II-33 | Me | CG | Me |
| II-34 | Me | CH | Me |
| II-35 | Me | CI | Me |
| II-36 | Me | CJ | Me |
| II-37 | Me | CK | Me |
| II-38 | Me | CL | Me |
| II-39 | Me | CM | Me |
| II-40 | Me | CN | Me |
| II-41 | Et | BA | Me |
| II-42 | Et | BB | Me |
| II-43 | Et | BC | Me |
| II-44 | Et | BD | Me |
| II-45 | Et | BE | Me |
| II-46 | Et | BF | Me |
| II-47 | Et | BG | Me |
| II-48 | Et | BH | Me |
| II-49 | Et | BI | Me |
| II-50 | Et | BJ | Me |
| II-51 | Et | BK | Me |
| II-52 | Et | BL | Me |
| II-53 | Et | BM | Me |
| II-54 | Et | BN | Me |
| II-55 | Et | BO | Me |
| II-56 | Et | BP | Me |
| II-57 | Et | BQ | Me |
| II-58 | Et | BR | Me |
| II-59 | Et | BS | Me |
| II-60 | Et | BT | Me |
| II-61 | Et | BU | Me |
| II-62 | Et | BV | Me |
| II-63 | Et | BW | Me |
| II-64 | Et | BX | Me |
| II-65 | Et | BY | Me |
| II-66 | Et | BZ | Me |
| II-67 | Et | CA | Me |
| II-68 | Et | CB | Me |
| II-69 | Et | CC | Me |
| II-70 | Et | CD | Me |
| II-71 | Et | CE | Me |
| II-72 | Et | CF | Me |
| II-73 | Et | CG | Me |
| II-74 | Et | CH | Me |
| II-75 | Et | CI | Me |
| II-76 | Et | CJ | Me |
| II-77 | Et | CK | Me |
| II-78 | Et | CL | Me |
| II-79 | Et | CM | Me |
| II-80 | Et | CN | Me |
| II-81 | Ph | BA | Me |
| II-82 | Ph | BB | Me |
| II-83 | Ph | BC | Me |

TABLE 14-continued

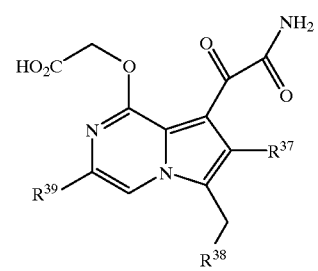

| Compound No. | R³⁷ | R³⁸ | R³⁹ |
|---|---|---|---|
| II-84 | Ph | BD | Me |
| II-85 | Ph | BE | Me |
| II-86 | Ph | BF | Me |
| II-87 | Ph | BG | Me |
| II-88 | Ph | BH | Me |
| II-89 | Ph | BI | Me |
| II-90 | Ph | BJ | Me |
| II-91 | Ph | BK | Me |
| II-92 | Ph | BL | Me |
| II-93 | Ph | BM | Me |
| II-94 | Ph | BN | Me |
| II-95 | Ph | BO | Me |
| II-96 | Ph | BP | Me |
| II-97 | Ph | BQ | Me |
| II-98 | Ph | BR | Me |
| II-99 | Ph | BS | Me |
| II-100 | Ph | BT | Me |
| II-101 | Ph | BU | Me |
| II-102 | Ph | BV | Me |
| II-103 | Ph | BW | Me |
| II-104 | Ph | BX | Me |
| II-105 | Ph | BY | Me |
| II-106 | Ph | BZ | Me |
| II-107 | Ph | CA | Me |
| II-108 | Ph | CB | Me |
| II-109 | Ph | CC | Me |
| II-110 | Ph | CD | Me |
| II-111 | Ph | CE | Me |
| II-112 | Ph | CF | Me |
| II-113 | Ph | CG | Me |
| II-114 | Ph | CH | Me |
| II-115 | Ph | CI | Me |
| II-116 | Ph | CJ | Me |
| II-117 | Ph | CK | Me |
| II-118 | Ph | CL | Me |
| II-119 | Ph | CM | Me |
| II-120 | Ph | CN | Me |

TABLE 15

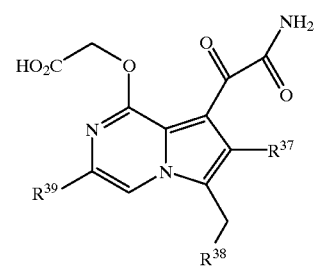

| Compound No. | R³⁷ | R³⁸ | R³⁹ |
|---|---|---|---|
| II-121 | Me | BA | Et |
| II-122 | Me | BB | Et |
| II-123 | Me | BC | Et |

TABLE 15-continued

| Compound No. | $R^{37}$ | $R^{38}$ | $R^{39}$ |
|---|---|---|---|
| II-124 | Me | BD | Et |
| II-125 | Me | BE | Et |
| II-126 | Me | BF | Et |
| II-127 | Me | BG | Et |
| II-128 | Me | BH | Et |
| II-129 | Me | BI | Et |
| II-130 | Me | BJ | Et |
| II-131 | Me | BK | Et |
| II-132 | Me | BL | Et |
| II-133 | Me | BM | Et |
| II-134 | Me | BN | Et |
| II-135 | Me | BO | Et |
| II-136 | Me | BP | Et |
| II-137 | Me | BQ | Et |
| II-138 | Me | BR | Et |
| II-139 | Me | BS | Et |
| II-140 | Me | BT | Et |
| II-141 | Me | BU | Et |
| II-142 | Me | BV | Et |
| II-143 | Me | BW | Et |
| II-144 | Me | BX | Et |
| II-145 | Me | BY | Et |
| II-146 | Me | BZ | Et |
| II-147 | Me | CA | Et |
| II-148 | Me | CB | Et |
| II-149 | Me | CC | Et |
| II-150 | Me | CD | Et |
| II-151 | Me | CE | Et |
| II-152 | Me | CF | Et |
| II-153 | Me | CG | Et |
| II-154 | Me | CH | Et |
| II-155 | Me | CI | Et |
| II-156 | Me | CJ | Et |
| II-157 | Me | CK | Et |
| II-158 | Me | CL | Et |
| II-159 | Me | CM | Et |
| II-160 | Me | CN | Et |
| II-161 | Et | BA | Et |
| II-162 | Et | BB | Et |
| II-163 | Et | BC | Et |
| II-164 | Et | BD | Et |
| II-165 | Et | BE | Et |
| II-166 | Et | BF | Et |
| II-167 | Et | BG | Et |
| II-168 | Et | BH | Et |
| II-169 | Et | BI | Et |
| II-170 | Et | BJ | Et |
| II-171 | Et | BK | Et |
| II-172 | Et | BL | Et |
| II-173 | Et | BM | Et |
| II-174 | Et | BN | Et |
| II-175 | Et | BO | Et |
| II-176 | Et | BP | Et |
| II-177 | Et | BQ | Et |
| II-178 | Et | BR | Et |
| II-179 | Et | BS | Et |
| II-180 | Et | BT | Et |
| II-181 | Et | BU | Et |
| II-182 | Et | BV | Et |
| II-183 | Et | BW | Et |
| II-184 | Et | BX | Et |
| II-185 | Et | BY | Et |
| II-186 | Et | BZ | Et |
| II-187 | Et | CA | Et |
| II-188 | Et | CB | Et |
| II-189 | Et | CC | Et |
| II-190 | Et | CD | Et |
| II-191 | Et | CE | Et |
| II-192 | Et | CF | Et |
| II-193 | Et | CG | Et |
| II-194 | Et | CH | Et |
| II-195 | Et | CI | Et |
| II-196 | Et | CJ | Et |
| II-197 | Et | CK | Et |
| II-198 | Et | CL | Et |
| II-199 | Et | CM | Et |
| II-200 | Et | CN | Et |
| II-201 | Ph | BA | Et |
| II-202 | Ph | BB | Et |
| II-203 | Ph | BC | Et |
| II-204 | Ph | BD | Et |
| II-205 | Ph | BE | Et |
| II-206 | Ph | BF | Et |
| II-207 | Ph | BG | Et |
| II-208 | Ph | BH | Et |
| II-209 | Ph | BI | Et |
| II-210 | Ph | BJ | Et |
| II-211 | Ph | BK | Et |
| II-212 | Ph | BL | Et |
| II-213 | Ph | BM | Et |
| II-214 | Ph | BN | Et |
| II-215 | Ph | BO | Et |
| II-216 | Ph | BP | Et |
| II-217 | Ph | BQ | Et |
| II-218 | Ph | BR | Et |
| II-219 | Ph | BS | Et |
| II-220 | Ph | BT | Et |
| II-221 | Ph | BU | Et |
| II-222 | Ph | BV | Et |
| II-223 | Ph | BW | Et |
| II-224 | Ph | BX | Et |
| II-225 | Ph | BY | Et |
| II-226 | Ph | BZ | Et |
| II-227 | Ph | CA | Et |
| II-228 | Ph | CB | Et |
| II-229 | Ph | CC | Et |
| II-230 | Ph | CD | Et |
| II-231 | Ph | CE | Et |
| II-232 | Ph | CF | Et |
| II-233 | Ph | CG | Et |
| II-234 | Ph | CH | Et |
| II-235 | Ph | CI | Et |
| II-236 | Ph | CJ | Et |
| II-237 | Ph | CK | Et |
| II-238 | Ph | CL | Et |
| II-239 | Ph | CM | Et |
| II-240 | Ph | CN | Et |

TABLE 16

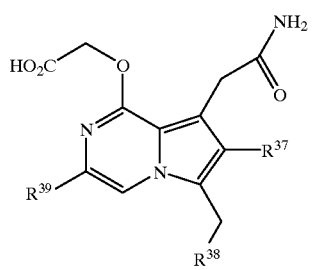

| Compound No. | R37 | R38 | R39 |
|---|---|---|---|
| II-241 | Me | BA | Me |
| II-242 | Me | BB | Me |
| II-243 | Me | BC | Me |
| II-244 | Me | BD | Me |
| II-245 | Me | BE | Me |
| II-246 | Me | BF | Me |
| II-247 | Me | BG | Me |
| II-248 | Me | BH | Me |
| II-249 | Me | BI | Me |
| II-250 | Me | BJ | Me |
| II-251 | Me | BK | Me |
| II-252 | Me | BL | Me |
| II-253 | Me | BM | Me |
| II-254 | Me | BN | Me |
| II-255 | Me | BO | Me |
| II-256 | Me | BP | Me |
| II-257 | Me | BQ | Me |
| II-258 | Me | BR | Me |
| II-259 | Me | BS | Me |
| II-260 | Me | BT | Me |
| II-261 | Me | BU | Me |
| II-262 | Me | BV | Me |
| II-263 | Me | BW | Me |
| II-264 | Me | BX | Me |
| II-265 | Me | BY | Me |
| II-266 | Me | BZ | Me |
| II-267 | Me | CA | Me |
| II-268 | Me | CB | Me |
| II-269 | Me | CC | Me |
| II-270 | Me | CD | Me |
| II-271 | Me | CE | Me |
| II-272 | Me | CF | Me |
| II-273 | Me | CG | Me |
| II-274 | Me | CH | Me |
| II-275 | Me | CI | Me |
| II-276 | Me | CJ | Me |
| II-277 | Me | CK | Me |
| II-278 | Me | CL | Me |
| II-279 | Me | CM | Me |
| II-280 | Me | CN | Me |
| II-281 | Et | BA | Me |
| II-282 | Et | BB | Me |
| II-283 | Et | BC | Me |
| II-284 | Et | BD | Me |
| II-285 | Et | BE | Me |
| II-286 | Et | BF | Me |
| II-287 | Et | BG | Me |
| II-288 | Et | BH | Me |
| II-289 | Et | BI | Me |
| II-290 | Et | BJ | Me |
| II-291 | Et | BK | Me |
| II-292 | Et | BL | Me |
| II-293 | Et | BM | Me |
| II-294 | Et | BN | Me |
| II-295 | Et | BO | Me |
| II-296 | Et | BP | Me |
| II-297 | Et | BQ | Me |
| II-298 | Et | BR | Me |
| II-299 | Et | BS | Me |
| II-300 | Et | BT | Me |
| II-301 | Et | BU | Me |
| II-302 | Et | BV | Me |

TABLE 16-continued

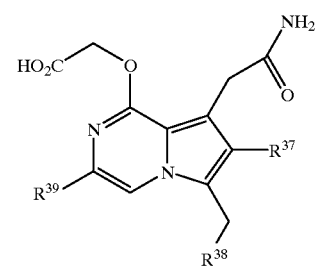

| Compound No. | R37 | R38 | R39 |
|---|---|---|---|
| II-303 | Et | BW | Me |
| II-304 | Et | BX | Me |
| II-305 | Et | BY | Me |
| II-306 | Et | BZ | Me |
| II-307 | Et | CA | Me |
| II-308 | Et | CB | Me |
| II-309 | Et | CC | Me |
| II-310 | Et | CD | Me |
| II-311 | Et | CE | Me |
| II-312 | Et | CF | Me |
| II-313 | Et | CG | Me |
| II-314 | Et | CH | Me |
| II-315 | Et | CI | Me |
| II-316 | Et | CJ | Me |
| II-317 | Et | CK | Me |
| II-318 | Et | CL | Me |
| II-319 | Et | CM | Me |
| II-320 | Et | CN | Me |
| II-321 | Ph | BA | Me |
| II-322 | Ph | BB | Me |
| II-323 | Ph | BC | Me |
| II-324 | Ph | BD | Me |
| II-325 | Ph | BE | Me |
| II-326 | Ph | BF | Me |
| II-327 | Ph | BG | Me |
| II-328 | Ph | BH | Me |
| II-329 | Ph | BI | Me |
| II-330 | Ph | BJ | Me |
| II-331 | Ph | BK | Me |
| II-332 | Ph | BL | Me |
| II-333 | Ph | BM | Me |
| II-334 | Ph | BN | Me |
| II-335 | Ph | BO | Me |
| II-336 | Ph | BP | Me |
| II-337 | Ph | BQ | Me |
| II-338 | Ph | BR | Me |
| II-339 | Ph | BS | Me |
| II-340 | Ph | BT | Me |
| II-341 | Ph | BU | Me |
| II-342 | Ph | BV | Me |
| II-343 | Ph | BW | Me |
| II-344 | Ph | BX | Me |
| II-345 | Ph | BY | Me |
| II-346 | Ph | BZ | Me |
| II-347 | Ph | CA | Me |
| II-348 | Ph | CB | Me |
| II-349 | Ph | CC | Me |
| II-350 | Ph | CD | Me |
| II-351 | Ph | CE | Me |
| II-352 | Ph | CF | Me |
| II-353 | Ph | CG | Me |
| II-354 | Ph | CH | Me |
| II-355 | Ph | CI | Me |
| II-356 | Ph | CJ | Me |
| II-357 | Ph | CK | Me |
| II-358 | Ph | CL | Me |
| II-359 | Ph | CM | Me |
| II-360 | Ph | CN | Me |

TABLE 17

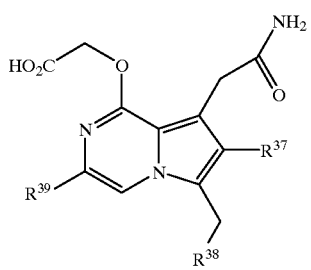

| Compound No. | R37 | R38 | R39 |
|---|---|---|---|
| II-361 | Me | BA | Et |
| II-362 | Me | BB | Et |
| II-363 | Me | BC | Et |
| II-364 | Me | BD | Et |
| II-365 | Me | BE | Et |
| II-366 | Me | BF | Et |
| II-367 | Me | BG | Et |
| II-368 | Me | BH | Et |
| II-369 | Me | BI | Et |
| II-370 | Me | BJ | Et |
| II-371 | Me | BK | Et |
| II-372 | Me | BL | Et |
| II-373 | Me | BM | Et |
| II-374 | Me | BN | Et |
| II-375 | Me | BO | Et |
| II-376 | Me | BP | Et |
| II-377 | Me | BQ | Et |
| II-378 | Me | BR | Et |
| II-379 | Me | BS | Et |
| II-380 | Me | BT | Et |
| II-381 | Me | BU | Et |
| II-382 | Me | BV | Et |
| II-383 | Me | BW | Et |
| II-384 | Me | BX | Et |
| II-385 | Me | BY | Et |
| II-386 | Me | BZ | Et |
| II-387 | Me | CA | Et |
| II-388 | Me | CB | Et |
| II-389 | Me | CC | Et |
| II-390 | Me | CD | Et |
| II-391 | Me | CE | Et |
| II-392 | Me | CF | Et |
| II-393 | Me | CG | Et |
| II-394 | Me | CH | Et |
| II-395 | Me | CI | Et |
| II-396 | Me | CJ | Et |
| II-397 | Me | CK | Et |
| II-398 | Me | CL | Et |
| II-399 | Me | CM | Et |
| II-400 | Me | CN | Et |
| II-401 | Et | BA | Et |
| II-402 | Et | BB | Et |
| II-403 | Et | BC | Et |
| II-404 | Et | BD | Et |
| II-405 | Et | BE | Et |
| II-406 | Et | BF | Et |
| II-407 | Et | BG | Et |
| II-408 | Et | BH | Et |
| II-409 | Et | BI | Et |
| II-410 | Et | BJ | Et |
| II-411 | Et | BK | Et |
| II-412 | Et | BL | Et |
| II-413 | Et | BM | Et |
| II-414 | Et | BN | Et |
| II-415 | Et | BO | Et |
| II-416 | Et | BP | Et |
| II-417 | Et | BQ | Et |
| II-418 | Et | BR | Et |
| II-419 | Et | BS | Et |
| II-420 | Et | BT | Et |
| II-421 | Et | BU | Et |
| II-422 | Et | BV | Et |

TABLE 17-continued

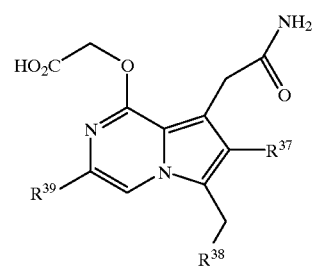

| Compound No. | R37 | R38 | R39 |
|---|---|---|---|
| II-423 | Et | BW | Et |
| II-424 | Et | BX | Et |
| II-425 | Et | BY | Et |
| II-426 | Et | BZ | Et |
| II-427 | Et | CA | Et |
| II-428 | Et | CB | Et |
| II-429 | Et | CC | Et |
| II-430 | Et | CD | Et |
| II-431 | Et | CE | Et |
| II-432 | Et | CF | Et |
| II-433 | Et | CG | Et |
| II-434 | Et | CH | Et |
| II-435 | Et | CI | Et |
| II-436 | Et | CJ | Et |
| II-437 | Et | CK | Et |
| II-438 | Et | CL | Et |
| II-439 | Et | CM | Et |
| II-440 | Et | CN | Et |
| II-441 | Ph | BA | Et |
| II-442 | Ph | BB | Et |
| II-443 | Ph | BC | Et |
| II-444 | Ph | BD | Et |
| II-445 | Ph | BE | Et |
| II-446 | Ph | BF | Et |
| II-447 | Ph | BG | Et |
| II-448 | Ph | BH | Et |
| II-449 | Ph | BI | Et |
| II-450 | Ph | BJ | Et |
| II-451 | Ph | BK | Et |
| II-452 | Ph | BL | Et |
| II-453 | Ph | BM | Et |
| II-454 | Ph | BN | Et |
| II-455 | Ph | BO | Et |
| II-456 | Ph | BP | Et |
| II-457 | Ph | BQ | Et |
| II-458 | Ph | BR | Et |
| II-459 | Ph | BS | Et |
| II-460 | Ph | BT | Et |
| II-461 | Ph | BU | Et |
| II-462 | Ph | BV | Et |
| II-463 | Ph | BW | Et |
| II-464 | Ph | BX | Et |
| II-465 | Ph | BY | Et |
| II-466 | Ph | BZ | Et |
| II-467 | Ph | CA | Et |
| II-468 | Ph | CB | Et |
| II-469 | Ph | CC | Et |
| II-470 | Ph | CD | Et |
| II-471 | Ph | CE | Et |
| II-472 | Ph | CF | Et |
| II-473 | Ph | CG | Et |
| II-474 | Ph | CH | Et |
| II-475 | Ph | CI | Et |
| II-476 | Ph | CJ | Et |
| II-477 | Ph | CK | Et |
| II-478 | Ph | CL | Et |
| II-479 | Ph | CM | Et |
| II-480 | Ph | CN | Et |

TABLE 18

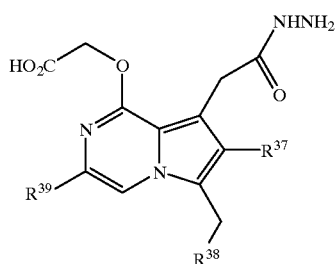

| Compound No. | R37 | R38 | R39 |
|---|---|---|---|
| II-481 | Me | BA | Me |
| II-482 | Me | BB | Me |
| II-483 | Me | BC | Me |
| II-484 | Me | BD | Me |
| II-485 | Me | BE | Me |
| II-486 | Me | BF | Me |
| II-487 | Me | BG | Me |
| II-488 | Me | BH | Me |
| II-489 | Me | BI | Me |
| II-490 | Me | BJ | Me |
| II-491 | Me | BK | Me |
| II-492 | Me | BL | Me |
| II-493 | Me | BM | Me |
| II-494 | Me | BN | Me |
| II-495 | Me | BO | Me |
| II-496 | Me | BP | Me |
| II-497 | Me | BQ | Me |
| II-498 | Me | BR | Me |
| II-499 | Me | BS | Me |
| II-490 | Me | BT | Me |
| II-501 | Me | BU | Me |
| II-502 | Me | BV | Me |
| II-503 | Ne | BW | Me |
| II-504 | Me | BX | Me |
| II-505 | Me | BY | Me |
| II-506 | Me | BZ | Me |
| II-507 | Me | CA | Me |
| II-508 | Me | CB | Me |
| II-509 | Me | CC | Me |
| II-510 | Me | CD | Me |
| II-511 | Me | CE | Me |
| II-512 | Me | CF | Me |
| II-513 | Me | CG | Me |
| II-514 | Me | CH | Me |
| II-515 | Me | CI | Me |
| II-516 | Me | CJ | Me |
| II-517 | Me | CK | Me |
| II-518 | Me | CL | Me |
| II-519 | Me | CM | Me |
| II-520 | Me | CN | Me |
| II-521 | Et | BA | Me |
| II-522 | Et | BB | Me |
| II-523 | Et | BC | Me |
| II-524 | Et | BD | Me |
| II-525 | Et | BE | Me |
| II-526 | Et | BF | Me |
| II-527 | Et | BG | Me |
| II-528 | Et | BH | Me |
| II-529 | Et | BI | Me |
| II-530 | Et | BJ | Me |
| II-531 | Et | BK | Me |
| II-532 | Et | BL | Me |
| II-533 | Et | BM | Me |
| II-534 | Et | BN | Me |
| II-535 | Et | BO | Me |
| II-536 | Et | BP | Me |
| II-537 | Et | BQ | Me |
| II-538 | Et | BR | Me |
| II-539 | Et | BS | Me |
| II-540 | Et | BT | Me |
| II-54J | Et | BU | Me |
| II-542 | Et | BV | Me |

TABLE 18-continued

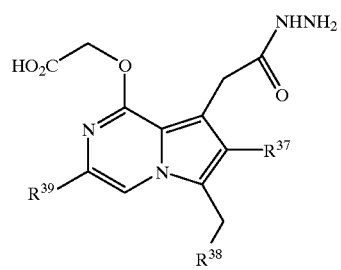

| Compound No. | R37 | R38 | R39 |
|---|---|---|---|
| II-543 | Et | BW | Me |
| II-544 | Et | BX | Me |
| II-545 | Et | BY | Me |
| II-546 | Et | BZ | Me |
| II-547 | Et | CA | Me |
| II-548 | Et | CB | Me |
| II-549 | Et | CC | Me |
| II-550 | Et | CD | Me |
| II-551 | Et | CE | Me |
| II-552 | Et | CF | Me |
| II-553 | Et | CG | Me |
| II-554 | Et | CH | Me |
| II-555 | Et | CI | Me |
| II-556 | Et | CJ | Me |
| II-557 | Et | CK | Me |
| II-558 | Et | CL | Me |
| II-559 | Et | CM | Me |
| II-560 | Et | CN | Me |
| II-561 | Ph | BA | Me |
| II-562 | Ph | BB | Me |
| II-563 | Ph | BC | Me |
| II-564 | Ph | BD | Me |
| II-565 | Ph | BE | Me |
| II-566 | Ph | BF | Me |
| II-567 | Ph | BG | Me |
| II-568 | Ph | BH | Me |
| II-569 | Ph | BI | Me |
| II-570 | Ph | BJ | Me |
| II-57J | Ph | BK | Me |
| II-572 | Ph | BL | Me |
| II-573 | Ph | BM | Me |
| II-574 | Ph | BN | Me |
| II-575 | Ph | BO | Me |
| II-576 | Ph | BP | Me |
| II-577 | Ph | BQ | Me |
| II-578 | Ph | BR | Me |
| II-579 | Ph | BS | Me |
| II-580 | Ph | BT | Me |
| II-581 | Ph | BU | Me |
| II-582 | Ph | BV | Me |
| II-583 | Ph | BW | Me |
| II-584 | Ph | BX | Me |
| II-585 | Ph | BY | Me |
| II-586 | Ph | BZ | Me |
| II-587 | Ph | CA | Me |
| II-588 | Ph | CB | Me |
| II-589 | Ph | CC | Me |
| II-590 | Ph | CD | Me |
| II-591 | Ph | CE | Me |
| II-592 | Ph | CF | Me |
| II-593 | Ph | CG | Me |
| II-594 | Ph | CH | Me |
| II-595 | Ph | CI | Me |
| II-596 | Ph | CJ | Me |
| II-597 | Ph | CK | Me |
| II-598 | Ph | CL | Me |
| II-599 | Ph | CM | Me |
| II-600 | Ph | CN | Me |

TABLE 19

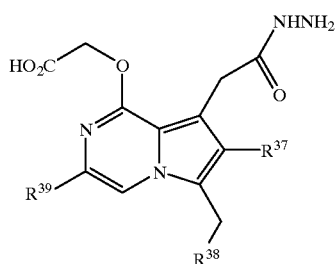

| Compound No. | $R^{37}$ | $R^{38}$ | $R^{39}$ |
|---|---|---|---|
| II-601 | Me | BA | Et |
| II-602 | Me | BB | Et |
| II-603 | Me | BC | Et |
| II-604 | Me | BD | Et |
| II-605 | Me | BE | Et |
| II-606 | Me | BF | Et |
| II-607 | Me | BG | Et |
| II-608 | Me | BH | Et |
| II-609 | Me | BI | Et |
| II-610 | Me | BJ | Et |
| II-611 | Me | BK | Et |
| II-612 | Me | BL | Et |
| II-613 | Me | BM | Et |
| II-614 | Me | BN | Et |
| II-615 | Me | BO | Et |
| II-616 | Me | BP | Et |
| II-617 | Me | BQ | Et |
| II-618 | Me | BR | Et |
| II-619 | Me | BS | Et |
| II-620 | Me | BT | Et |
| II-621 | Me | BU | Et |
| II-622 | Me | BV | Et |
| II-623 | Me | BW | Et |
| II-624 | Me | BX | Et |
| II-625 | Me | BY | Et |
| II-626 | Me | BZ | Et |
| II-627 | Me | CA | Et |
| II-628 | Me | CB | Et |
| II-629 | Me | CC | Et |
| II-630 | Me | CD | Et |
| II-631 | Me | CE | Et |
| II-632 | Me | CF | Et |
| II-633 | Me | CG | Et |
| II-634 | Me | CH | Et |
| II-635 | Me | CI | Et |
| II-636 | Me | CJ | Et |
| II-637 | Me | CK | Et |
| II-638 | Me | CL | Et |
| II-639 | Me | CM | Et |
| II-640 | Me | CN | Et |
| II-641 | Et | BA | Et |
| II-642 | Et | BB | Et |
| II-643 | Et | BC | Et |
| II-644 | Et | BD | Et |
| II-645 | Et | BE | Et |
| II-646 | Et | BF | Et |
| II-647 | Et | BG | Et |
| II-648 | Et | BH | Et |
| II-649 | Et | BI | Et |
| II-650 | Et | BJ | Et |
| II-651 | Et | BK | Et |
| II-652 | Et | BL | Et |
| II-653 | Et | BM | Et |
| II-654 | Et | BN | Et |
| II-655 | Et | BO | Et |
| II-656 | Et | BP | Et |
| II-657 | Et | BQ | Et |
| II-658 | Et | BR | Et |
| II-659 | Et | BS | Et |
| II-660 | Et | BT | Et |
| II-661 | Et | BU | Et |
| II-662 | Et | BV | Et |

TABLE 19-continued

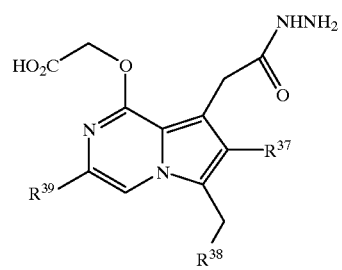

| Compound No. | $R^{37}$ | $R^{38}$ | $R^{39}$ |
|---|---|---|---|
| II-663 | Et | BW | Et |
| II-664 | Et | BX | Et |
| II-665 | Et | BY | Et |
| II-666 | Et | BZ | Et |
| II-667 | Et | CA | Et |
| II-668 | Et | CB | Et |
| II-669 | Et | CC | Et |
| II-670 | Et | CD | Et |
| II-671 | Et | CE | Et |
| II-672 | Et | CF | Et |
| II-673 | Et | CG | Et |
| II-674 | Et | CH | Et |
| II-675 | Et | CI | Et |
| II-676 | Et | CJ | Et |
| II-677 | Et | CK | Et |
| II-678 | Et | CL | Et |
| II-679 | Et | CM | Et |
| II-680 | Et | CN | Et |
| II-681 | Ph | BA | Et |
| II-682 | Ph | BB | Et |
| II-683 | Ph | BC | Et |
| II-684 | Ph | BD | Et |
| II-685 | Ph | BE | Et |
| II-686 | Ph | BF | Et |
| II-687 | Ph | BG | Et |
| II-688 | Ph | BH | Et |
| II-689 | Ph | BI | Et |
| II-690 | Ph | BJ | Et |
| II-691 | Ph | BK | Et |
| II-692 | Ph | BL | Et |
| II-693 | Ph | BM | Et |
| II-694 | Ph | BN | Et |
| II-695 | Ph | BO | Et |
| II-696 | Ph | BP | Et |
| II-697 | Ph | BQ | Et |
| II-698 | Ph | BR | Et |
| II-699 | Ph | BS | Et |
| II-700 | Ph | BT | Et |
| II-701 | Ph | BU | Et |
| II-702 | Ph | BV | Et |
| II-703 | Ph | BW | Et |
| II-704 | Ph | BX | Et |
| II-705 | Ph | BY | Et |
| II-706 | Ph | BZ | Et |
| II-707 | Ph | CA | Et |
| II-708 | Ph | CB | Et |
| II-709 | Ph | CC | Et |
| II-710 | Ph | CD | Et |
| II-711 | Ph | CE | Et |
| II-712 | Ph | CF | Et |
| II-713 | Ph | CG | Et |
| II-714 | Ph | CH | Et |
| II-715 | Ph | CI | Et |
| II-716 | Ph | CJ | Et |
| II-717 | Ph | CK | Et |
| II-718 | Ph | CL | Et |
| II-719 | Ph | CM | Et |
| II-720 | Ph | CN | Et |

TABLE 20

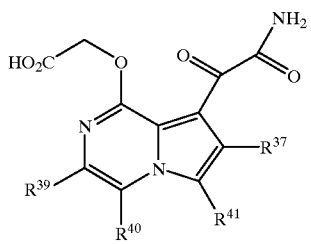

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-1 | Me | Me | AA | H | III-36 | Me | Et | AA | Et |
| III-2 | Me | Me | AB | H | III-37 | Me | Et | AB | Et |
| III-3 | Me | Me | AC | H | III-38 | Me | Et | AC | Et |
| III-4 | Me | Me | AD | H | III-39 | Me | Et | AD | Et |
| III-5 | Me | Me | AE | H | III-40 | Me | Et | AE | Et |
| III-6 | Me | Me | AF | H | III-41 | Me | Et | AF | Et |
| III-7 | Me | Me | AG | H | III-42 | Me | Et | AG | Et |
| III-8 | Me | Me | AA | Me | III-43 | Me | Ph | AA | H |
| III-9 | Me | Me | AB | Me | III-44 | Me | Ph | AB | H |
| III-10 | Me | Me | AC | Me | III-45 | Me | Ph | AC | H |
| III-11 | Me | Me | AD | Me | III-46 | Me | Ph | AD | H |
| III-12 | Me | Me | AE | Me | III-47 | Me | Ph | AE | H |
| III-13 | Me | Me | AF | Me | III-48 | Me | Ph | AF | H |
| III-14 | Me | Me | AG | Me | III-49 | Me | Ph | AG | H |
| III-15 | Me | Me | AA | Et | III-50 | Me | Ph | AA | Me |
| III-16 | Me | Me | AB | Et | III-51 | Me | Ph | AB | Me |
| III-17 | Me | Me | AC | Et | III-52 | Me | Pb | AC | Me |
| III-18 | Me | Me | AD | Et | III-53 | Me | Ph | AD | Me |
| III-19 | Me | Me | AE | Et | III-54 | Me | Ph | AE | Me |
| III-20 | Me | Me | AF | Et | III-55 | Me | Ph | AF | Me |
| III-21 | Me | Me | AG | Et | III-56 | Me | Ph | AG | Me |
| III-22 | Me | Et | AA | H | III-57 | Me | Ph | AA | Et |
| III-23 | Me | Et | AB | H | III-58 | Me | Ph | AB | Et |
| III-24 | Me | Et | AC | H | III-59 | Me | Ph | AC | Et |
| III-25 | Me | Et | AD | H | III-60 | Me | Ph | AD | Et |
| III-26 | Me | Et | AE | H | III-61 | Me | Ph | AE | Et |
| III-27 | Me | Et | AF | H | III-62 | Me | Ph | AF | Et |
| III-28 | Me | Et | AG | H | III-63 | Me | Ph | AG | Et |
| III-29 | Me | Et | AA | Me | | | | | |
| III-30 | Me | Et | AB | Me | | | | | |
| III-31 | Me | Et | AC | Me | | | | | |
| III-32 | Me | Et | AD | Me | | | | | |
| III-33 | Me | Et | AE | Me | | | | | |
| III-34 | Me | Et | AF | Me | | | | | |
| III-35 | Me | Et | AG | Me | | | | | |

TABLE 21

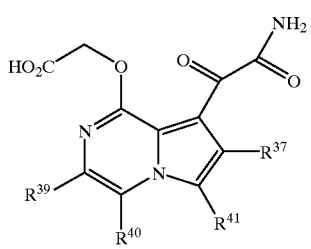

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-64 | Et | Me | AA | H | III-99 | Et | Et | AA | Et |
| III-65 | Et | Me | AB | H | III-100 | Et | Et | AB | Et |
| III-66 | Et | Me | AC | H | III-101 | Et | Et | AC | Et |
| III-67 | Et | Me | AD | H | III-102 | Et | Et | AD | Et |
| III-68 | Et | Me | AE | H | III-103 | Et | Et | AE | Et |
| III-69 | Et | Me | AF | H | III-104 | Et | Et | AF | Et |

TABLE 21-continued

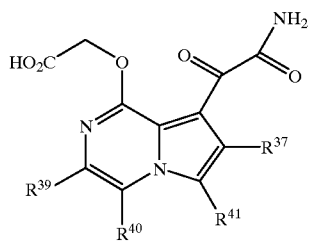

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-70 | Et | Me | AG | H | III-105 | Et | Et | AG | Et |
| III-71 | Et | Me | AA | Me | III-106 | Et | Ph | AA | H |
| III-72 | Et | Me | AB | Me | III-107 | Et | Ph | AB | H |
| III-73 | Et | Me | AC | Me | III-108 | Et | Ph | AC | H |
| III-74 | Et | Me | AD | Me | III-109 | Et | Ph | AD | H |
| III-75 | Et | Me | AE | Me | III-110 | Et | Ph | AE | H |
| III-76 | Et | Me | AF | Me | III-111 | Et | Ph | AF | H |
| III-77 | Et | Me | AG | Me | III-112 | Et | Ph | AG | H |
| III-78 | Et | Me | AA | Et | III-113 | Et | Ph | AA | Me |
| III-79 | Et | Me | AB | Et | III-114 | Et | Ph | AB | Me |
| III-80 | Et | Me | AC | Et | III-115 | Et | Ph | AC | Me |
| III-81 | Et | Me | AD | Et | III-116 | Et | Ph | AD | Me |
| III-82 | Et | Me | AE | Et | III-117 | Et | Ph | AE | Me |
| III-83 | Et | Me | AF | Et | III-118 | Et | Ph | AF | Me |
| III-84 | Et | Me | AG | Et | III-119 | Et | Ph | AG | Me |
| III-85 | Et | Et | AA | H | III-120 | Et | Ph | AA | Et |
| III-86 | Et | Et | AB | H | III-121 | Et | Ph | AB | Et |
| III-87 | Et | Et | AC | H | III-122 | Et | Ph | AC | Et |
| III-88 | Et | Et | AD | H | III-123 | Et | Ph | AD | Et |
| III-89 | Et | Et | AE | H | III-124 | Et | Ph | AE | Et |
| III-90 | Et | Et | AF | H | III-125 | Et | Ph | AF | Et |
| III-91 | Et | Et | AG | H | III-126 | Et | Ph | AG | Et |
| III-92 | Et | Et | AA | Me | | | | | |
| III-93 | Et | Et | AB | Me | | | | | |
| III-94 | Et | Et | AC | Me | | | | | |
| III-95 | Et | Et | AD | Me | | | | | |
| III-96 | Et | Et | AE | Me | | | | | |
| III-97 | Et | Et | AF | Me | | | | | |
| III-98 | Et | Et | AG | Me | | | | | |

TABLE 22

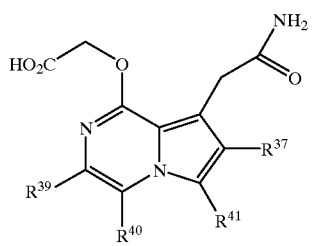

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-127 | Me | Me | AA | H | III-162 | Me | Et | AA | Et |
| III-128 | Me | Me | AB | H | III-163 | Me | Et | AB | Et |
| III-129 | Me | Me | AC | H | III-164 | Me | Et | AC | Et |
| III-130 | Me | Me | AD | H | III-165 | Me | Et | AD | Et |
| III-131 | Me | Me | AE | H | III-166 | Me | Et | AE | Et |
| III-132 | Me | Me | AF | H | III-167 | Me | Et | AF | Et |
| III-133 | Me | Me | AG | H | III-168 | Me | Et | AG | Et |
| III-134 | Me | Me | AA | Me | III-169 | Me | Ph | AA | H |
| III-135 | Me | Me | AB | Me | III-170 | Me | Ph | AB | H |
| III-136 | Me | Me | AC | Me | III-171 | Me | Ph | AC | H |
| III-137 | Me | Me | AD | Me | III-172 | Me | Ph | AD | H |
| III-138 | Me | Me | AE | Me | III-173 | Me | Ph | AE | H |

TABLE 22-continued

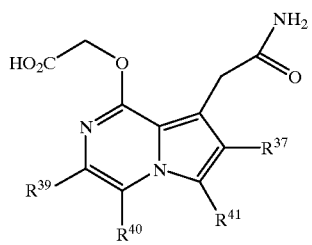

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-139 | Me | Me | AF | Me | III-174 | Me | Ph | AF | H |
| III-140 | Me | Me | AG | Me | III-175 | Me | Ph | AG | H |
| III-141 | Me | Me | AA | Et | III-176 | Me | Ph | AA | Me |
| III-142 | Me | Me | AB | Et | III-177 | Me | Ph | AB | Me |
| III-143 | Me | Me | AC | Et | III-178 | Me | Ph | AC | Me |
| III-144 | Me | Me | AD | Et | III-179 | Me | Ph | AD | Me |
| III-145 | Me | Me | AE | Et | III-180 | Me | Ph | AE | Me |
| III-146 | Me | Me | AF | Et | III-181 | Me | Ph | AF | Me |
| III-147 | Me | Me | AG | Et | III-182 | Me | Ph | AG | Me |
| III-148 | Me | Et | AA | H | III-183 | Me | Ph | AA | Et |
| III-149 | Me | Et | AB | H | III-184 | Me | Ph | AB | Et |
| III-150 | Me | Et | AC | H | III-185 | Me | Ph | AC | Et |
| III-151 | Me | Et | AD | H | III-186 | Me | Ph | AD | Et |
| III-152 | Me | Et | AE | H | III-187 | Me | Ph | AE | Et |
| III-153 | Me | Et | AF | H | III-188 | Me | Ph | AF | Et |
| III-154 | Me | Et | AG | H | III-189 | Me | Ph | AG | Et |
| III-155 | Me | Et | AA | Me | | | | | |
| III-156 | Me | Et | AB | Me | | | | | |
| III-157 | Me | Et | AC | Me | | | | | |
| III-158 | Me | Et | AD | Me | | | | | |
| III-159 | Me | Et | AE | Me | | | | | |
| III-160 | Me | Et | AF | Me | | | | | |
| III-161 | Me | Et | AG | Me | | | | | |

TABLE 23

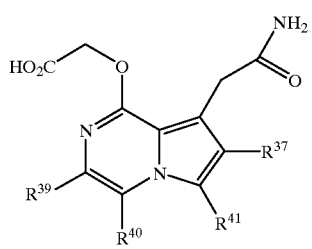

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-190 | Et | Me | AA | H | III-225 | Et | Et | AA | Et |
| III-191 | Et | Me | AB | H | III-226 | Et | Et | AB | Et |
| III-192 | Et | Me | AC | H | III-227 | Et | Et | AC | Et |
| III-193 | Et | Me | AD | H | III-228 | Et | Et | AD | Et |
| III-194 | Et | Me | AE | H | III-229 | Et | Et | AE | Et |
| III-195 | Et | Me | AF | H | III-230 | Et | Et | AF | Et |
| III-196 | Et | Me | AG | H | III-231 | Et | Et | AG | Et |
| III-197 | Et | Me | AA | Me | III-232 | Et | Ph | AA | H |
| III-198 | Et | Me | AB | Me | III-233 | Et | Ph | AB | H |
| III-199 | Et | Me | AC | Me | III-234 | Et | Ph | AC | H |
| III-200 | Et | Me | AD | Me | III-235 | Et | Ph | AD | H |
| III-201 | Et | Me | AE | Me | III-236 | Et | Ph | AE | H |
| III-202 | Et | Me | AF | Me | III-237 | Et | Ph | AF | H |
| III-203 | Et | Me | AG | Me | III-238 | Et | Ph | AG | H |
| III-204 | Et | Me | AA | Et | III-239 | Et | Ph | AA | Me |
| III-205 | Et | Me | AB | Et | III-240 | Et | Ph | AB | Me |
| III-206 | Et | Me | AC | Et | III-241 | Et | Ph | AC | Me |
| III-207 | Et | Me | AD | Et | III-242 | Et | Ph | AD | Me |
| III-208 | Et | Me | AE | Et | III-243 | Et | Ph | AE | Me |

TABLE 23-continued

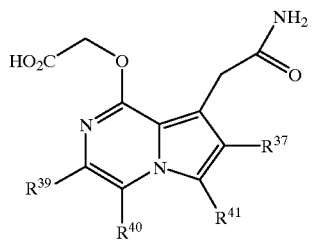

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-209 | Et | Me | AF | Et | III-244 | Et | Ph | AF | Me |
| III-210 | Et | Me | AG | Et | III-245 | Et | Ph | AG | Me |
| III-211 | Et | Et | AA | H | III-246 | Et | Ph | AA | Et |
| III-212 | Et | Et | AB | H | III-247 | Et | Ph | AB | Et |
| III-213 | Et | Et | AC | H | III-248 | Et | Ph | AC | Et |
| III-214 | Et | Et | AD | H | III-249 | Et | Ph | AD | Et |
| III-215 | Et | Et | AE | H | III-250 | Et | Ph | AE | Et |
| III-216 | Et | Et | AF | H | III-251 | Et | Ph | AF | Et |
| III-217 | Et | Et | AG | H | III-252 | Et | Ph | AG | Et |
| III-218 | Et | Et | AA | Me | | | | | |
| III-219 | Et | Et | AB | Me | | | | | |
| III-220 | Et | Et | AC | Me | | | | | |
| III-221 | Et | Et | AD | Me | | | | | |
| III-222 | Et | Et | AE | Me | | | | | |
| III-223 | Et | Et | AF | Me | | | | | |
| III-224 | Et | Et | AG | Me | | | | | |

TABLE 24

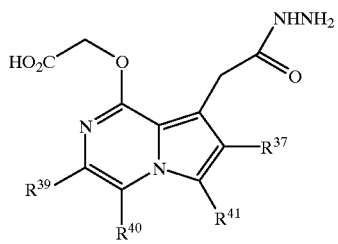

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-253 | Me | Me | AA | H | III-288 | Me | Et | AA | Et |
| III-254 | Me | Me | AB | H | III-289 | Me | Et | AB | Et |
| III-255 | Me | Me | AC | H | III-290 | Me | Et | AC | Et |
| III-256 | Me | Me | AD | H | III-291 | Me | Et | AD | Et |
| III-257 | Me | Me | AE | H | III-292 | Me | Et | AE | Et |
| III-258 | Me | Me | AF | H | III-293 | Me | Et | AF | Et |
| III-259 | Me | Me | AG | H | III-294 | Me | Et | AG | Et |
| III-260 | Me | Me | AA | Me | III-295 | Me | Ph | AA | H |
| III-261 | Me | Me | AB | Me | III-296 | Me | Ph | AB | H |
| III-262 | Me | Me | AC | Me | III-297 | Me | Ph | AC | H |
| III-263 | Me | Me | AD | Me | III-298 | Me | Ph | AD | H |
| III-264 | Me | Me | AE | Me | III-299 | Me | Ph | AE | H |
| III-265 | Me | Me | AF | Me | III-300 | Me | Ph | AF | H |
| III-266 | Me | Me | AG | Me | III-301 | Me | Ph | AG | H |
| III-267 | Me | Me | AA | Et | III-302 | Me | Ph | AA | Me |
| III-268 | Me | Me | AB | Et | III-303 | Me | Ph | AB | Me |
| III-269 | Me | Me | AC | Et | III-304 | Me | Ph | AC | Me |
| III-270 | Me | Me | AD | Et | III-305 | Me | Ph | AD | Me |
| III-271 | Me | Me | AE | Et | III-306 | Me | Ph | AE | Me |
| III-272 | Me | Me | AF | Et | III-307 | Me | Ph | AF | Me |
| III-273 | Me | Me | AG | Et | III-308 | Me | Ph | AG | Me |
| III-274 | Me | Et | AA | H | III-309 | Me | Ph | AA | Et |
| III-275 | Me | Et | AB | H | III-310 | Me | Ph | AB | Et |
| III-276 | Me | Et | AC | H | III-311 | Me | Ph | AC | Et |
| III-277 | Me | Et | AD | H | III-312 | Me | Ph | AD | Et |

TABLE 24-continued

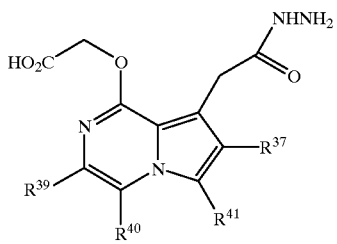

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-278 | Me | Et | AE | H | III-313 | Me | Ph | AE | Et |
| III-279 | Me | Et | AF | H | III-314 | Me | Ph | AF | Et |
| III-280 | Me | Et | AG | H | III-315 | Me | Ph | AG | Et |
| III-281 | Me | Et | AA | Me | | | | | |
| III-282 | Me | Et | AB | Me | | | | | |
| III-283 | Me | Et | AC | Me | | | | | |
| III-284 | Me | Et | AD | Me | | | | | |
| III-285 | Me | Et | AE | Me | | | | | |
| III-286 | Me | Et | AF | Me | | | | | |
| III-287 | Me | Et | AG | Me | | | | | |

TABLE 25

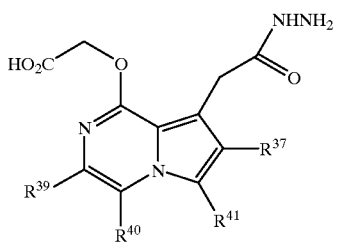

| Compound No. | $R^{37}$ | $R^{39}$ | $R^{40}$ | $R^{41}$ | Compound No. | $R^{37}$ | $R^{39}$ | $R^{40}$ | $R^{41}$ |
|---|---|---|---|---|---|---|---|---|---|
| III-316 | Et | Me | AA | H | III-351 | Et | Et | AA | Et |
| III-317 | Et | Me | AB | H | III-352 | Et | Et | AB | Et |
| III-318 | Et | Me | AC | H | III-353 | Et | Et | AC | Et |
| III-319 | Et | Me | AD | H | III-354 | Et | Et | AD | Et |
| III-320 | Et | Me | AE | H | III-355 | Et | Et | AE | Et |
| III-321 | Et | Me | AF | H | III-356 | Et | Et | AF | Et |
| III-322 | Et | Me | AG | H | III-357 | Et | Et | AG | Et |
| III-323 | Et | Me | AA | Me | III-358 | Et | Ph | AA | H |
| III-324 | Et | Me | AB | Me | III-359 | Et | Ph | AB | H |
| III-325 | Et | Me | AC | Me | III-360 | Et | Ph | AC | H |
| III-326 | Et | Me | AD | Me | III-361 | Et | Ph | AD | H |
| III-327 | Et | Me | AE | Me | III-362 | Et | Ph | AE | H |
| III-328 | Et | Me | AF | Me | III-363 | Et | Ph | AF | H |
| III-329 | Et | Me | AG | Me | III-364 | Et | Ph | AG | H |
| III-330 | Et | Me | AA | Et | III-365 | Et | Ph | AA | Me |
| III-331 | Et | Me | AB | Et | III-366 | Et | Ph | AB | Me |
| III-332 | Et | Me | AC | Et | III-367 | Et | Ph | AC | Me |
| III-333 | Et | Me | AD | Et | III-368 | Et | Ph | AD | Me |
| III-334 | Et | Me | AE | Et | III-369 | Et | Ph | AE | Me |
| III-335 | Et | Me | AF | Et | III-370 | Et | Ph | AF | Me |
| III-336 | Et | Me | AG | Et | III-371 | Et | Ph | AG | Me |
| III-337 | Et | Et | AA | H | III-372 | Et | Ph | AA | Et |
| III-338 | Et | Et | AB | H | III-373 | Et | Ph | AB | Et |
| III-339 | Et | Et | AC | H | III-374 | Et | Ph | AC | Et |
| III-340 | Et | Et | AD | H | III-375 | Et | Ph | AD | Et |
| III-341 | Et | Et | AE | H | III-376 | Et | Ph | AE | Et |
| III-342 | Et | Et | AF | H | III-377 | Et | Ph | AF | Et |
| III-343 | Et | Et | AG | H | III-378 | Et | Ph | AG | Et |
| III-344 | Et | Et | AA | Me | | | | | |
| III-345 | Et | Et | AB | Me | | | | | |
| III-346 | Et | Et | AC | Me | | | | | |

TABLE 25-continued

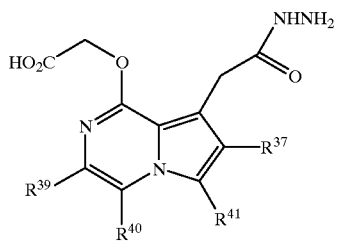

| Compound No. | R³⁷ | R³⁹ | R⁴⁰ | R⁴¹ | Compound No. | R³⁷ | R³⁹ | R⁴⁰ | R⁴¹ |
|---|---|---|---|---|---|---|---|---|---|
| III-347 | Et | Et | AD | Me | | | | | |
| III-348 | Et | Et | AE | Me | | | | | |
| III-349 | Et | Et | AF | Me | | | | | |
| III-350 | Et | Et | AG | Me | | | | | |

Test Example: Inhibition Test of Human Secretory Phospholipase $A_2$

Analytical Experiment

In order to identify and evaluate an inhibitor of recombinant human secretory phospholipase $A_2$, the following chromogenic assay is utilized. The assay herein has been applied for high volume screening wherein 96 well microtiterplate is used. A general explanation for such assay is described in "Analysis of Human Synovial Fluid Phospholipase $A_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis: the disclosure of which is incorporated herein for reference.

Reagents:
Reaction Buffer-

| | |
|---|---|
| $CaCl_2 \cdot 6H_2O$ | (2.19 g/L) |
| KCl | (7.455 g/L) |
| Bovine Serum Albumin (fatty acid free) | (1 g/L) (Sigma A-7030) |
| Tris-HCl | (3.94 g/L) | pH 7.5 (adjusted with NaOH)
Enzyme Buffer-
  0.05 M-AcONa
  0.2 M-NaCl
pH 4.5 (adjusted with acetic acid)
Enzyme Solution-
  1 mg of $sPLA_2$ is dissolved in 1 ml of an enzyme buffer. Thereafter, the solution is maintained at 4° C.
In the assay, 5 μl of the solution is diluted with 1995 μl of the reaction buffer to be used.
DTNB-
  198 mg of 5,5'-dithiobis-2-benzoic acid (manufactured by Wako Pure Chemicals) is dissolved in 100 ml of $H_2O$
H 7.5 (adjusted with NaOH)
Substrate Solution-
  100 mg of racemic 1,2-bis(heptanoylthio)-1,2-dideoxy-sn-glycero-3-phospholylcholine is dissolved in 1 ml of chloroform.
Triton-X 100-
  624.9 mg of Triton-X 100 is dissolved in the reaction buffer.

Enzyme Reaction: for 1 Plate of Microtiterplate 1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml of the reaction buffer and 0.46 ml of DTNB, and 0.18 ml each of the admixture is poured to wells of the 96 well microtiterplate.
2) 10 μl of a test compound (or solvent blank) are added in accordance with alignment of plates which has been previously set.
3) Incubation is effected at 40° C. for 15 minutes.
4) 20μl of an enzyme solution ($sPLA_2$) which has been previously diluted (50 ng/well) are added to start reaction (40° C., 30 minutes).
5) Changes in absorbancy for 30 minutes are measured by a plate reader, and inhibition activity was calculated (OD: 405 nm).
6) $IC_{50}$ was determined by plotting log concentration with respect to inhibition values within 10% to 90% inhibiting range.

Results of the human secretory phospholipase $A_2$ inhibition test are shown in the following Table 26.

TABLE 26

| Compound NO. | $IC_{50}$ (μM) |
|---|---|
| I-1 | 0.208 |
| I-2 | 0.011 |
| I-3 | 2.623 |
| I-4 | 0.035 |
| I-5 | 0.314 |
| I-6 | 0.009 |
| I-7 | 0.389 |
| I-8 | 0.011 |
| I-9 | 0.435 |
| I-10 | 0.014 |
| I-11 | 0.194 |
| I-12 | 0.010 |
| I-13 | 0.157 |
| I-14 | 0.011 |
| I-15 | 0.512 |
| I-16 | 0.006 |
| I-17 | 0.172 |
| I-18 | 0.009 |
| I-19 | 0.562 |
| I-20 | 0.021 |
| I-21 | 0.041 |
| I-22 | 0.008 |

TABLE 26-continued

| Compound NO. | IC$_{50}$ ($\mu$M) |
|---|---|
| I-23 | 0.651 |
| I-24 | 0.017 |
| I-25 | 0.196 |
| I-26 | 0.012 |
| I-27 | 0.022 |
| I-28 | 0.007 |
| I-29 | 0.056 |
| I-30 | 0.008 |
| I-31 | 1.168 |
| I-32 | 0.028 |
| I-33 | 0.703 |
| I-34 | 0.026 |
| I-35 | 0.182 |
| I-36 | 0.011 |
| I-37 | 0.726 |
| I-38 | 0.033 |
| I-39 | 0.151 |
| I-40 | 0.012 |
| I-41 | 0.107 |
| I-42 | 0.010 |
| I-43 | 0.041 |
| I-44 | 0.007 |
| I-45 | 0.117 |
| I-46 | 0.010 |
| I-47 | 0.389 |
| I-48 | 0.015 |
| I-49 | 0.211 |
| I-50 | 0.017 |
| I-51 | 0.061 |
| I-52 | 0.005 |
| I-53 | 0.059 |
| I-54 | 0.006 |
| I-55 | 0.032 |
| I-56 | 0.006 |
| I-58 | 0.025 |
| I-59 | 15.8 |
| I-60 | 1.21 |
| I-61 | 0.081 |
| I-62 | 0.006 |
| I-63 | 0.057 |
| I-64 | 0.006 |
| I-65 | 1.55 |
| I-66 | 0.045 |
| I-67 | 0.057 |
| I-68 | 0.008 |
| I-69 | 0.033 |
| I-70 | 0.005 |
| I-71 | 0.901 |
| I-72 | 0.013 |
| I-73 | 0.129 |
| I-74 | 0.006 |
| I-75 | 1.46 |
| I-76 | 0.029 |
| I-77 | 1.38 |
| I-78 | 0.060 |
| I-79 | 0.062 |
| I-80 | 0.006 |
| I-81 | 0.201 |
| I-82 | 0.005 |
| I-83 | 0.116 |
| I-84 | 0.008 |
| I-85 | 0.370 |
| I-86 | 0.011 |
| I-87 | 0.129 |
| I-88 | 0.008 |
| I-89 | 0.315 |
| I-90 | 0.038 |
| I-91 | 0.048 |
| I-92 | 0.076 |
| I-93 | 0.282 |
| I-94 | 0.650 |
| I-95 | 0.175 |
| I-96 | 0.077 |
| I-97 | 0.078 |
| I-98 | 0.102 |
| I-99 | 0.021 |
| I-100 | 0.021 |

TABLE 26-continued

| Compound NO. | IC$_{50}$ ($\mu$M) |
|---|---|
| I-101 | 0.019 |
| I-102 | 0.020 |
| I-103 | 0.540 |
| I-104 | 0.988 |
| I-105 | 0.400 |
| I-106 | 0.819 |

Formulation Example

It is to be noted that the following Formulation Examples 1 to 8 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| | |
|---|---:|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---:|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| | |
|---|---:|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| | |
|---|---:|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---:|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---:|
| Active ingredient | 127 mg |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

INDUSTRIAL APPLICABILITY

The compounds according to the present invention have sPLA$_2$ inhibiting activity, so that the compounds of the invention inhibits sPLA$_2$-mediated fatty acid (such as arachidonic acid) release, whereby it is effective for treating septic shock and the like.

What is claimed is:

1. A compound represented by the formula (I):

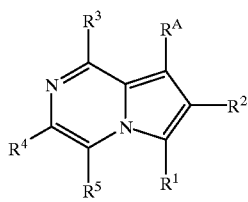
(I)

wherein $R^1$ is hydrogen atom or a group selected from (a) C6 to C20 alkyl, C6 to C20 alkenyl, C6 to C20 alkynyl, carbocyclic groups, and heterocyclic groups, (b) the groups represented by (a) each substituted independently with at least one group selected from non-interfering substituents, and (c) -($L^1$)-$R^6$ wherein $L^1$ is a divalent linking group of 1 to 18 atom(s) selected from hydrogen atom(s), nitrogen atom(s), carbon atom(s), oxygen atom(s), and sulfur atom (s), and $R^6$ is a group selected from the groups (a) and (b);

$R^2$ is hydrogen atom, or a group containing 1 to 4 non-hydrogen atoms;

$R^3$ is -($L^2$)-(acidic group) wherein $L^2$ is an acid linker having an acid linker length of 1 to 5;

$R^4$ and $R^5$ are selected independently from hydrogen atom, non-interfering substituents, carbocyclic groups, carbocyclic groups substituted with a non-interfering substituent(s), heterocyclic groups, and heterocyclic groups substituted by a non-interfering substituent(s); and $R^A$ is a group represented by the formula:

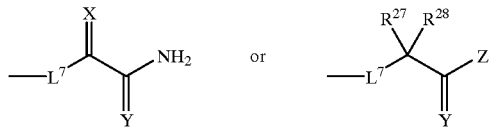

wherein $L^7$ is a divalent linker group selected from a bond or a divalent group selected from —$CH_2$—, —O—, —S—, —NH—, or —CO—, $R^{27}$ and $R^{28}$ are independently hydrogen atom, C1 to C3 alkyl or a halogen; X and Y are independently an oxygen atom or a sulfur atom; and Z is —$NH_2$ or —$NHNH_2$; a prodrug thereof, or its pharmaceutically acceptable salt, or its solvate.

2. A compound represented by the formula (II):

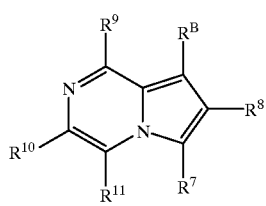
(II)

wherein $R^7$ is hydrogen atom or —($CH_2$)m—$R^{12}$ wherein m is an integer from 1 to 6, and $R^{12}$ is (d) a group represented by the formula:

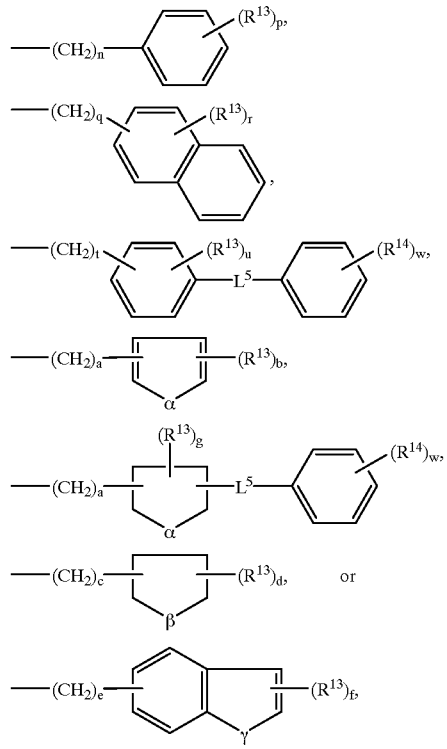

wherein a, c, e, n, q, and t are independently an integer from 0 to 2, $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl, α is an oxygen atom or a sulfur atom, $L^5$ is —($CH_2$)v—, —C=C—, —C≡C—, —O—, or —S—, v is an integer from 0 to 2, β is —$CH_2$— or —($CH_2$)$_2$—, γ is an oxygen atom or a sulfur atom, b is an integer from 0 to 3, d is an integer from 0 to 4, f, p, and w are independently an integer from 0 to 5, g is an integer from 0 to 2, r is an integer from 0 to 7, and u is an integer from 0 to 4, or is (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen;

$R^8$ is C1 to C3 alkyl, C1 to C3 alkenyl, C3 to C4 cycloalkyl, C3 to C4 cycloalkenyl, C1 to C2 haloalkyl, C1 to C3 alkyloxy, or C1 to C3 alkylthio;

$R^9$ is —($L^3$)—$R^{15}$ wherein $L^3$ is represented by the formula:

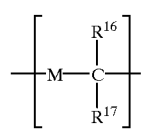

wherein M is —$CH_2$—, —O—, —N($R^{24}$)—, or —S—, $R^{16}$ and $R^{17}$ are independently hydrogen atom, C1 to C10 alkyl, aryl, aralkyl, alkyloxy, haloalkyl, carboxy, or a halogen, and $R^{24}$ is hydrogen atom or C1 to C6 alkyl, and $R^{15}$ is represented by the formula:

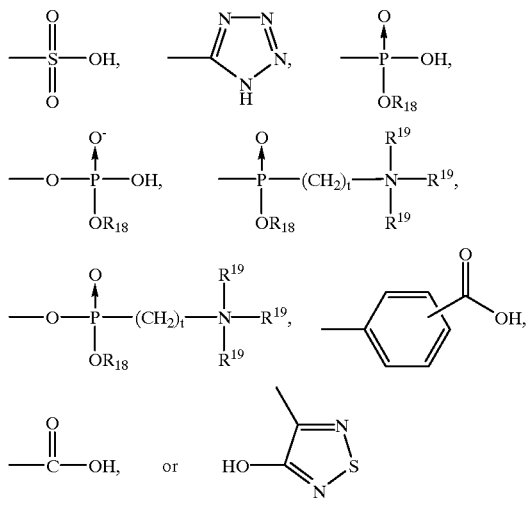

wherein $R^{18}$ is hydrogen atom, a metal, or C1 to C10 alkyl, R19 is independently hydrogen atom, or C1 to C10 alkyl, and t is an integer from 1 to 8;

$R^{10}$ and $R^{11}$ are independently hydrogen atom or a non-interfering substituent selected from hydrogen, C1 to C8 alkyl, C2 to C8 alkenyl, C2 to C8 alkynyl, C7 to C12 aralkyl, C7 to C12 alkaryl, C3 to C8 cycloalkyl, C3 to C8 cycloalkenyl, phenyl, tolyl, xylyl, biphenyl, C1 to C8 alkyloxy, C2 to C8 alkenyloxy, C2 to C8 alkynyloxy, C2 to C12 alkyloxyalkyl, C2 to C12 alkyloxyalkyloxy, C2 to C12 alkylcarbonyl, C2 to C12 alkylcarbonylamino, C2 to C12 alkyloxyamino, C2 to C 12 alkyloxyaminocarbonyl, C1 to C12 alkylamino, C1 to C6 alkylthio, C2 to C12 alkylthiocarbonyl, C1 to C8 alkylsulfinyl, C1 to C8 alkylsulfonyl, C2 to C8 haloalkyloxy, C1 to C8 haloalkylsulfonyl, C2 to C8 haloalkyl, C1 to C8 hydroxyalkyl, —C(O)O(C1 to C8 alkyl), —(CH$_2$)$_z$—O—(C1 to C8 alkyl), benzyloxy, aryloxy, arylthio, —(CONHSO$_2$R$^{25}$), —CHO, amino, amidino, halogen, carbamyl, carboxyl, carbalkoxy, —(CH$_2$)$_z$—CO$_2$H, cyano, cyanoguanidinyl, guanidino, hydrazide, hydrazino, hydrazido, hydroxy, hydroxyamino, iodo, nitro, phosphono, —SO$_3$H, thioacetal, thiocarbonyl, or carbonyl, $R^{25}$ is C1 to C6 alkyl or aryl, z is an integer from 1 to 8; and $R^B$ is a group represented by the formula:

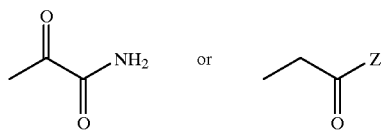

wherein Z is the same as defined above a prodrug thereof, or its pharmaceutically acceptable salt, or its solvate.

3. A compound, a prodrug thereof, or its pharmaceutically acceptable salt, or its solvate as claimed in claim 1, wherein said $R^1$ is represented by the formula:

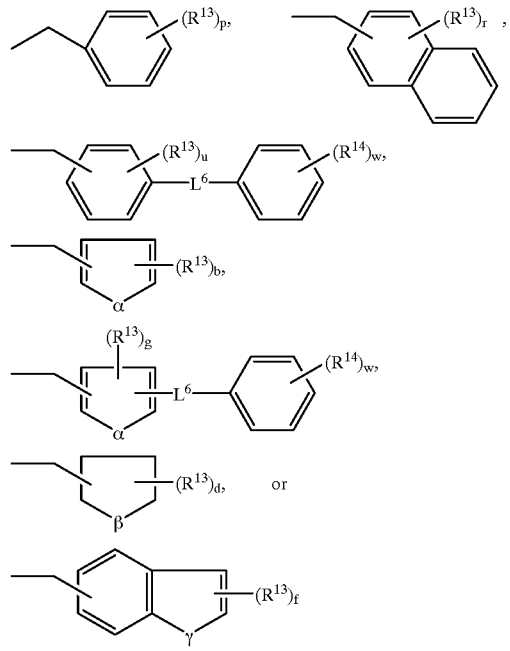

wherein $R^{13}$, $R^{14}$, b, d, f, g, p, r, u, w, α, β, and γ are the same as defined above, $L^6$ is a bond, —CH$_2$—, —C=C—, —C≡C—, —O—, or —S—.

4. A compound, a prodrug thereof, or its pharmaceutically acceptable salt, or its solvate as claimed in claim 1, wherein $R^2$ is C1 to C3 alkyl or C3 to C4 cycloalkyl.

5. A compound, a prodrug thereof, or its pharmaceutically acceptable salt, or its solvate as claimed in claim 1, wherein $L^2$ is —O—CH$_2$—.

6. A compound represented by the formula (III):

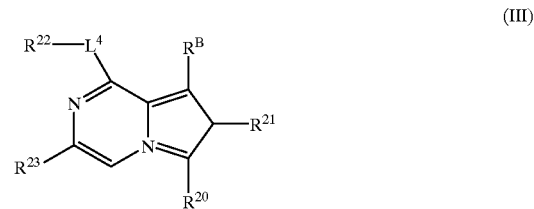

(III)

wherein $R^{20}$ is a group represented by the formula:

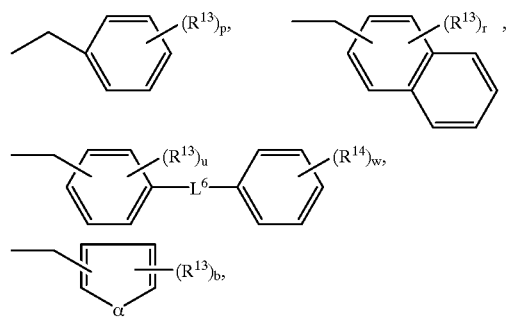

-continued

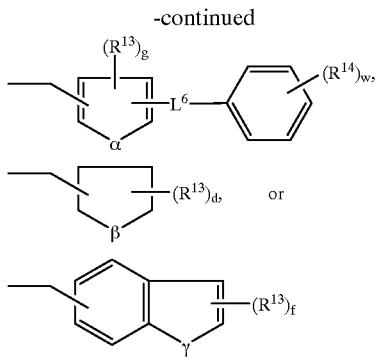

wherein $L^6$, $R^{13}$, $R^{14}$, b, d, f, g, p, r, u, w, α, β, and γ are the same as defined above, $R^{21}$ is C1 to C3 alkyl or C3 to C4 cycloalkyl;
$L^4$ is —O—$CH_2$—, —S—$CH_2$—, —N($R^{24}$)—$CH_2$—, —$CH_2$—$CH_2$—, —O—CH($CH_3$)—, or —O—CH(($CH_2$)$_2$Ph)—
wherein $R^{24}$ is hydrogen atom or C1 to C6 alkyl and Ph is phenyl;
$R^{22}$ is —COOH, —$SO_3$H, or P(O)(OH)$_2$;
$R^{23}$ is hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, arylthio, a carbocyclic group, or a heterocyclic group; and $R^B$ is the same as defined above; a prodrug thereof, or its pharmaceutically acceptable salt, or its solvate.

7. A compound represented by the formula (IV):

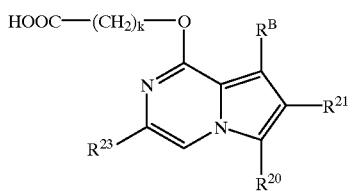

wherein $R^{20}$, $R^{21}$, $R^{23}$, and $R^B$ are the same as defined above; and k is an integer from 1 to 3; a prodrug thereof, or its pharmaceutically acceptable salt, or its solvate.

8. A compound, a prodrug thereof, or its pharmaceutically acceptable salt, or its solvate as claimed in claim 6, wherein $L^4$ is —O—$CH_2$—.

9. A compound, a prodrug thereof, or its pharmaceutically acceptable salt, or its solvate as claimed in claim 1, wherein said $R^A$ and $R^B$ are -COCONH$_2$.

10. A compound, a prodrug thereof, or its pharmaceutically acceptable salt, or its solvate as claimed in claim 1, wherein $R^A$ and $R^B$ are —$CH_2CONH_2$.

11. A compound, a prodrug thereof, or its pharmaceutically acceptable salt, or its solvate as claimed in claim 1, wherein $R^A$ and $R^B$ are —$CH_2$CONHNH$_2$.

12. The prodrug as claimed in claim 1 which is in the form of an ester.

13. A pyrrolo[1,2-a]pyrazine compound selected from the group consisting of:
[6-Benzyl-7-ethyl-8-oxamoylpyrrolo[1,2-a]pyrazin-1-yl] oxyacetic acid,
[6-Cyclohexylmethyl-7-ethyl-8-oxamoylpyrrolo[1,2-a] pyrazin-1-yl]oxyacetic acid,
[7-Ethyl-6-(3-methoxybenzyl)-8-oxamoylpyrrolo[1,2-a] pyrazin-1-yl]oxyacetic acid,
[6-(Benzo[b]thiophen-6-ylmethyl)-7-ethyl-8-oxamoylpyrrolo[1,2-a]pyrazin-1-yl]oxyacetic acid,
[6-Benzyl-7-ethyl-3-methyl-8-oxamoylpyrrolo[1,2-a]pyrazin-1-yl]oxyacetic acid,
[7-Ethyl-6-(4-fluorobenzyl)-3-methyl-8-oxamoylpyrrolo[1,2-a]pyrazin-1-yl]oxyacetic acid,
[6-( 2-Biphenylmethyl)-7-ethyl-3-methyl-8-oxamoylpyrrolo[1,2-a]pyrazin-1-yl]oxyacetic acid,
[6-Cyclopentylmethyl-7-ethyl-3-methyl-8-oxamoylpyrrolo[1,2-a]pyrazin-1-yl]oxyacetic acid,
[6-( 2-Benzyl)benzyl-7-ethyl-3-methyl-8-oxamoylpyrrolo[1,2-a]pyrazin-1-yl]oxyacetic acid,
[7-Ethyl-6-(2-(4-fluorophenyl)benzyl)-3-methyl-8-oxamoylpyrrolo[1,2-a]pyrazin-1-yl]oxyacetic acid,
[7-Ethyl-6-(3-fluorobenzyl)-3-methyl-8-oxamoylpyrrolo[1,2-a]pyrazin-1-yl]oxyacetic acid,
[6-Benzyl-7-ethyl-3-isopropyl-8-oxamoylpyrrolo[1,2-a]pyrazin-1-yl]oxyacetic acid,
[6-Benzyl-3,7-diethyl-8-oxamoylpyrrolo[1,2-a]pyrazin-1-yl]oxyacetic acid,
[6-Benzyl-7-ethyl-8-oxamoyl-3-phenylpyrrolo[1,2-a]pyrazin-1-yl]oxyacetic acid,
[6-Benzyl-7-ethyl-3-isobutyl-8-oxamoylpyrrolo[1,2-a]pyrazin-1-yl]oxyacetic acid,
[3,6-Dibenzyl-7-ethyl-8-oxamoylpyrrolo[1,2-a]pyrazin-1-yl]oxyacetic acid,
[7-Ethyl-3-methyl-8-oxamoyl-6-(2-(2-thienyl)benzyl)pyrrolo[1,2-a]pyrazin-1-yl]oxyacetic acid,
[7-Ethyl-3-methyl-8-oxamoyl-6-(2-phenylethynylbenzyl)pyrrolo[1,2-a]pyrazin-1-yl]oxyacetic acid,
[7-Ethyl-3-methyl-8-oxamoyl-6-( 2-phenyloxybenzyl)pyrrolo[1,2-a]pyrazin-1-yl]oxyacetic acid,
[7-Ethyl-3-methyl-8-oxamoyl-6-(2-(3-thienyl) benzyl)pyrrolo[1,2-a]pyrazin-1-yl]oxyacetic acid,
[7-Ethyl-3-methyl-6-(2-(5-methylthien-2-yl)benzyl)-8-oxamoylpyrrolo[1,2-a]pyrazin-1-yl]oxyacetic acid,
[7-Ethyl-6-(2-(4-methoxyphenyl)benzyl)-3-methyl-8-oxamoylpyrrolo[1,2-a]pyrazin-1-yl]oxyacetic acid,
[7-Ethyl-3-methyl-6-(2-(4-methylphenyl)benzyl)-8-oxamoylpyrrolo[1,2-a]pyrazin-1-yl]oxyacetic acid,
[7-Ethyl-3-methyl-8-oxamoyl-6-(2-(2-phenylethyl) benzyl)pyrrolo[1,2-a[pyrazin-1-yl]oxyacetic acid,
[6-Benzyl-7-cyclopropyl-3-methyl-8-oxamoylpyrrolo[1,2-a]pyrazin-1-yl]oxyacetic acid,
[7-Cyclopropyl-6-(4-fluorobenzyl)-3-methyl-8-oxamoylpyrrolo[1,2-a]pyrazin-1-yl]oxyacetic acid,
[6-Benzyl-3-cyclohexyl-7-ethyl-8-oxamoylpyrrolo[1,2-a]pyrazin-1-yl]oxyacetic acid,
[6-(2-Biphenylmethyl)-3-cyclohexyl-7-ethyl-8-oxamoylpyrrolo[1,2-a]pyrazin-1-yl]oxyacetic acid,
[6-Benzyl-3,7-dimethyl-8-oxamoylpyrrolo[1,2-a]pyrazin-1-yl]oxyacetic acid,
[7-Ethyl-3-methyl-6-(5-methylthien-2-ylmethyl)-8-oxamoylpyrrolo[1,2-a]pyrazin-1-yl]oxyacetic acid,
[6-(Benzo[b]thiophen-3-ylmethyl)-7-ethyl-3-methyl-8-oxamoylpyrrolo[1,2-a]pyrazin-1-yl]oxyacetic acid,
Sodium [7-ethyl-6-(4-fluorobenzyl)-3-methyl-8-oxamoylpyrrolo[1,2-a]pyrazin-1-yl]oxyacetate,
Sodium [7-ethyl-6-(2-(4-fluorophenyl)benzyl)-3-methyl-8-oxamoylpyrrolo[1,2-a]pyrazin-1-yl]oxyacetate,
Sodium [7-ethyl-3-methyl-8-oxamoyl-6-(2-(2-thienyl) benzyl) pyrrolo[1,2-a]pyrazin-1-yl]oxyacetate,
Sodium [7-ethyl-3-methyl-8-oxamoyl-6-(2-(3-thienyl) benzyl)pyrrolo[1,2-a]pyrazin-1-yl]oxyacetate, and a prodrug thereof, or its pharmaceutically acceptable salt, or its solvate.

14. A pyrrolo[1,2-a] pyrazine compound selected from the group consisting of

Methyl [7-ethyl-6-(2-(4-fluorophenyl)benzyl)-3-methyl-8-oxamoylpyrrolo [1,2-a]pyrazin-1 -yl]oxyacetate, Ethyl [7-ethyl-6-(2-(4-fluorophenyl)benzyl)-3-methyl-8-oxamoylpyrrolo [1,2-a]pyrazin-1-yl]oxyacetate, Morpholinylethyl [7-ethyl-6-(2-(4-fluorophenyl)benzyl)-3-methyl-8-oxamoylpyrrolo[1,2-a]pyrazin-1-yl]oxyacetate, Sodium [7-ethyl-6-(2-(4-fluorophenyl)benzyl)-3-methyl-8-oxamoylpyrrolo[1,2-a]pyrazin-1 -yl]oxyacetate, Methyl [7-ethyl-3-methyl-8-oxamoyl-6-(2-(2-thienyl)benzyl)pyrrolo[1,2-a]pyrazin-1-yl]oxyacetate, Ethyl [7-ethyl-3-methyl-8-oxamoyl-6-(2-(2-thienyl)benzyl) pyrrolo[1,2-a]pyrazin-1-yl]oxyacetate, Morpholinylethyl [7-ethyl-3-methyl-8-oxamoyl-6-(2-(2-thienyl)benzyl)pyrrolo (1,2-a]pyrazin-1-yl]oxyacetate, and Sodium [7-ethyl-3-methyl-8-oxamoyl-6-(2-(2-thienyl)benzyl)pyrrolo[1,2-a]pyrazin-1-yl]oxyacetate.

15. A pharmaceutical composition containing a compound as claimed in claim 1 as an active ingredient.

16. A pharmaceutical composition as claimed in claim 15, wherein said composition is for inhibiting sPLA$_2$.

17. A pharmaceutical composition as claimed in claim 15, wherein said composition is for treatment or prevention of Inflammatory Diseases.

18. A method of inhibiting sPLA$_2$ mediated release of fatty acid which comprises contacting sPLA$_2$ with a therapeutically effective amount of a pyrrolo[1,2-a]pyrazine compound as claimed in claim 1.

19. A method of treating a mammal to alleviate the pathological effects of Inflammatory Diseases; wherein the method comprises administration to said mammal of a pyrrolo[1,2-a]pyrazine compound as claimed in claim 1 in a pharmaceutically effective amount.

20. A compound of claim 1 or a pharmaceutical formulation containing an effective amount of a pyrrolo[1,2-a] pyrazine compound of claim 1 for use in treatment of Inflammatory Diseases.

21. A compound of claim 1 or a pharmaceutical formulation containing an effective amount of a pyrrolo[1,2-a] pyrazine compound of claim 1 for use as an inhibitor for inhibiting sPLA$_2$ mediated release of fatty acid.

22. A compound, a prodrug thereof, or its pharmaceutically acceptable salt or its solvate as claimed in claim 2, wherein said R$^7$ is represented by the formula:

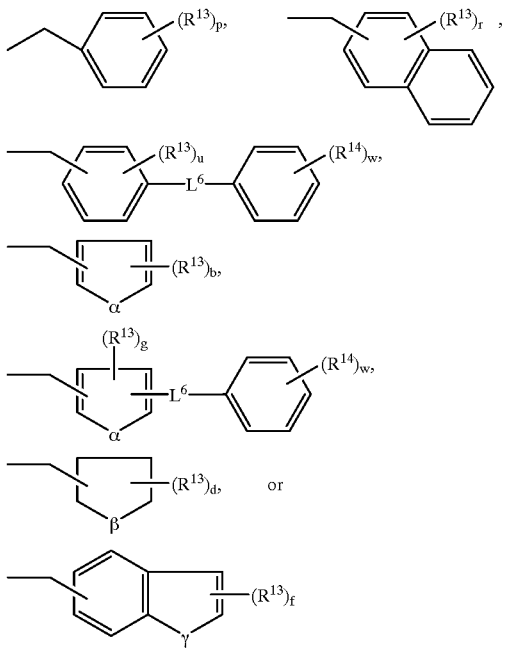

wherein R$^{13}$, R$^{14}$, b, d, f, g, p, r, u, w, α, β, and γ are the same as defined in claim 2, L$^6$ is a bond, —CH$_2$—, —C=C—, —C≡C—, —O—, or —S—.

23. A compound, a prodrug thereof, or its pharmaceutically acceptable salt, or its solvate as claimed in claim 2, wherein R$^8$ is C1 to C3 alkyl or C3 to C4 cycloalkyl.

24. A compound, a prodrug thereof, or its pharmaceutically acceptable salt, or its solvate as claimed in claim 2, wherein L$^3$ is —O—CH$_2$—.

* * * * *